(12) United States Patent
Burns, Jr.

(10) Patent No.: US 8,153,140 B2
(45) Date of Patent: Apr. 10, 2012

(54) CHIMERIC MSP-BASED MALARIA VACCINE

(75) Inventor: James M. Burns, Jr., Lansdale, PA (US)

(73) Assignee: Philadelphia Health and Education Corporation, Philadelphia, PA (US)

( * ) Notice: Subject to any disclaimer, the term of this patent is extended or adjusted under 35 U.S.C. 154(b) by 0 days.

(21) Appl. No.: 13/089,924

(22) Filed: Apr. 19, 2011

(65) Prior Publication Data
US 2011/0243982 A1 Oct. 6, 2011

Related U.S. Application Data

(62) Division of application No. 12/070,874, filed on Feb. 21, 2008, now Pat. No. 7,931,908.

(60) Provisional application No. 60/903,210, filed on Feb. 23, 2007.

(51) Int. Cl.
*A61K 39/015* (2006.01)
(52) U.S. Cl. ............... 424/272.1; 424/191.1; 424/192.1; 424/193.1; 424/194.1; 424/269.1
(58) Field of Classification Search .................... None
See application file for complete search history.

(56) References Cited

U.S. PATENT DOCUMENTS

| | | | |
|---|---|---|---|
| 4,837,016 A | 6/1989 | Holder et al. | |
| 5,597,708 A | 1/1997 | Holder et al. | |
| 5,720,959 A | 2/1998 | Holder et al. | |
| 6,551,586 B1 | 4/2003 | Davidson et al. | |
| 6,828,416 B1 | 12/2004 | Lal et al. | |
| 7,101,556 B2 | 9/2006 | Pan | |

FOREIGN PATENT DOCUMENTS

| EP | 0 062 924 | 10/1982 |
|---|---|---|
| GB | 2 096 893 | 10/1982 |
| GB | 2 099 300 | 12/1982 |

OTHER PUBLICATIONS

Black et al., "Merozoite surface protein 8 of *Plasmodium falciparum* contains two epidermal growth factor-like domains", Molecular and Biochemical Parasitology, 2001, 114(2): 217-226.
Blackman et al., "A Single Fragment of a Malaria Merozoite Surface Protein Remains on the Parasite During Red Cell Invasion and Is the Target of Invasion-inhibiting Antibodies", J. Exp. Med., 1990, 172: 379-382.
Blackman et al., "Proteolytic processing of the *Plasmodium falciparum* merozoite surface protein-1 produces a membrane-bound fragment containing two epidermal growth factor-like domains", Mol. Biochem. Parasitol., 1991, 49(1): 29-33, Abstract only.
Burghaus et al., "Immunization of *Aotus nancymai* with Recombinant C Terminus of *Plasmodium falciparum* Merozoite Surface Protein 1 in Liposomes and Alum Adjuvant Does Not Induce Protection against a Challenge Infection", Infection and Immunity, 1996, 64(9): 3614-3619.
Burns et al., "A protective monoclonal antibody recognizes an epitope in the carboxyl-terminal cysteine-rich domain in the precursor of the major merozoite surface antigen of the rodent malarial parasite, *Plasmodium yoelii*", J. Immunol., 1989, 143: 2670-2676.
Burns et al., "Protection against *Plasmodium chabaudi* malaria induced by immunization with apical membrane antigen 1 and merozoite surface protein 1 in the absence of gamma interferon or interleukin-4", Infection and Immunity, 2004, 72(10):5605-12.
Burns et al., "Protection against *Plasmodium yoelli* malaria induced by immunization with particulate blood-stage antigens", Infection and Immunity, 1997, 65(8):3138-3145.
Chang et al., "A Recombinant Baculovirus 42-Kilodalton C-Terminal Fragment of *Plasmodium falciparum* Merozoite Surface Protein 1 Protects Aotus Monkeys against Malaria", Infection and Immunity, 1996, 64(1): 253-261.
Cheung et al., "Cloning and expression in *Escherichia coli* of a surface antigen of *Plasmodium falciparum* merozoites", The EMBO Journal, 1985, 4(4): 1007-1012.
Chothia et al., "The relation between the divergence of sequence and structure in proteins." 1986, EMBO J. 5(4):826-26.
Daly et al., "Influence of Adjuvants on Protection Induced by a Recombinant Fusion Protein against Malarial Infection", Infection and Immunity, 1996, 64(7): 2602-2608.
Darko et al., "The Clinical-Grade 42-Kilodalton Fragment of Merozoite Surface Protein 1 of *Plasmodium falciparum* Strain FVO Expressed in *Escherichia coli* Protects *Aotus nancymai* against Challenge with Homologous Erythrocytic-Stage Parasites", Infection and Immunity, 2005, 73(1): 287-297.
Drew et al., "A Common Cross-species Function for the Double Epidermal Growth Factor-like Modules of the Highly Divergent Plasmodium Surface Proteins MSP-1 and MSP-8", The Journal of Biological Chemistry, 2004, 279(19): 20147-20158.
Drew et al., "*Plasmodium falciparum* Merozoite Surface Protein 8 Is a Ring-Stage Membrane Protein That Localizes to the Parasitophorous Vacuole of Infected Erythrocytes", Infection and Immunity, 2005, 73(7): 3912-3922.
Egan et al., "Serum Antibodies from Malaria-Exposed People Recognize Conserved Epitopes Formed by the Two Epidermal Growth Factor Motifs of MSP119, the Carboxy-Terminal Fragment of the Major Merozoite Surface Protein of *Plasmodium falciparum*", Infection and Immunity, 1995, 63(2): 456-466.
Freeman et al., "Surface Antigens of Malaria Merozoites", J. Exp. Med., 1983, 158: 1647-1653.
Galinski et al., 2005, pp. 113-168, "A Mechanistic Approach to Merozoite Invasion of Red Blood Cells: Merozoite Biogenesis, Rupture, and Invasion of Erythrocytes", In I. W. Sherman (ed), *Molecular Approaches to Malaria*, ASM Press, Washington DC. Gilson et al., "Identification and stoichiometry of GPI-anchored membrane proteins of the human malaria parasite *Plasmodium falciparum*", MCP Papers in Press. Published on Apr. 7, 2006 as Manuscript M600035-MCP200.
Greenspan et al., "Defining epitopes: It's not as easy as it seems." 1999, Nature Biotechnology 7:936-937.
Heppner, Jr. et al., "Towards an RTS, S-based, multi-stage, multi-antigen vaccine against falciparum malaria: progress at the Walter Reed Army Institute of Research", Vaccine 23: 2243-2250 (2005).
Holder et al., "Primary structure of the precursor to the three major surface antigens of *Plasmodium falciparum* merozoites", Nature, 1985, 317(6034): 270-273, Abstract only.
Holder et al., "The Three Major Antigens on the Surface of *Plasmodium falciparum* Merozoites are Derived from a Single High Molecular Weight Precursos", J Exp Med. 1984, 160:624-629.

(Continued)

*Primary Examiner* — Jennifer Graser
(74) *Attorney, Agent, or Firm* — Riverside Law LLP

(57) ABSTRACT

The invention provides an immunogenic composition comprising MSP-8 linked to an antigen. Methods of using the composition to induce an immune response in an animal are also provided.

6 Claims, 10 Drawing Sheets

OTHER PUBLICATIONS

Holder, 1996, pp. 77-104. In: S. L. Hoffman (ed), Malaria vaccine development: a multi-immune response approach, ASM Press, Washington DC.

Kumar et al., "Immunogenicity and Efficacy in Aotus Monkeys of Four Recombinant *Plasmodium falciparum* Vaccines in Multiple Adjuvant Formulations Based on the 19-Kilodalton C Terminus of Merozoite Surface Protein 1", Infection and Immunity, 2000, 68(4): 2215-2223.

Kumar et al., "Immunogenicity and In Vivo Efficiency of Recombinant *Plasmodium falciparum* Merozoite Surface Protein-1 in Aotus Monkeys", Mol Med., 1995, 1:325-332.

Lyon et al., "Epitope map and processing scheme for the 195,000-dalton surface glycoprotein of *Plasmodium falciparum* merozoites deduced from cloned overlapping segments of the gene", Proc. Natl. Acad. Sci. USA, 1986, 83: 2989-2993.

Mackay et al., "Polymorphism of the precursor for the major surface antigens of *Plasmodium falciparum* merozoites: studies at the genetic level", The EMBO Journal, 1985, 4(13B): 3823-3829.

Mahanty et al., "Progress in the development of recombinant and synthetic blood-stage malaria vaccines", The Journal of Experimental Biology, 2003, 206: 3781-3788.

Malaria Vaccine Initiative, Falciparum Malaria MSP1 Workshop Progress Toward MSP1 Vaccine Development and Testing, Dec. 4, 2000 [online], [retrieved on Feb. 6, 2008]. Retrieved from the Internet <URL:www.malariavaccine.org/files/msp1-wksp.pdf.

Mello et al., "Members of the merozoite surface protein 7 family with similar expression patterns differ in ability to protect against *Plasmodium yoelii* malaria", Infection and Immunity, 2004, 72(2):1010-8.

Mikayama et al., "Molecular cloning and functional expression of a cDNA encoding glycosylation-inhibiting factor." 1993, Proc Natl Acad Sci USA 90:10056-10060.

O'Donnell et al., "Antibodies Against Merozoite Surface Protein (MSP)-119 are a Major Component of the Invasion-inhibitory Response in Individuals Immune to Malaria", J. Exp. Med., 2001, 193(12): 1403-1412.

O'Donnell et al., "Functional conservation of the malaria vaccine antigen MSP-119 across distantly related *Plasmodium* species", Nature Medicine, 2000, 6(1): 91-95.

Ockenhouse et al., "Phase I safety and immunogenicity trial of FMP1/AS02A, a *Plasmodium falciparum* MSP-1 asexual blood stage vaccine", Vaccine 24: 3009-3017 (2006).

Richie et al., "Progress and challenges for malaria vaccines", Nature 415: 694-701 (2002).

Rudinger et al., "Characteristics of the amino acids as components of a peptide hormone sequence." 1976, Peptide Hormones Biol. Council. pp. 5-7.

Shi et al., "Expression, localization, and erythrocyte binding activity of *Plasmodium yoelii* merozoite surface protein-8", Mol Biochem Parasitol., 2006, 149(2):231-41. Epub Jun. 30, 2006.

Shi et al., "Alteration in Host Cell Tropism Limits the Efficacy of Immunization with a Surface Protein of Malaria Merozoites", Infection and Immunity, 2005, 73(10): 6363-6371.

Shi et al., "Enhanced Protection against Malaria by a Chimeric Merozoite Surface Protein Vaccine", Infection and Immunity, 2007, 75(3): 1349-1358.

Shi et al., "Improved immunogenicity and protective efficacy of a chimeric MSP-1 and MSP-8 recombinant antigen vaccine", Poster abstract, ASTMH 55th Annual Meeting, Nov. 12-16, 2006.

Stoute et al., "Phase 1 randomized double-blind safety and immunogenicity trial of *Plasmodium falciparum* malaria merozoite surface protein FMP1 vaccine, adjuvanted with AS02A, in adults in western Kenya", Vaccine 25: 176-184 (2007).

Stowers et al., "Efficacy of Two Alternate Vaccines Based on *Plasmodium falciparum* Merozoite Surface Protein 1 in an Aotus Challenge Trial", Infection and Immunity, 2001, 69(3): 1536-1546.

Tanabe et al., "Allelic dimorphism in a surface antigen gene of the malaria parasite *Plasmodium falciparum*", J. Mol. Biol., 1987, 195(2): 273-287, Abstract only.

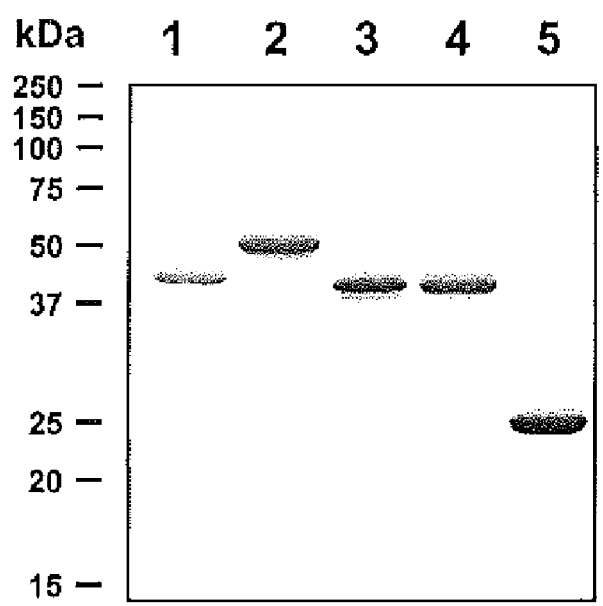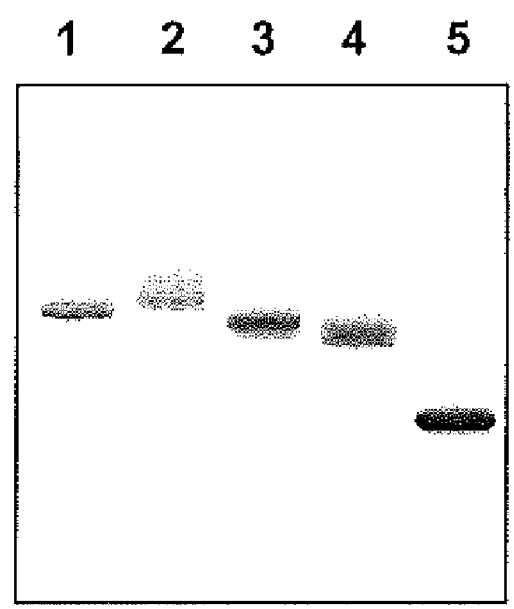
Figure 1A — reduced
Figure 1B — non-reduced

His$_6$    PyMSP-1$_{19}$ Gly           PyMSP-8

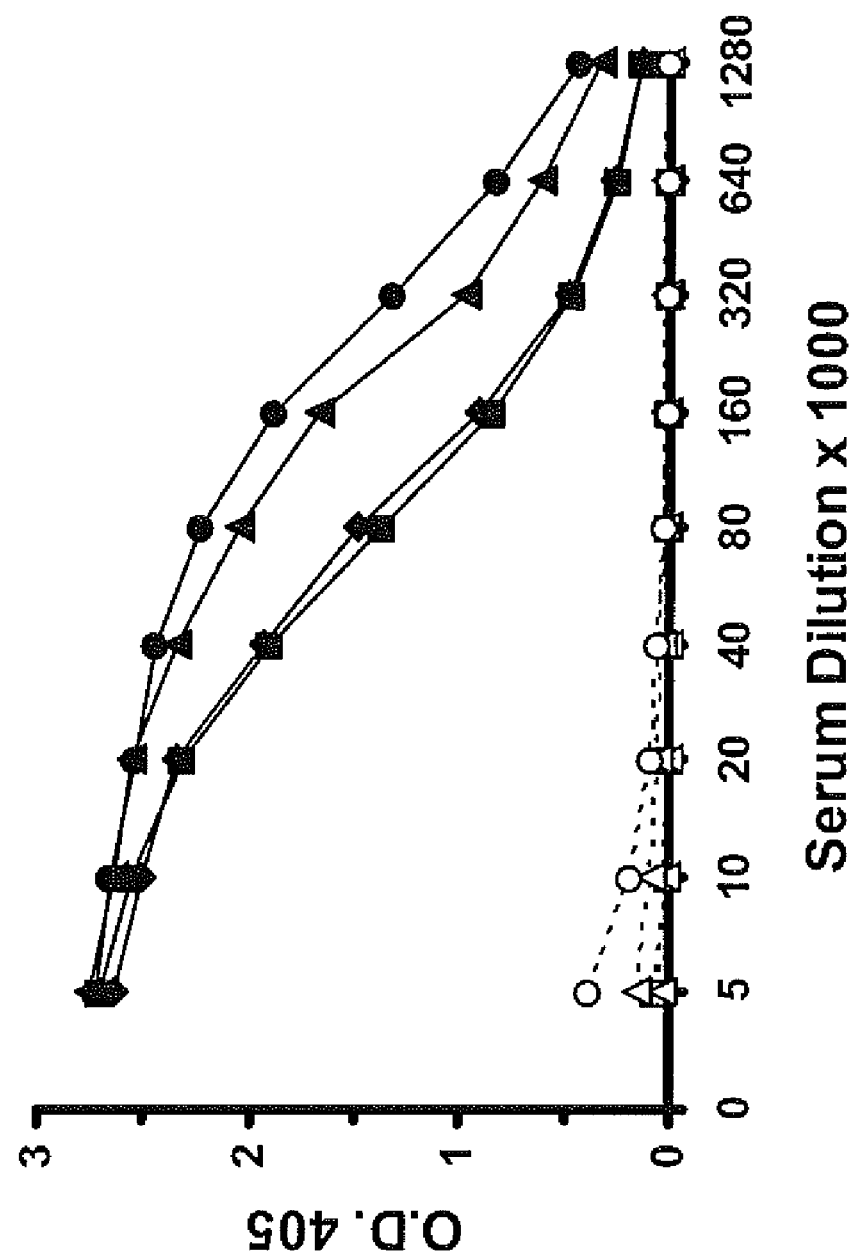

SEQUENCE LISTING

```
<160> NUMBER OF SEQ ID NOS: 23

<210> SEQ ID NO 1
<211> LENGTH: 2103
<212> TYPE: DNA
<213> ORGANISM: Plasmodium yoelii
<220> FEATURE:
<221> NAME/KEY: CDS
<222> LOCATION: (253)..(1482)
<220> FEATURE:
<221> NAME/KEY: sig_peptide
<222> LOCATION: (253)..(318)
<220> FEATURE:
<221> NAME/KEY: misc_feature
<222> LOCATION: (1417)..(1419)
```

-continued

<223> OTHER INFORMATION: predicted GPI-attachment site in encoded
     protein

<400> SEQUENCE: 1

```
taatttccaa atgtaatttt ttttaaatgc aaaaaaaata gtatatatat atttaaaaaa      60
ttatttcttg ttaaattttg tatctttatt aaaaaaaaaa aaaaaaaaaa aaaaccttaa     120
ttctaacaac ccgcataaca atagaatata atttctattc ttatagattt ataaatatta    180
taaaatatat atccatttta aaaaaaaaaa aaaatattgt ttacacttag atattttatt    240
agtatataaa aa atg aaa aag agt tca caa ata ata att ttt ttg tta tta    291
              Met Lys Lys Ser Ser Gln Ile Ile Ile Phe Leu Leu Leu
               1               5                  10 tca tta ttt tgt aaa ttt agt atc ggg aat tgt aat gaa aat gga aac     339
Ser Leu Phe Cys Lys Phe Ser Ile Gly Asn Cys Asn Glu Asn Gly Asn
 15              20                  25 ggt aat ata aat aaa gcc aat aat aat agt ata ata aga aaa gaa aga     387
Gly Asn Ile Asn Lys Ala Asn Asn Asn Ser Ile Ile Arg Lys Glu Arg
 30              35                  40                  45 aaa aga aaa agt aaa agt gat ttt agt aaa ggg gaa cct gaa aat aag     435
Lys Arg Lys Ser Lys Ser Asp Phe Ser Lys Gly Glu Pro Glu Asn Lys
             50                  55                  60 gaa cat gaa att att aat tta tat gat gat gtg caa gaa tta tta gga     483
Glu His Glu Ile Ile Asn Leu Tyr Asp Asp Val Gln Glu Leu Leu Gly
             65                  70                  75 ccc gac gaa atg aat atg tta gac aaa tat tca ata tta gga ata gat     531
Pro Asp Glu Met Asn Met Leu Asp Lys Tyr Ser Ile Leu Gly Ile Asp
             80                  85                  90 gat tgt tct aat gaa aat gaa aat aat aaa ata att agc gaa tat gat     579
Asp Cys Ser Asn Glu Asn Glu Asn Asn Lys Ile Ile Ser Glu Tyr Asp
 95                 100                 105 ctt aaa gca atg aag agt gta tta tta tat aaa aac cga ata tca aga     627
Leu Lys Ala Met Lys Ser Val Leu Leu Tyr Lys Asn Arg Ile Ser Arg
110             115                 120                 125 gca tca ata aac aat tta gat gat gtt aaa act gta ttt aaa aga tgt     675
Ala Ser Ile Asn Asn Leu Asp Asp Val Lys Thr Val Phe Lys Arg Cys
                130                 135                 140 ttt aat aag gat gat cct gaa tta agt aaa agt tat gaa caa atc caa     723
Phe Asn Lys Asp Asp Pro Glu Leu Ser Lys Ser Tyr Glu Gln Ile Gln
            145                 150                 155 aac caa gta gct aac gaa gga aca act ata ata gat tat tta tca aat     771
Asn Gln Val Ala Asn Glu Gly Thr Thr Ile Ile Asp Tyr Leu Ser Asn
            160                 165                 170 tat att tca aat att tat att aaa ata aat gat gaa ttt gta aaa aat     819
Tyr Ile Ser Asn Ile Tyr Ile Lys Ile Asn Asp Glu Phe Val Lys Asn
175             180                 185 gaa gaa ttt caa cta tca aaa tat att cct gaa ctt gaa ata att aat     867
Glu Glu Phe Gln Leu Ser Lys Tyr Ile Pro Glu Leu Glu Ile Ile Asn
190             195                 200                 205 tat gta ctt tat aat gga cct aaa gaa ata gga aac aaa ata aaa aat     915
Tyr Val Leu Tyr Asn Gly Pro Lys Glu Ile Gly Asn Lys Ile Lys Asn
                210                 215                 220 gaa tta atc gaa ata aat aat tta ata ata tct gaa tct ctt acc tca     963
Glu Leu Ile Glu Ile Asn Asn Leu Ile Ile Ser Glu Ser Leu Thr Ser
            225                 230                 235 ata tat agt tct gtt gtt tca ggg tta aat ata aat tgt aaa att aaa    1011
Ile Tyr Ser Ser Val Val Ser Gly Leu Asn Ile Asn Cys Lys Ile Lys
            240                 245                 250 gat gat tta ata act ata ctt aat tta gca aat ggt aaa tat ttt aaa    1059
Asp Asp Leu Ile Thr Ile Leu Asn Leu Ala Asn Gly Lys Tyr Phe Lys
            255                 260                 265
```

| | | | | | | | | | | | | | | | | |
|---|---|---|---|---|---|---|---|---|---|---|---|---|---|---|---|---|
| gta | aat | ttt | agt | agt | caa | gct | aca | atg | att | att | cct | gag | caa | tat | tct | 1107 |
| Val | Asn | Phe | Ser | Ser | Gln | Ala | Thr | Met | Ile | Ile | Pro | Glu | Gln | Tyr | Ser | |
| 270 | | | | | 275 | | | | | 280 | | | | | 285 | |
| cat | gaa | tct | gag | cac | atg | aaa | aaa | ata | tca | gaa | tat | ttt | att | gaa | aaa | 1155 |
| His | Glu | Ser | Glu | His | Met | Lys | Lys | Ile | Ser | Glu | Tyr | Phe | Ile | Glu | Lys | |
| | | | | 290 | | | | | 295 | | | | | 300 | | |
| aat | cga | gtt | tgt | aaa | aat | gag | aac | tgt | cca | atc | aat | tca | aat | tgt | tat | 1203 |
| Asn | Arg | Val | Cys | Lys | Asn | Glu | Asn | Cys | Pro | Ile | Asn | Ser | Asn | Cys | Tyr | |
| | | | 305 | | | | | 310 | | | | | 315 | | | |
| gtt | att | gat | agt | gta | gaa | act | tgt | aga | tgt | att | cca | gga | ttt | tct | aaa | 1251 |
| Val | Ile | Asp | Ser | Val | Glu | Thr | Cys | Arg | Cys | Ile | Pro | Gly | Phe | Ser | Lys | |
| | | 320 | | | | | 325 | | | | | 330 | | | | |
| aat | gaa | gaa | agc | gaa | aat | tta | gaa | tgt | tta | ata | aat | gaa | tct | act | tct | 1299 |
| Asn | Glu | Glu | Ser | Glu | Asn | Leu | Glu | Cys | Leu | Ile | Asn | Glu | Ser | Thr | Ser | |
| 335 | | | | | 340 | | | | | 345 | | | | | | |
| tgt | gaa | aat | aat | aat | ggt | gga | tgt | gat | gta | aat | gca | aat | tgt | ata | tta | 1347 |
| Cys | Glu | Asn | Asn | Asn | Gly | Gly | Cys | Asp | Val | Asn | Ala | Asn | Cys | Ile | Leu | |
| 350 | | | | | 355 | | | | | 360 | | | | | 365 | |
| tta | gaa | gat | aaa | ata | atg | tgt | gaa | tgt | aat | aac | aaa | ttt | aat | gga | gat | 1395 |
| Leu | Glu | Asp | Lys | Ile | Met | Cys | Glu | Cys | Asn | Asn | Lys | Phe | Asn | Gly | Asp | |
| | | | | 370 | | | | | 375 | | | | | 380 | | |
| ggt | att | tat | tgt | tca | agt | gcc | att | tat | tat | gga | atg | aat | gtt | ttt | att | 1443 |
| Gly | Ile | Tyr | Cys | Ser | Ser | Ala | Ile | Tyr | Tyr | Gly | Met | Asn | Val | Phe | Ile | |
| | | | 385 | | | | | 390 | | | | | 395 | | | |
| ttc | ttt | tta | att | tca | ata | gta | tgc | ata | tat | ata | tgt | taa | gaatgttgca | | | 1492 |
| Phe | Phe | Leu | Ile | Ser | Ile | Val | Cys | Ile | Tyr | Ile | Met | | | | | |
| | | 400 | | | | | 405 | | | | | | | | | |

| | |
|---|---|
| tgtttttttaa ataatcatgt aatatattat taatataatt tttaccatga ttgggtttta | 1552 |
| ttattaatat ttttccgaat atatatcgaa aaaaatatgt ttttgctggt atatacaata | 1612 |
| atataatatg gcacatatct tatgaagttt tttttacttt atatgcatta tatatgcatt | 1672 |
| atttatacat tatatatttt ttgaatcata tctaatgtat aattaatcca gtccgaataa | 1732 |
| tgaatattga aaatgttcat tgatctttac taaaagcgta tatatataca tgcagatata | 1792 |
| aatatataca cattgtggct gtacttgaat gttgcccatt ttgatcatta ctatacattc | 1852 |
| acaaataata tatttataag ggcgcaataa ttaatatacc acaattttca agctgcatag | 1912 |
| ttgcatagtt gcatagtttc atagttgcat agctgcatag ttgcataatt tttaattcgt | 1972 |
| ttagccctat atatgtgcat gattatttta tattttgtta atatgcatat atggtattat | 2032 |
| ttgaaacaat ttttatatta aaaaaaaaca aataaaagta atttcaggta tataaaaaaa | 2092 |
| aaaaaaaaaa a | 2103 |

<210> SEQ ID NO 2
<211> LENGTH: 409
<212> TYPE: PRT
<213> ORGANISM: Plasmodium yoelii

<400> SEQUENCE: 2

Met Lys Lys Ser Ser Gln Ile Ile Ile Phe Leu Leu Ser Leu Phe
1               5                   10                  15

Cys Lys Phe Ser Ile Gly Asn Cys Asn Glu Asn Gly Asn Gly Asn Ile
                20                  25                  30

Asn Lys Ala Asn Asn Asn Ser Ile Ile Arg Lys Glu Arg Lys Arg Lys
            35                  40                  45

Ser Lys Ser Asp Phe Ser Lys Gly Glu Pro Glu Asn Lys Glu His Glu
        50                  55                  60

Ile Ile Asn Leu Tyr Asp Asp Val Gln Glu Leu Leu Gly Pro Asp Glu

|     |     |     |     | 65  |     |     |     |     | 70  |     |     |     |     | 75  |     |     |     |     | 80  |
|-----|-----|-----|-----|-----|-----|-----|-----|-----|-----|-----|-----|-----|-----|-----|-----|-----|-----|-----|-----|

Met Asn Met Leu Asp Lys Tyr Ser Ile Leu Gly Ile Asp Asp Cys Ser
                                            85                    90                    95

Asn Glu Asn Glu Asn Asn Lys Ile Ile Ser Glu Tyr Asp Leu Lys Ala
            100                   105                   110

Met Lys Ser Val Leu Leu Tyr Lys Asn Arg Ile Ser Arg Ala Ser Ile
        115                   120                   125

Asn Asn Leu Asp Asp Val Lys Thr Val Phe Lys Arg Cys Phe Asn Lys
    130                   135                   140

Asp Asp Pro Glu Leu Ser Lys Ser Tyr Glu Gln Ile Gln Asn Gln Val
145                   150                   155                   160

Ala Asn Glu Gly Thr Thr Ile Ile Asp Tyr Leu Ser Asn Tyr Ile Ser
                165                   170                   175

Asn Ile Tyr Ile Lys Ile Asn Asp Glu Phe Val Lys Asn Glu Phe
            180                   185                   190

Gln Leu Ser Lys Tyr Ile Pro Glu Leu Glu Ile Ile Asn Tyr Val Leu
        195                   200                   205

Tyr Asn Gly Pro Lys Glu Ile Gly Asn Lys Ile Lys Asn Glu Leu Ile
    210                   215                   220

Glu Ile Asn Asn Leu Ile Ile Ser Glu Ser Leu Thr Ser Ile Tyr Ser
225                   230                   235                   240

Ser Val Val Ser Gly Leu Asn Ile Asn Cys Lys Ile Lys Asp Asp Leu
                245                   250                   255

Ile Thr Ile Leu Asn Leu Ala Asn Gly Lys Tyr Phe Lys Val Asn Phe
            260                   265                   270

Ser Ser Gln Ala Thr Met Ile Ile Pro Glu Gln Tyr Ser His Glu Ser
        275                   280                   285

Glu His Met Lys Lys Ile Ser Glu Tyr Phe Ile Glu Lys Asn Arg Val
    290                   295                   300

Cys Lys Asn Glu Asn Cys Pro Ile Asn Ser Asn Cys Tyr Val Ile Asp
305                   310                   315                   320

Ser Val Glu Thr Cys Arg Cys Ile Pro Gly Phe Ser Lys Asn Glu Glu
                325                   330                   335

Ser Glu Asn Leu Glu Cys Leu Ile Asn Glu Ser Thr Ser Cys Glu Asn
            340                   345                   350

Asn Asn Gly Gly Cys Asp Val Asn Ala Asn Cys Ile Leu Leu Glu Asp
        355                   360                   365

Lys Ile Met Cys Glu Cys Asn Asn Lys Phe Asn Gly Asp Gly Ile Tyr
    370                   375                   380

Cys Ser Ser Ala Ile Tyr Tyr Gly Met Asn Val Phe Ile Phe Phe Leu
385                   390                   395                   400

Ile Ser Ile Val Cys Ile Tyr Ile Met
                405

<210> SEQ ID NO 3
<211> LENGTH: 1815
<212> TYPE: DNA
<213> ORGANISM: Plasmodium falciparum
<220> FEATURE:
<221> NAME/KEY: CDS
<222> LOCATION: (1)..(1815)
<220> FEATURE:
<221> NAME/KEY: sig_peptide
<222> LOCATION: (1)..(72)
<220> FEATURE:
<221> NAME/KEY: misc_feature
<222> LOCATION: (1749)..(1751)
<223> OTHER INFORMATION: predicted GPI-attachment site in encoded protein

<400> SEQUENCE: 3

| | | | | | | | | | | | | | | | | |
|---|---|---|---|---|---|---|---|---|---|---|---|---|---|---|---|---|
| atg | gtg | ttc | aaa | agt | tcg | gac | ata | ttt | ttc | ttt | ctc | ttc | ctt | gtg | ata | 48 |
| Met | Val | Phe | Lys | Ser | Ser | Asp | Ile | Phe | Phe | Phe | Leu | Phe | Leu | Val | Ile | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctt | tat | ttt | aat | aac | gtt | gta | gaa | ggg | gag | aat | gga | act | aca | aat | atc | 96 |
| Leu | Tyr | Phe | Asn | Asn | Val | Val | Glu | Gly | Glu | Asn | Gly | Thr | Thr | Asn | Ile | |
| | | | 20 | | | | | 25 | | | | | 30 | | | |

| | | | | | | | | | | | | | | | | |
|---|---|---|---|---|---|---|---|---|---|---|---|---|---|---|---|---|
| gaa | aat | aat | cct | gga | aat | aat | ggt | aat | atg | gga | cca | tca | gga | cca | aaa | 144 |
| Glu | Asn | Asn | Pro | Gly | Asn | Asn | Gly | Asn | Met | Gly | Pro | Ser | Gly | Pro | Lys | |
| | | 35 | | | | | 40 | | | | | 45 | | | | |

| | | | | | | | | | | | | | | | | |
|---|---|---|---|---|---|---|---|---|---|---|---|---|---|---|---|---|
| gat | aaa | gac | aag | aat | att | gaa | aag | gat | gta | aat | cac | aac | atg | agt | atg | 192 |
| Asp | Lys | Asp | Lys | Asn | Ile | Glu | Lys | Asp | Val | Asn | His | Asn | Met | Ser | Met | |
| 50 | | | | | 55 | | | | | 60 | | | | | | |

| | | | | | | | | | | | | | | | | |
|---|---|---|---|---|---|---|---|---|---|---|---|---|---|---|---|---|
| aat | aat | aat | aat | aat | aat | aat | aat | aat | aat | gac | aat | aat | aat | aat | ata | 240 |
| Asn | Asn | Asn | Asn | Asn | Asn | Asn | Asn | Asn | Asn | Asp | Asn | Asn | Asn | Asn | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aat | aac | aat | aat | aat | aat | aat | ata | aat | aac | aac | acc | aat | aat | aat | aat | 288 |
| Asn | Asn | Asn | Asn | Asn | Asn | Asn | Ile | Asn | Asn | Asn | Thr | Asn | Asn | Asn | Asn | |
| | | | | 85 | | | | | 90 | | | | | 95 | | |

| | | | | | | | | | | | | | | | | |
|---|---|---|---|---|---|---|---|---|---|---|---|---|---|---|---|---|
| aat | ata | aat | aac | aac | aac | aat | aat | aat | aat | aat | ggt | aat | gga | ttt | 336 |
| Asn | Ile | Asn | Asn | Asn | Asn | Asn | Asn | Asn | Asn | Asn | Gly | Asn | Gly | Phe | |
| | | | 100 | | | | | 105 | | | | | 110 | | | |

| | | | | | | | | | | | | | | | | |
|---|---|---|---|---|---|---|---|---|---|---|---|---|---|---|---|---|
| tca | aat | ttt | ttt | aat | aaa | ctt | ttt | gga | aaa | aaa | aaa | gat | aac | aaa | aaa | 384 |
| Ser | Asn | Phe | Phe | Asn | Lys | Leu | Phe | Gly | Lys | Lys | Lys | Asp | Asn | Lys | Lys | |
| | | 115 | | | | | 120 | | | | | 125 | | | | |

| | | | | | | | | | | | | | | | | |
|---|---|---|---|---|---|---|---|---|---|---|---|---|---|---|---|---|
| gag | gga | gaa | gaa | aaa | aat | gaa | gaa | gat | tta | aat | agt | aat | aag | aac | att | 432 |
| Glu | Gly | Glu | Glu | Lys | Asn | Glu | Glu | Asp | Leu | Asn | Ser | Asn | Lys | Asn | Ile | |
| 130 | | | | | 135 | | | | | 140 | | | | | | |

| | | | | | | | | | | | | | | | | |
|---|---|---|---|---|---|---|---|---|---|---|---|---|---|---|---|---|
| gaa | agt | aat | aag | ggg | agt | gct | gta | act | tct | aat | gta | ggg | gat | aca | aat | 480 |
| Glu | Ser | Asn | Lys | Gly | Ser | Ala | Val | Thr | Ser | Asn | Val | Gly | Asp | Thr | Asn | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| aat | gac | gca | aaa | gca | agg | gac | aac | aat | aat | gat | gat | aat | gat | gat | 528 |
| Asn | Asp | Ala | Lys | Ala | Arg | Asp | Asn | Asn | Asn | Asp | Asp | Asn | Asp | Asp | |
| | | | 165 | | | | | 170 | | | | | 175 | | | |

| | | | | | | | | | | | | | | | | |
|---|---|---|---|---|---|---|---|---|---|---|---|---|---|---|---|---|
| aat | gac | gag | aat | gat | gat | aat | gat | gat | aat | gat | gat | att | gat | gag | att | 576 |
| Asn | Asp | Glu | Asn | Asp | Asp | Asn | Asp | Asp | Asn | Asp | Asp | Ile | Asp | Glu | Ile | |
| | | | 180 | | | | | 185 | | | | | 190 | | | |

| | | | | | | | | | | | | | | | | |
|---|---|---|---|---|---|---|---|---|---|---|---|---|---|---|---|---|
| gat | gaa | cgt | gat | gat | aat | gat | gat | aat | ggt | gat | gat | gat | gat | gat | aat | 624 |
| Asp | Glu | Arg | Asp | Asp | Asn | Asp | Asp | Asn | Gly | Asp | Asp | Asp | Asp | Asp | Asn | |
| | | 195 | | | | | 200 | | | | | 205 | | | | |

| | | | | | | | | | | | | | | | | |
|---|---|---|---|---|---|---|---|---|---|---|---|---|---|---|---|---|
| gat | gat | gac | gat | gat | aat | aat | gat | aat | aat | aat | aaa | aat | aat | agt | aat | 672 |
| Asp | Asp | Asp | Asp | Asp | Asn | Asn | Asp | Asn | Asn | Asn | Lys | Asn | Asn | Ser | Asn | |
| | | 210 | | | | | 215 | | | | | 220 | | | | |

| | | | | | | | | | | | | | | | | |
|---|---|---|---|---|---|---|---|---|---|---|---|---|---|---|---|---|
| aat | tta | acg | gat | aca | aaa | aag | gaa | ggg | gag | aaa | att | gat | tta | gga | gtt | 720 |
| Asn | Leu | Thr | Asp | Thr | Lys | Lys | Glu | Gly | Glu | Lys | Ile | Asp | Leu | Gly | Val | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| caa | aat | aaa | aaa | caa | aat | att | ttt | tca | acc | aac | aat | aaa | gga | tta | aat | 768 |
| Gln | Asn | Lys | Lys | Gln | Asn | Ile | Phe | Ser | Thr | Asn | Asn | Lys | Gly | Leu | Asn | |
| | | | | 245 | | | | | 250 | | | | | 255 | | |

| | | | | | | | | | | | | | | | | |
|---|---|---|---|---|---|---|---|---|---|---|---|---|---|---|---|---|
| aaa | tat | aat | ata | gat | aat | gaa | tta | aaa | gaa | gta | gat | gca | ctt | ttg | aaa | 816 |
| Lys | Tyr | Asn | Ile | Asp | Asn | Glu | Leu | Lys | Glu | Val | Asp | Ala | Leu | Leu | Lys | |
| | | | 260 | | | | | 265 | | | | | 270 | | | |

| | | | | | | | | | | | | | | | | |
|---|---|---|---|---|---|---|---|---|---|---|---|---|---|---|---|---|
| aat | gat | aat | tat | att | tta | aac | aaa | tac | cat | gtt | tca | ttt | ttt | aat | aat | 864 |
| Asn | Asp | Asn | Tyr | Ile | Leu | Asn | Lys | Tyr | His | Val | Ser | Phe | Phe | Asn | Asn | |
| | | 275 | | | | | 280 | | | | | 285 | | | | |

| | | | | | | | | | | | | | | | | |
|---|---|---|---|---|---|---|---|---|---|---|---|---|---|---|---|---|
| ttt | gaa | gaa | gat | aca | tat | aat | aag | aag | aaa | ttt | ata | aga | ccg | tat | gat | 912 |
| Phe | Glu | Glu | Asp | Thr | Tyr | Asn | Lys | Lys | Lys | Phe | Ile | Arg | Pro | Tyr | Asp | |
| | 290 | | | | | 295 | | | | | 300 | | | | | |

```
                                    -continued
ctt agc ttg tta aaa agt ata tta ata tat aga caa aga gta aca aga      960
Leu Ser Leu Leu Lys Ser Ile Leu Ile Tyr Arg Gln Arg Val Thr Arg
305                 310                 315                 320 aat tgt gtt aat gtt ttt caa gat ctc aat gct gtt ttt ggt aaa tgt     1008
Asn Cys Val Asn Val Phe Gln Asp Leu Asn Ala Val Phe Gly Lys Cys
                325                 330                 335 tat aat aaa gat gac act aaa tta agt att act cgt gat aaa gtt aaa     1056
Tyr Asn Lys Asp Asp Thr Lys Leu Ser Ile Thr Arg Asp Lys Val Lys
            340                 345                 350 aaa gag tta agt agg aaa aat aga aat ttt gta gaa tac tta att gaa     1104
Lys Glu Leu Ser Arg Lys Asn Arg Asn Phe Val Glu Tyr Leu Ile Glu
        355                 360                 365 atg tta gaa aat acc ctt aat agt atg aat gat gat ttt att aat aaa     1152
Met Leu Glu Asn Thr Leu Asn Ser Met Asn Asp Asp Phe Ile Asn Lys
    370                 375                 380 gat aat ttt gat tta aat aat tat gtt aaa gaa ttt gaa tta ata aat     1200
Asp Asn Phe Asp Leu Asn Asn Tyr Val Lys Glu Phe Glu Leu Ile Asn
385                 390                 395                 400 tat tta tta ata cat gaa gat tca gat ata ttt tta gaa aca tat aat     1248
Tyr Leu Leu Ile His Glu Asp Ser Asp Ile Phe Leu Glu Thr Tyr Asn
                405                 410                 415 tta ata agt gga tta aat tca aac ata gaa gaa aca tct att gaa aag     1296
Leu Ile Ser Gly Leu Asn Ser Asn Ile Glu Glu Thr Ser Ile Glu Lys
            420                 425                 430 ctt aaa tat gca ata tta caa gga aaa caa atc aat tac aaa att aag     1344
Leu Lys Tyr Ala Ile Leu Gln Gly Lys Gln Ile Asn Tyr Lys Ile Lys
        435                 440                 445 gat gat att tat tat atc ctt aaa aat gca tat gcg aaa tat ttt aaa     1392
Asp Asp Ile Tyr Tyr Ile Leu Lys Asn Ala Tyr Ala Lys Tyr Phe Lys
    450                 455                 460 att gat gta tat aaa aaa gga aaa tta tta tat cca act tta tat tat     1440
Ile Asp Val Tyr Lys Lys Gly Lys Leu Leu Tyr Pro Thr Leu Tyr Tyr
465                 470                 475                 480 cat aga aat gca ttt ata aaa tct ttt gta gtc gaa ttt ttt aat aat     1488
His Arg Asn Ala Phe Ile Lys Ser Phe Val Val Glu Phe Phe Asn Asn
                485                 490                 495 aat aaa gta tgt gag aat aca aag tgt cct ctt aat tcc aat tgt tat     1536
Asn Lys Val Cys Glu Asn Thr Lys Cys Pro Leu Asn Ser Asn Cys Tyr
            500                 505                 510 gtt ata gat gat gaa gaa acc tgt aga tgt cta cct gga ttt aat aat     1584
Val Ile Asp Asp Glu Glu Thr Cys Arg Cys Leu Pro Gly Phe Asn Asn
        515                 520                 525 ata aaa att gat gat gaa atg aat tgt gta agg gat gat aca tta gat     1632
Ile Lys Ile Asp Asp Glu Met Asn Cys Val Arg Asp Asp Thr Leu Asp
    530                 535                 540 tgt tct aga aat aat gga gga tgt gat ata cat gct aaa tgt tcc ttt     1680
Cys Ser Arg Asn Asn Gly Gly Cys Asp Ile His Ala Lys Cys Ser Phe
545                 550                 555                 560 ata aat aaa caa att gtg tgt gaa tgt aag gat aaa ttt gaa ggt gat     1728
Ile Asn Lys Gln Ile Val Cys Glu Cys Lys Asp Lys Phe Glu Gly Asp
                565                 570                 575 gga ata tat tgt tcc tat tct ttt ttt agt tca ata cat aat ttt ata     1776
Gly Ile Tyr Cys Ser Tyr Ser Phe Phe Ser Ser Ile His Asn Phe Ile
            580                 585                 590 ttc ttt ttt ata ttg tgt cta ttt att ttt att tta tag                 1815
Phe Phe Phe Ile Leu Cys Leu Phe Ile Phe Ile Leu
        595                 600

<210> SEQ ID NO 4
<211> LENGTH: 604
<212> TYPE: PRT
```

-continued

<213> ORGANISM: Plasmodium falciparum

<400> SEQUENCE: 4

```
Met Val Phe Lys Ser Ser Asp Ile Phe Phe Phe Leu Phe Leu Val Ile
  1               5                  10                  15

Leu Tyr Phe Asn Asn Val Val Glu Gly Glu Asn Gly Thr Thr Asn Ile
             20                  25                  30

Glu Asn Asn Pro Gly Asn Asn Gly Asn Met Gly Pro Ser Gly Pro Lys
         35                  40                  45

Asp Lys Asp Lys Asn Ile Glu Lys Asp Val Asn His Asn Met Ser Met
     50                  55                  60

Asn Asn Asn Asn Asn Asn Asn Asn Asp Asn Asn Asn Asn Asn Asn Ile
 65                  70                  75                  80

Asn Asn Asn Asn Asn Asn Ile Asn Asn Asn Thr Asn Asn Asn Asn Asn
                 85                  90                  95

Asn Ile Asn Asn Asn Asn Asn Asn Asn Asn Gly Asn Gly Phe
            100                 105                 110

Ser Asn Phe Phe Asn Lys Leu Phe Gly Lys Lys Asp Asn Lys Lys
        115                 120                 125

Glu Gly Glu Glu Lys Asn Glu Glu Asp Leu Asn Ser Asn Lys Asn Ile
    130                 135                 140

Glu Ser Asn Lys Gly Ser Ala Val Thr Ser Asn Val Gly Asp Thr Asn
145                 150                 155                 160

Asn Asp Ala Lys Ala Arg Asp Asn Asn Asn Asp Asp Asn Asp Asp
                165                 170                 175

Asn Asp Glu Asn Asp Asp Asn Asp Asn Asp Asp Ile Asp Glu Ile
            180                 185                 190

Asp Glu Arg Asp Asp Asn Asp Asn Gly Asp Asp Asp Asp Asn
        195                 200                 205

Asp Asp Asp Asp Asn Asn Asp Asn Asn Asn Lys Asn Asn Ser Asn
    210                 215                 220

Asn Leu Thr Asp Thr Lys Lys Glu Gly Glu Lys Ile Asp Leu Gly Val
225                 230                 235                 240

Gln Asn Lys Lys Gln Asn Ile Phe Ser Thr Asn Asn Lys Gly Leu Asn
                245                 250                 255

Lys Tyr Asn Ile Asp Asn Glu Leu Lys Glu Val Asp Ala Leu Leu Lys
            260                 265                 270

Asn Asp Asn Tyr Ile Leu Asn Lys Tyr His Val Ser Phe Phe Asn Asn
        275                 280                 285

Phe Glu Glu Asp Thr Tyr Asn Lys Lys Lys Phe Ile Arg Pro Tyr Asp
    290                 295                 300

Leu Ser Leu Leu Lys Ser Ile Leu Ile Tyr Arg Gln Arg Val Thr Arg
305                 310                 315                 320

Asn Cys Val Asn Val Phe Gln Asp Leu Asn Ala Val Phe Gly Lys Cys
                325                 330                 335

Tyr Asn Lys Asp Asp Thr Lys Leu Ser Ile Thr Arg Asp Lys Val Lys
            340                 345                 350

Lys Glu Leu Ser Arg Lys Asn Arg Asn Phe Val Glu Tyr Leu Ile Glu
        355                 360                 365

Met Leu Glu Asn Thr Leu Asn Ser Met Asn Asp Phe Ile Asn Lys
    370                 375                 380

Asp Asn Phe Asp Leu Asn Asn Tyr Val Lys Glu Phe Glu Leu Ile Asn
385                 390                 395                 400

Tyr Leu Leu Ile His Glu Asp Ser Asp Ile Phe Leu Glu Thr Tyr Asn
```

```
                    405                 410                 415
Leu Ile Ser Gly Leu Asn Ser Asn Ile Glu Glu Thr Ser Ile Glu Lys
            420                 425                 430

Leu Lys Tyr Ala Ile Leu Gln Gly Lys Gln Ile Asn Tyr Lys Ile Lys
            435                 440                 445

Asp Asp Ile Tyr Tyr Ile Leu Lys Asn Ala Tyr Ala Lys Tyr Phe Lys
        450                 455                 460

Ile Asp Val Tyr Lys Lys Gly Lys Leu Leu Tyr Pro Thr Leu Tyr Tyr
465                 470                 475                 480

His Arg Asn Ala Phe Ile Lys Ser Phe Val Val Glu Phe Phe Asn Asn
                485                 490                 495

Asn Lys Val Cys Glu Asn Thr Lys Cys Pro Leu Asn Ser Asn Cys Tyr
            500                 505                 510

Val Ile Asp Asp Glu Glu Thr Cys Arg Cys Leu Pro Gly Phe Asn Asn
        515                 520                 525

Ile Lys Ile Asp Asp Glu Met Asn Cys Val Arg Asp Asp Thr Leu Asp
        530                 535                 540

Cys Ser Arg Asn Asn Gly Gly Cys Asp Ile His Ala Lys Cys Ser Phe
545                 550                 555                 560

Ile Asn Lys Gln Ile Val Cys Glu Cys Lys Asp Lys Phe Glu Gly Asp
                565                 570                 575

Gly Ile Tyr Cys Ser Tyr Ser Phe Phe Ser Ser Ile His Asn Phe Ile
            580                 585                 590

Phe Phe Phe Ile Leu Cys Leu Phe Ile Phe Ile Leu
            595                 600

<210> SEQ ID NO 5
<211> LENGTH: 1464
<212> TYPE: DNA
<213> ORGANISM: Plasmodium vivax
<220> FEATURE:
<221> NAME/KEY: CDS
<222> LOCATION: (1)..(1464)
<220> FEATURE:
<221> NAME/KEY: sig_peptide
<222> LOCATION: (1)..(63)
<220> FEATURE:
<221> NAME/KEY: misc_feature
<222> LOCATION: (1390)..(1392)
<223> OTHER INFORMATION: predicted GPI-attachment site in encoded
      protein

<400> SEQUENCE: 5 atg agg aaa aac gcg caa ata gta att ttc tgc ctg ttc gga ttg ctg        48
Met Arg Lys Asn Ala Gln Ile Val Ile Phe Cys Leu Phe Gly Leu Leu
1               5                   10                  15 agt tat aga tgc gga gct gaa gga aac gtt agc cca ccc aac ttt aat        96
Ser Tyr Arg Cys Gly Ala Glu Gly Asn Val Ser Pro Pro Asn Phe Asn
            20                  25                  30 gac aac agg gta aac ggc aac aat gga aat aaa ggc aac gga aat gac       144
Asp Asn Arg Val Asn Gly Asn Asn Gly Asn Lys Gly Asn Gly Asn Asp
        35                  40                  45 aac gac gtg ccg tcg ttc att gga gga aac aat aat aac gtg aac gac       192
Asn Asp Val Pro Ser Phe Ile Gly Gly Asn Asn Asn Asn Val Asn Asp
    50                  55                  60 aat aat gat gat aac att ttt aat aaa aat gga aag gat gtc acc cga       240
Asn Asn Asp Asp Asn Ile Phe Asn Lys Asn Gly Lys Asp Val Thr Arg
65                  70                  75                  80 aat gat ggc gat gca aag gat gga gaa aat cga aat aac aag aaa aac       288
Asn Asp Gly Asp Ala Lys Asp Gly Glu Asn Arg Asn Asn Lys Lys Asn
                85                  90                  95
```

-continued

| | | |
|---|---|---|
| gaa aat ggc agt ggc tcc aat gag aat aac tcc att gca aat gcg gac<br>Glu Asn Gly Ser Gly Ser Asn Glu Asn Asn Ser Ile Ala Asn Ala Asp<br>100 105 110 | | 336 |
| aat ggt agc ggc aaa tct gat gcg aat gcc aac caa att gat gag gat<br>Asn Gly Ser Gly Lys Ser Asp Ala Asn Ala Asn Gln Ile Asp Glu Asp<br>115 120 125 | | 384 |
| gga aat aaa atg gat gaa gca tct tta aag aaa atc ctc aaa att gta<br>Gly Asn Lys Met Asp Glu Ala Ser Leu Lys Lys Ile Leu Lys Ile Val<br>130 135 140 | | 432 |
| gac gaa atg gaa aat att caa gga ctg ctc gat gga gat tac agc att<br>Asp Glu Met Glu Asn Ile Gln Gly Leu Leu Asp Gly Asp Tyr Ser Ile<br>145 150 155 160 | | 480 |
| ttg gat aag tac agt gtc aaa tta gtt gat gaa gat gat gga gaa acg<br>Leu Asp Lys Tyr Ser Val Lys Leu Val Asp Glu Asp Asp Gly Glu Thr<br>165 170 175 | | 528 |
| aat aaa aga aaa atc att gga gaa tat gat ttg aaa atg tta aaa aat<br>Asn Lys Arg Lys Ile Ile Gly Glu Tyr Asp Leu Lys Met Leu Lys Asn<br>180 185 190 | | 576 |
| att tta ttg ttc aga gaa aaa att tcc cga gtt tgt gaa aat aaa tac<br>Ile Leu Leu Phe Arg Glu Lys Ile Ser Arg Val Cys Glu Asn Lys Tyr<br>195 200 205 | | 624 |
| aat aaa aat tta ccc gtc ttg tta aaa aaa tgc tca aat gtg gat gac<br>Asn Lys Asn Leu Pro Val Leu Leu Lys Lys Cys Ser Asn Val Asp Asp<br>210 215 220 | | 672 |
| ccc aaa ttg agt aaa tcc agg gaa aaa att aaa aaa gga tta gca aaa<br>Pro Lys Leu Ser Lys Ser Arg Glu Lys Ile Lys Lys Gly Leu Ala Lys<br>225 230 235 240 | | 720 |
| aat aat atg agc att gaa gat ttt gtg gta ggt ttg ttg gaa gat tta<br>Asn Asn Met Ser Ile Glu Asp Phe Val Val Gly Leu Leu Glu Asp Leu<br>245 250 255 | | 768 |
| ttt gag aaa att aat gaa cat ttt att aaa gac gat tca ttt gat ttg<br>Phe Glu Lys Ile Asn Glu His Phe Ile Lys Asp Asp Ser Phe Asp Leu<br>260 265 270 | | 816 |
| agt gac tat tta gcc gat ttc gag ctc atc aat tat ata att atg cac<br>Ser Asp Tyr Leu Ala Asp Phe Glu Leu Ile Asn Tyr Ile Ile Met His<br>275 280 285 | | 864 |
| gaa acg tcc gaa ttg atc gat gag ctt ttg aac ata ata gag tcc atg<br>Glu Thr Ser Glu Leu Ile Asp Glu Leu Leu Asn Ile Ile Glu Ser Met<br>290 295 300 | | 912 |
| aat ttc aga ttg gaa tcc gga tct ttg gag aaa atg gtt aaa tct gca<br>Asn Phe Arg Leu Glu Ser Gly Ser Leu Glu Lys Met Val Lys Ser Ala<br>305 310 315 320 | | 960 |
| gaa tca gga atg aac tta aat tgc aaa atg aag gaa gac ata att cac<br>Glu Ser Gly Met Asn Leu Asn Cys Lys Met Lys Glu Asp Ile Ile His<br>325 330 335 | | 1008 |
| tta ctt aag aaa tcc tcc gcc aaa ttt ttt aaa atc gaa att gac aga<br>Leu Leu Lys Lys Ser Ser Ala Lys Phe Phe Lys Ile Glu Ile Asp Arg<br>340 345 350 | | 1056 |
| aag acc aag atg ata tac cca gtg cag gct aca cac aaa ggt gcc aac<br>Lys Thr Lys Met Ile Tyr Pro Val Gln Ala Thr His Lys Gly Ala Asn<br>355 360 365 | | 1104 |
| atg aaa caa ctc gcc ctg agc ttc ctc cag aag aac aat gta tgt gaa<br>Met Lys Gln Leu Ala Leu Ser Phe Leu Gln Lys Asn Asn Val Cys Glu<br>370 375 380 | | 1152 |
| cat aaa aag tgc cca ttg aac tcc aac tgc tat gtt ata aat gga gag<br>His Lys Lys Cys Pro Leu Asn Ser Asn Cys Tyr Val Ile Asn Gly Glu<br>385 390 395 400 | | 1200 |
| gag gtc tgc aga tgt cta ccc gga ttt agc ggc gtc aaa att gat aac<br>Glu Val Cys Arg Cys Leu Pro Gly Phe Ser Gly Val Lys Ile Asp Asn<br>405 410 415 | | 1248 |

-continued

```
gtg atg aac tgc gtt agg gat gat acc ctt gac tgt agc aac aac aac    1296
Val Met Asn Cys Val Arg Asp Asp Thr Leu Asp Cys Ser Asn Asn Asn
    420                 425                 430 ggt ggc tgt gat gtg aac gca acg tgt acc ctt ata gac aaa aaa att    1344
Gly Gly Cys Asp Val Asn Ala Thr Cys Thr Leu Ile Asp Lys Lys Ile
435                 440                 445 gtg tgt gaa tgc aag gac aac ttt gag gga ggc gga ata tac tgc tcc    1392
Val Cys Glu Cys Lys Asp Asn Phe Glu Gly Gly Gly Ile Tyr Cys Ser
    450                 455                 460 tac agc att ttc aac tcc atc aac aat ttc att ttc ctg atc ttg ttg    1440
Tyr Ser Ile Phe Asn Ser Ile Asn Asn Phe Ile Phe Leu Ile Leu Leu
465                 470                 475                 480 ctt ttg tgc ctg tac ctg ttc tag                                    1464
Leu Leu Cys Leu Tyr Leu Phe
                485

<210> SEQ ID NO 6
<211> LENGTH: 487
<212> TYPE: PRT
<213> ORGANISM: Plasmodium vivax

<400> SEQUENCE: 6

Met Arg Lys Asn Ala Gln Ile Val Ile Phe Cys Leu Phe Gly Leu Leu
1               5                   10                  15

Ser Tyr Arg Cys Gly Ala Glu Gly Asn Val Ser Pro Pro Asn Phe Asn
            20                  25                  30

Asp Asn Arg Val Asn Gly Asn Gly Asn Lys Gly Asn Gly Asn Asp
        35                  40                  45

Asn Asp Val Pro Ser Phe Ile Gly Asn Asn Asn Val Asn Asp
    50                  55                  60

Asn Asn Asp Asp Asn Ile Phe Asn Lys Asn Gly Lys Asp Val Thr Arg
65                  70                  75                  80

Asn Asp Gly Asp Ala Lys Asp Gly Glu Asn Arg Asn Asn Lys Lys Asn
                85                  90                  95

Glu Asn Gly Ser Gly Ser Asn Glu Asn Asn Ser Ile Ala Asn Ala Asp
            100                 105                 110

Asn Gly Ser Gly Lys Ser Asp Ala Asn Ala Asn Gln Ile Asp Glu Asp
        115                 120                 125

Gly Asn Lys Met Asp Glu Ala Ser Leu Lys Lys Ile Leu Lys Ile Val
    130                 135                 140

Asp Glu Met Glu Asn Ile Gln Gly Leu Leu Asp Gly Asp Tyr Ser Ile
145                 150                 155                 160

Leu Asp Lys Tyr Ser Val Lys Leu Val Asp Glu Asp Gly Glu Thr
                165                 170                 175

Asn Lys Arg Lys Ile Ile Gly Glu Tyr Asp Leu Lys Met Leu Lys Asn
            180                 185                 190

Ile Leu Leu Phe Arg Glu Lys Ile Ser Arg Val Cys Glu Asn Lys Tyr
        195                 200                 205

Asn Lys Asn Leu Pro Val Leu Leu Lys Lys Cys Ser Asn Val Asp Asp
    210                 215                 220

Pro Lys Leu Ser Lys Ser Arg Glu Lys Ile Lys Lys Gly Leu Ala Lys
225                 230                 235                 240

Asn Asn Met Ser Ile Glu Asp Phe Val Val Gly Leu Leu Glu Asp Leu
                245                 250                 255

Phe Glu Lys Ile Asn Glu His Phe Ile Lys Asp Asp Ser Phe Asp Leu
            260                 265                 270
```

-continued

```
Ser Asp Tyr Leu Ala Asp Phe Glu Leu Ile Asn Tyr Ile Ile Met His
        275                 280                 285
Glu Thr Ser Glu Leu Ile Asp Glu Leu Leu Asn Ile Ile Glu Ser Met
290                 295                 300
Asn Phe Arg Leu Glu Ser Gly Ser Leu Glu Lys Met Val Lys Ser Ala
305                 310                 315                 320
Glu Ser Gly Met Asn Leu Asn Cys Lys Met Lys Glu Asp Ile Ile His
                325                 330                 335
Leu Leu Lys Lys Ser Ser Ala Lys Phe Phe Lys Ile Glu Ile Asp Arg
            340                 345                 350
Lys Thr Lys Met Ile Tyr Pro Val Gln Ala Thr His Lys Gly Ala Asn
        355                 360                 365
Met Lys Gln Leu Ala Leu Ser Phe Leu Gln Lys Asn Asn Val Cys Glu
370                 375                 380
His Lys Lys Cys Pro Leu Asn Ser Asn Cys Tyr Val Ile Asn Gly Glu
385                 390                 395                 400
Glu Val Cys Arg Cys Leu Pro Gly Phe Ser Gly Val Lys Ile Asp Asn
                405                 410                 415
Val Met Asn Cys Val Arg Asp Asp Thr Leu Asp Cys Ser Asn Asn
            420                 425                 430
Gly Gly Cys Asp Val Asn Ala Thr Cys Thr Leu Ile Asp Lys Lys Ile
        435                 440                 445
Val Cys Glu Cys Lys Asp Asn Phe Glu Gly Gly Ile Tyr Cys Ser
450                 455                 460
Tyr Ser Ile Phe Asn Ser Ile Asn Asn Phe Ile Phe Leu Ile Leu Leu
465                 470                 475                 480
Leu Leu Cys Leu Tyr Leu Phe
                485

<210> SEQ ID NO 7
<211> LENGTH: 5774
<212> TYPE: DNA
<213> ORGANISM: Plasmodium yoelii
<220> FEATURE:
<221> NAME/KEY: CDS
<222> LOCATION: (189)..(5507)
<220> FEATURE:
<221> NAME/KEY: sig_peptide
<222> LOCATION: (189)..(245)
<220> FEATURE:
<221> NAME/KEY: misc_feature
<222> LOCATION: (5451)..(5507)
<223> OTHER INFORMATION: predicted membrane anchor sequence

<400> SEQUENCE: 7
tatatattat atgtaattag tatatgtata tatatttgga acattataa atgatataac      60 aaaactttaa tatttatttt tacacaaatt agtactatta taaaatgcaa agtaatgta    120 catttgtgtg tattaacttt agcataataa aatattccac tctgtatatt agttaagttt   180 agttgaaa atg aag gtg att gga ctt tta ttt tct ttc gtt ttt ttt gct    230
         Met Lys Val Ile Gly Leu Leu Phe Ser Phe Val Phe Phe Ala
          1               5                  10 ata aaa tgc aaa tct gaa aca att gaa gtt tat aat gat ctc att caa    278
Ile Lys Cys Lys Ser Glu Thr Ile Glu Val Tyr Asn Asp Leu Ile Gln
15              20                  25                  30 aag tta gaa aaa tta gaa tca ttg tca gtg gat ggg tta gaa cta ttt    326
Lys Leu Glu Lys Leu Glu Ser Leu Ser Val Asp Gly Leu Glu Leu Phe
            35                  40                  45 caa aaa agt caa gta att ata aat gca aca caa cca act gaa act att    374
Gln Lys Ser Gln Val Ile Ile Asn Ala Thr Gln Pro Thr Glu Thr Ile
```

```
                50                   55                   60
gat cca ttt aca aat cat aac ttt gca caa caa gta caa gat ttt gtt     422
Asp Pro Phe Thr Asn His Asn Phe Ala Gln Gln Val Gln Asp Phe Val
         65                   70                   75 aca aaa ttt gaa gga tta gga ttt aca gaa caa aca gaa tta gtc aat     470
Thr Lys Phe Glu Gly Leu Gly Phe Thr Glu Gln Thr Glu Leu Val Asn
 80                   85                   90 tta ata aaa gca tta acc cca aat aga tat gga gta aaa tat tta att     518
Leu Ile Lys Ala Leu Thr Pro Asn Arg Tyr Gly Val Lys Tyr Leu Ile
 95                  100                  105                  110 gaa agt aaa gaa gaa ttt aat gga tta atg cac gca ata aat ttt tat     566
Glu Ser Lys Glu Glu Phe Asn Gly Leu Met His Ala Ile Asn Phe Tyr
                    115                  120                  125 tat gat gta ctt aga gat aaa tta aat gat atg tgt gca aat aat tat     614
Tyr Asp Val Leu Arg Asp Lys Leu Asn Asp Met Cys Ala Asn Asn Tyr
        130                  135                  140 tgt gaa att cct gaa cat ctt aaa att agt gaa gaa gaa aca gaa atg     662
Cys Glu Ile Pro Glu His Leu Lys Ile Ser Glu Glu Glu Thr Glu Met
            145                  150                  155 ctt aaa aaa gta att tta ggt tat aga aaa cca ata gaa aat att caa     710
Leu Lys Lys Val Ile Leu Gly Tyr Arg Lys Pro Ile Glu Asn Ile Gln
160                  165                  170 gac gat att gaa aag tta gaa att tac ata gaa aga aat aaa gaa act     758
Asp Asp Ile Glu Lys Leu Glu Ile Tyr Ile Glu Arg Asn Lys Glu Thr
175                  180                  185                  190 gtt gca gct tta aac gct ctt att gct gaa gaa aca aaa aaa ata caa     806
Val Ala Ala Leu Asn Ala Leu Ile Ala Glu Glu Thr Lys Lys Ile Gln
                    195                  200                  205 cct gaa ggt aac gaa gat tgc aat gac gct agt tgt gat agc gat aaa     854
Pro Glu Gly Asn Glu Asp Cys Asn Asp Ala Ser Cys Asp Ser Asp Lys
        210                  215                  220 tat aat aaa aaa aaa cca ata tac caa gct atg tac aat gtt ata ttt     902
Tyr Asn Lys Lys Lys Pro Ile Tyr Gln Ala Met Tyr Asn Val Ile Phe
            225                  230                  235 tac aaa aaa caa tta gct gaa ata caa aag gtt gtc gaa gtc tta gaa     950
Tyr Lys Lys Gln Leu Ala Glu Ile Gln Lys Val Val Glu Val Leu Glu
240                  245                  250 aaa cga gtt tct aca tta aag aaa aat gat gcc atc aaa cca tta tgg     998
Lys Arg Val Ser Thr Leu Lys Lys Asn Asp Ala Ile Lys Pro Leu Trp
255                  260                  265                  270 caa caa att gaa gtt ctc aat gct gcc ccc gtc gtc act gcc gaa aca    1046
Gln Gln Ile Glu Val Leu Asn Ala Ala Pro Val Val Thr Ala Glu Thr
                    275                  280                  285 caa ata gtt aca gga gga caa tct agt aca gaa cca ggt agt ggt gga    1094
Gln Ile Val Thr Gly Gly Gln Ser Ser Thr Glu Pro Gly Ser Gly Gly
        290                  295                  300 tca agt gca tcg gga aca agt tca tca gga caa gct agt gca gga aca    1142
Ser Ser Ala Ser Gly Thr Ser Ser Ser Gly Gln Ala Ser Ala Gly Thr
            305                  310                  315 ggt gta gaa caa gct aac act gta gca tct gtt aca gta aca cct agt    1190
Gly Val Glu Gln Ala Asn Thr Val Ala Ser Val Thr Val Thr Pro Ser
320                  325                  330 gta gga caa aat ggt gaa gca tca act aat cca caa aca gct caa gtg    1238
Val Gly Gln Asn Gly Glu Ala Ser Thr Asn Pro Gln Thr Ala Gln Val
335                  340                  345                  350 caa ccc gtt cca act ctt aca tta gaa gaa aaa cag aaa aaa ata gcc    1286
Gln Pro Val Pro Thr Leu Thr Leu Glu Glu Lys Gln Lys Lys Ile Ala
                    355                  360                  365 gga ctt tat gct caa att aaa gaa att gca aaa act ata aaa ttc aac    1334
Gly Leu Tyr Ala Gln Ile Lys Glu Ile Ala Lys Thr Ile Lys Phe Asn
```

```
                  370                 375                 380
tta gaa gga ata ttt gta gat cca atc gaa tta gaa tat ttc aaa aaa    1382
Leu Glu Gly Ile Phe Val Asp Pro Ile Glu Leu Glu Tyr Phe Lys Lys
        385                 390                 395 gaa aaa aaa aaa gaa agt tgc aat tta tca act tca tcc tgt aaa aaa    1430
Glu Lys Lys Lys Glu Ser Cys Asn Leu Ser Thr Ser Ser Cys Lys Lys
400                 405                 410 aat aaa gca tcc gaa act ata ata cca tta act ata cgt tat cca aat    1478
Asn Lys Ala Ser Glu Thr Ile Ile Pro Leu Thr Ile Arg Tyr Pro Asn
415                 420                 425                 430 ggt att agt tac cca tta cct gaa aat gat gtt tac aat aaa att gcc    1526
Gly Ile Ser Tyr Pro Leu Pro Glu Asn Asp Val Tyr Asn Lys Ile Ala
                435                 440                 445 aat aat gcc gct gaa aca aca tat ggt gat ttg aca cat ccc gat aat    1574
Asn Asn Ala Ala Glu Thr Thr Tyr Gly Asp Leu Thr His Pro Asp Asn
            450                 455                 460 aca cca tta aca gga gat tta gcc aca aat gaa caa gcc aga aaa gat    1622
Thr Pro Leu Thr Gly Asp Leu Ala Thr Asn Glu Gln Ala Arg Lys Asp
        465                 470                 475 cta ata aaa gct att aaa aag aaa ata aaa gca gaa gaa aaa aaa tta    1670
Leu Ile Lys Ala Ile Lys Lys Lys Ile Lys Ala Glu Glu Lys Lys Leu
480                 485                 490 gaa aca tta aaa acg aat tat gat aat aaa ctt aca gaa ttt aat caa    1718
Glu Thr Leu Lys Thr Asn Tyr Asp Asn Lys Leu Thr Glu Phe Asn Gln
495                 500                 505                 510 caa aaa act cca ttc aaa gaa gca gct aaa gaa ttt tat gaa tca aaa    1766
Gln Lys Thr Pro Phe Lys Glu Ala Ala Lys Glu Phe Tyr Glu Ser Lys
                515                 520                 525 ttt aga aat aaa ttg act tct gaa att ttt gaa aaa ttc aaa aca aaa    1814
Phe Arg Asn Lys Leu Thr Ser Glu Ile Phe Glu Lys Phe Lys Thr Lys
            530                 535                 540 aga gat gaa tat atg acc aag aaa acc gaa tta aac act tgt gaa tat    1862
Arg Asp Glu Tyr Met Thr Lys Lys Thr Glu Leu Asn Thr Cys Glu Tyr
        545                 550                 555 gga aat act aaa gaa tta att aat aaa tta aat aaa caa ctt aat tat    1910
Gly Asn Thr Lys Glu Leu Ile Asn Lys Leu Asn Lys Gln Leu Asn Tyr
560                 565                 570 tta caa gat tat tca tta aga aaa gat ata att agt aat gaa att gaa    1958
Leu Gln Asp Tyr Ser Leu Arg Lys Asp Ile Ile Ser Asn Glu Ile Glu
575                 580                 585                 590 tat ttt tca aat aaa aaa aaa gaa tta caa tat aat att aat aga tta    2006
Tyr Phe Ser Asn Lys Lys Lys Glu Leu Gln Tyr Asn Ile Asn Arg Leu
                595                 600                 605 gca gaa gct gtt caa gca aaa caa aat gta tta gtt gca tca aaa gat    2054
Ala Glu Ala Val Gln Ala Lys Gln Asn Val Leu Val Ala Ser Lys Asp
            610                 615                 620 gta cca ctt tca aca ctt gta gaa ttg caa ata caa aaa tct tta tta    2102
Val Pro Leu Ser Thr Leu Val Glu Leu Gln Ile Gln Lys Ser Leu Leu
        625                 630                 635 aca aaa caa att gag caa tta aat aaa act gaa gta tct tta aac aaa    2150
Thr Lys Gln Ile Glu Gln Leu Asn Lys Thr Glu Val Ser Leu Asn Lys
640                 645                 650 gct caa tta aaa gac aaa cta tat gtt cca aaa aca tac ggt aat gaa    2198
Ala Gln Leu Lys Asp Lys Leu Tyr Val Pro Lys Thr Tyr Gly Asn Glu
655                 660                 665                 670 gga aaa cca gaa cca tac tat tta ata gct gta aaa aaa gaa gtt gac    2246
Gly Lys Pro Glu Pro Tyr Tyr Leu Ile Ala Val Lys Lys Glu Val Asp
                675                 680                 685 aga ctt gcc caa ttt att cca aaa atc gaa agt atg att gct aaa gag    2294
Arg Leu Ala Gln Phe Ile Pro Lys Ile Glu Ser Met Ile Ala Lys Glu
```

-continued

```
             690                 695                 700
aag gaa aga atg gaa caa gga cct gca att act gga gaa tct gaa gaa    2342
Lys Glu Arg Met Glu Gln Gly Pro Ala Ile Thr Gly Glu Ser Glu Glu
        705                 710                 715 gta cca tct ggc cct agt gct gaa tca tca aca gat aga tca aca caa    2390
Val Pro Ser Gly Pro Ser Ala Glu Ser Ser Thr Asp Arg Ser Thr Gln
720                 725                 730 tct tca aca tcc tca tcc tca tcc tca tct tca acc cca gca gca gca    2438
Ser Ser Thr Ser Ser Ser Ser Ser Ser Ser Thr Pro Ala Ala Ala
735                 740                 745                 750 gaa tcc tcc tca gcc aca tta cca gaa gca ccc gca cca gca gaa gca    2486
Glu Ser Ser Ser Ala Thr Leu Pro Glu Ala Pro Ala Pro Ala Glu Ala
                755                 760                 765 gca tcc cca tca aca gaa gca tca gaa gaa aca aca ata ccc cct acc    2534
Ala Ser Pro Ser Thr Glu Ala Ser Glu Glu Thr Thr Ile Pro Pro Thr
            770                 775                 780 aca caa gaa aca caa cca tca caa gct gca tca tcc aca aca cct gca    2582
Thr Gln Glu Thr Gln Pro Ser Gln Ala Ala Ser Ser Thr Thr Pro Ala
        785                 790                 795 aaa cca gtt atg aca aaa tta tat tat ctt gaa aaa tta caa aaa ttt    2630
Lys Pro Val Met Thr Lys Leu Tyr Tyr Leu Glu Lys Leu Gln Lys Phe
800                 805                 810 tta gta ttc tca tat tca tgc cat aaa tac gtt tta cta caa aac tct    2678
Leu Val Phe Ser Tyr Ser Cys His Lys Tyr Val Leu Leu Gln Asn Ser
815                 820                 825                 830 acc ata aac aaa gat gct tta agc aaa tat gct ctt aca tct gaa gaa    2726
Thr Ile Asn Lys Asp Ala Leu Ser Lys Tyr Ala Leu Thr Ser Glu Glu
                835                 840                 845 gat aaa ata aga aca tta aaa aga tgc agt gaa tta gat gta tta tta    2774
Asp Lys Ile Arg Thr Leu Lys Arg Cys Ser Glu Leu Asp Val Leu Leu
            850                 855                 860 gct att caa aat aat atg cct act atg tat tca ctt tat gaa agt ata    2822
Ala Ile Gln Asn Asn Met Pro Thr Met Tyr Ser Leu Tyr Glu Ser Ile
        865                 870                 875 gtt gat ggt tta caa aac att tat act gaa tta tat gaa aaa gaa atg    2870
Val Asp Gly Leu Gln Asn Ile Tyr Thr Glu Leu Tyr Glu Lys Glu Met
880                 885                 890 atg tat cat ata tat aaa tta aaa gat gaa aac cca tct att aaa tct    2918
Met Tyr His Ile Tyr Lys Leu Lys Asp Glu Asn Pro Ser Ile Lys Ser
895                 900                 905                 910 tta ttg gta aaa gct ggc gtc att gaa cca gaa cca gta gca gca cca    2966
Leu Leu Val Lys Ala Gly Val Ile Glu Pro Glu Pro Val Ala Ala Pro
                915                 920                 925 aca cca gta act cca gca gca aca gaa caa caa caa caa caa gca aca    3014
Thr Pro Val Thr Pro Ala Ala Thr Glu Gln Gln Gln Gln Gln Ala Thr
            930                 935                 940 cct gat gta caa tca gat gca cca gca cca tca gat gtc tcg caa caa    3062
Pro Asp Val Gln Ser Asp Ala Pro Ala Pro Ser Asp Val Ser Gln Gln
        945                 950                 955 cca gaa aca cca gta aca tcc acg aca cca gag gta aca acc tca aca    3110
Pro Glu Thr Pro Val Thr Ser Thr Thr Pro Glu Val Thr Thr Ser Thr
960                 965                 970 gaa gca tca tca tca gca cct ggc gaa ggt aca cca tca gga gaa gca    3158
Glu Ala Ser Ser Ser Ala Pro Gly Glu Gly Thr Pro Ser Gly Glu Ala
975                 980                 985                 990 gga gca tca gga aca gaa gga gca aca gca tct aac gca gcc aca cca    3206
Gly Ala Ser Gly Thr Glu Gly Ala Thr Ala Ser Asn Ala Ala Thr Pro
                995                 1000                1005 gca gga aca tca gca tca gga tca gca gca tct aac gca agt aca         3251
Ala Gly Thr Ser Ala Ser Gly Ser Ala Ala Ser Asn Ala Ser Thr
```

-continued

|  |  |  |  |
|---|---|---|---|
| | 1010 | 1015 | 1020 |
| acc tca gat gta aca ccc cca gca gca gcg gca gca gta cca tca<br>Thr Ser Asp Val Thr Pro Pro Ala Ala Ala Ala Ala Val Pro Ser<br>1025                   1030                  1035 | | | 3296 |
| aca tct aca cca gca cct gca caa cca cca gca gca aat tct caa<br>Thr Ser Thr Pro Ala Pro Ala Gln Pro Pro Ala Ala Asn Ser Gln<br>1040                   1045                  1050 | | | 3341 |
| tca gga aac cct gac tca ggt att aga tca cga gca gaa agt gaa<br>Ser Gly Asn Pro Asp Ser Gly Ile Arg Ser Arg Ala Glu Ser Glu<br>1055                   1060                  1065 | | | 3386 |
| gag gat atg cct gcc gat gat ttt gaa tta gac aat tta tac aaa<br>Glu Asp Met Pro Ala Asp Asp Phe Glu Leu Asp Asn Leu Tyr Lys<br>1070                   1075                  1080 | | | 3431 |
| tct tac tta caa caa att gat gga aat aat act gaa ttc ata aat<br>Ser Tyr Leu Gln Gln Ile Asp Gly Asn Asn Thr Glu Phe Ile Asn<br>1085                   1090                  1095 | | | 3476 |
| ttt ata aaa tct aaa aaa gaa tta ata aaa gca ttg aca cct gaa<br>Phe Ile Lys Ser Lys Lys Glu Leu Ile Lys Ala Leu Thr Pro Glu<br>1100                   1105                  1110 | | | 3521 |
| aaa gtt aat caa tta tat ctt gaa atc gct cac tta aag gaa tta<br>Lys Val Asn Gln Leu Tyr Leu Glu Ile Ala His Leu Lys Glu Leu<br>1115                   1120                  1125 | | | 3566 |
| tca gaa cat tat tat gat cgt tat tct aca tat aaa tta aaa tta<br>Ser Glu His Tyr Tyr Asp Arg Tyr Ser Thr Tyr Lys Leu Lys Leu<br>1130                   1135                  1140 | | | 3611 |
| gaa aga tta tat aac aaa cat gaa caa att caa cta acc aat cga<br>Glu Arg Leu Tyr Asn Lys His Glu Gln Ile Gln Leu Thr Asn Arg<br>1145                   1150                  1155 | | | 3656 |
| caa att aga gat ctt agt ata ttg aaa gca cga tta tta aaa aga<br>Gln Ile Arg Asp Leu Ser Ile Leu Lys Ala Arg Leu Leu Lys Arg<br>1160                   1165                  1170 | | | 3701 |
| aaa caa act ctt aat ggc gta ttt tat ata tta aat ggt tat gta<br>Lys Gln Thr Leu Asn Gly Val Phe Tyr Ile Leu Asn Gly Tyr Val<br>1175                   1180                  1185 | | | 3746 |
| aat ttc ttt aac aag aga aga gaa gct gaa aaa caa tat gta gat<br>Asn Phe Phe Asn Lys Arg Arg Glu Ala Glu Lys Gln Tyr Val Asp<br>1190                   1195                  1200 | | | 3791 |
| aat gca tta aaa aat act gat atg tta tta aaa tac tac aaa gct<br>Asn Ala Leu Lys Asn Thr Asp Met Leu Leu Lys Tyr Tyr Lys Ala<br>1205                   1210                  1215 | | | 3836 |
| cgt act aaa tat ttt act tct gaa gct gtt cct tta aaa aca tta<br>Arg Thr Lys Tyr Phe Thr Ser Glu Ala Val Pro Leu Lys Thr Leu<br>1220                   1225                  1230 | | | 3881 |
| tct aaa gca tca ctt gac aga gaa tcc aat tat ttg aaa atc gaa<br>Ser Lys Ala Ser Leu Asp Arg Glu Ser Asn Tyr Leu Lys Ile Glu<br>1235                   1240                  1245 | | | 3926 |
| aaa ttc aga gca tac agt cga tta gaa tta aga tta aaa aaa aat<br>Lys Phe Arg Ala Tyr Ser Arg Leu Glu Leu Arg Leu Lys Lys Asn<br>1250                   1255                  1260 | | | 3971 |
| att aat tta gga aag gaa aga att tca tat gta tca gga ggt tta<br>Ile Asn Leu Gly Lys Glu Arg Ile Ser Tyr Val Ser Gly Gly Leu<br>1265                   1270                  1275 | | | 4016 |
| cac cac gta ttt gaa gaa ttt aaa gaa ctt ata aaa gat aaa gac<br>His His Val Phe Glu Glu Phe Lys Glu Leu Ile Lys Asp Lys Asp<br>1280                   1285                  1290 | | | 4061 |
| tat acc gga aaa aaa aac cct gat aat gcc cct gaa gtt acc aat<br>Tyr Thr Gly Lys Lys Asn Pro Asp Asn Ala Pro Glu Val Thr Asn<br>1295                   1300                  1305 | | | 4106 |
| gca ttc gaa caa tat aaa gaa ttg ctt cca aag gga gta aca gtt<br>Ala Phe Glu Gln Tyr Lys Glu Leu Leu Pro Lys Gly Val Thr Val | | | 4151 |

-continued

|     |     |     | 1310 |     |     |     | 1315 |     |     |     | 1320 |     |      |
|-----|-----|-----|------|-----|-----|-----|------|-----|-----|-----|------|-----|------|
| tca | act | cca | gca  | gtc | gca | gtt | aca  | acg | aca | cta | gca  | gct | gac  | gca |      |
| Ser | Thr | Pro | Ala  | Val | Ala | Val | Thr  | Thr | Thr | Leu | Ala  | Ala | Asp  | Ala | 4196 |
|     |     |     | 1325 |     |     |     | 1330 |     |     |     | 1335 |     |      |

| cca | gca | aca | cca  | gaa | gga | gca | gta  | cca | gga | gca | gta  | cca | gga  | gct |      |
|-----|-----|-----|------|-----|-----|-----|------|-----|-----|-----|------|-----|------|-----|------|
| Pro | Ala | Thr | Pro  | Glu | Gly | Ala | Val  | Pro | Gly | Ala | Val  | Pro | Gly  | Ala | 4241 |
|     |     |     | 1340 |     |     |     | 1345 |     |     |     | 1350 |     |      | gta cca ggt gca gta cca gga gca gta cca ggt gca gta cca gga      4286
Val Pro Gly Ala Val Pro Gly Ala Val Pro Gly Ala Val Pro Gly
            1355                1360                1365 tca gga acc gat aca cgg gta gct gga agc agt gtt gat gat aat      4331
Ser Gly Thr Asp Thr Arg Val Ala Gly Ser Ser Val Asp Asp Asn
            1370                1375                1380 gaa gac gat gat ata tat caa att gca agt ggt caa tcc gaa gat      4376
Glu Asp Asp Asp Ile Tyr Gln Ile Ala Ser Gly Gln Ser Glu Asp
            1385                1390                1395 gca cca gaa aaa gat att ctt tcc gaa ttt aca aat gaa agt ttg      4421
Ala Pro Glu Lys Asp Ile Leu Ser Glu Phe Thr Asn Glu Ser Leu
            1400                1405                1410 tat gta tac aca aaa agg ttg ggt agt aca tat aaa tca tta aag      4466
Tyr Val Tyr Thr Lys Arg Leu Gly Ser Thr Tyr Lys Ser Leu Lys
            1415                1420                1425 aaa cac atg tta aga gaa ttt tca aca att aaa gaa gac atg aca      4511
Lys His Met Leu Arg Glu Phe Ser Thr Ile Lys Glu Asp Met Thr
            1430                1435                1440 aat gga tta aat aat aaa tca caa aaa aga aat gat ttc ctt gaa      4556
Asn Gly Leu Asn Asn Lys Ser Gln Lys Arg Asn Asp Phe Leu Glu
            1445                1450                1455 gta tta agc cat gaa tta gat tta ttc aaa gat tta agt acc aac      4601
Val Leu Ser His Glu Leu Asp Leu Phe Lys Asp Leu Ser Thr Asn
            1460                1465                1470 aaa tat gtt att aga aat cca tat caa tta tta gat aat gat aaa      4646
Lys Tyr Val Ile Arg Asn Pro Tyr Gln Leu Leu Asp Asn Asp Lys
            1475                1480                1485 aaa gac aaa caa ata gta aac tta aaa tat gct act aaa ggt ata      4691
Lys Asp Lys Gln Ile Val Asn Leu Lys Tyr Ala Thr Lys Gly Ile
            1490                1495                1500 aat gaa gat ata gaa aca act act gac gga att aaa ttc ttt aac      4736
Asn Glu Asp Ile Glu Thr Thr Thr Asp Gly Ile Lys Phe Phe Asn
            1505                1510                1515 aaa atg gtt gaa tta tac aac act caa tta gct gca gta aag gaa      4781
Lys Met Val Glu Leu Tyr Asn Thr Gln Leu Ala Ala Val Lys Glu
            1520                1525                1530 caa att gct acc ata gaa gct gaa act aac gat acc aat aaa gaa      4826
Gln Ile Ala Thr Ile Glu Ala Glu Thr Asn Asp Thr Asn Lys Glu
            1535                1540                1545 gaa aaa aag aaa tat att cca atc ctt gaa gat ctt aaa gga tta      4871
Glu Lys Lys Lys Tyr Ile Pro Ile Leu Glu Asp Leu Lys Gly Leu
            1550                1555                1560 tat gaa acc gta ata ggt caa gca gaa gaa tat tca gaa gaa tta      4916
Tyr Glu Thr Val Ile Gly Gln Ala Glu Glu Tyr Ser Glu Glu Leu
            1565                1570                1575 caa aat aga ctt gat aat tat aaa aat gaa aaa gct gaa ttt gaa      4961
Gln Asn Arg Leu Asp Asn Tyr Lys Asn Glu Lys Ala Glu Phe Glu
            1580                1585                1590 ata tta aca aaa aat tta gaa aaa tac ata caa att gac gaa aaa      5006
Ile Leu Thr Lys Asn Leu Glu Lys Tyr Ile Gln Ile Asp Glu Lys
            1595                1600                1605 ctt gac gaa ttt gta gaa cat gca gaa aat aat aaa cac ata gcc      5051
Leu Asp Glu Phe Val Glu His Ala Glu Asn Asn Lys His Ile Ala

```
                      1610                  1615                  1620
tca  ata  gct  tta  aac  aac  tta  aat  aaa  tct  ggt  tta  gta  gga  gaa      5096
Ser  Ile  Ala  Leu  Asn  Asn  Leu  Asn  Lys  Ser  Gly  Leu  Val  Gly  Glu
          1625                      1630                     1635 ggt  gaa  tca  aag  aaa  ata  tta  gca  aaa  atg  ctt  aac  atg  gat  ggt      5141
Gly  Glu  Ser  Lys  Lys  Ile  Leu  Ala  Lys  Met  Leu  Asn  Met  Asp  Gly
          1640                     1645                      1650 atg  gat  tta  tta  ggt  gta  gac  cct  aaa  cat  gta  tgt  gtt  gat  aca      5186
Met  Asp  Leu  Leu  Gly  Val  Asp  Pro  Lys  His  Val  Cys  Val  Asp  Thr
          1655                     1660                      1665 aga  gat  att  cct  aaa  aat  gct  gga  tgt  ttt  aga  gat  gat  aat  ggt      5231
Arg  Asp  Ile  Pro  Lys  Asn  Ala  Gly  Cys  Phe  Arg  Asp  Asp  Asn  Gly
          1670                     1675                      1680 act  gaa  gaa  tgg  aga  tgt  tta  tta  ggt  tac  aaa  aaa  ggt  gaa  ggt      5276
Thr  Glu  Glu  Trp  Arg  Cys  Leu  Leu  Gly  Tyr  Lys  Lys  Gly  Glu  Gly
          1685                     1690                      1695 aat  aca  tgt  gta  gaa  aat  aat  aat  cct  act  tgt  gat  atc  aac  aat      5321
Asn  Thr  Cys  Val  Glu  Asn  Asn  Asn  Pro  Thr  Cys  Asp  Ile  Asn  Asn
          1700                     1705                      1710 ggt  gga  tgt  gat  cca  act  gct  agt  tgt  caa  aat  gcg  gaa  agt  acg      5366
Gly  Gly  Cys  Asp  Pro  Thr  Ala  Ser  Cys  Gln  Asn  Ala  Glu  Ser  Thr
          1715                     1720                      1725 gaa  aat  tcc  aaa  aaa  att  ata  tgt  aca  tgt  aaa  gaa  cca  acc  cct      5411
Glu  Asn  Ser  Lys  Lys  Ile  Ile  Cys  Thr  Cys  Lys  Glu  Pro  Thr  Pro
          1730                     1735                      1740 aat  gca  tat  tat  gaa  ggt  gta  ttc  tgt  agt  tct  tcc  agc  ttt  atg      5456
Asn  Ala  Tyr  Tyr  Glu  Gly  Val  Phe  Cys  Ser  Ser  Ser  Ser  Phe  Met
          1745                     1750                      1755 gga  tta  tca  att  tta  tta  att  atc  aca  tta  att  gta  ttt  aat  ata      5501
Gly  Leu  Ser  Ile  Leu  Leu  Ile  Ile  Thr  Leu  Ile  Val  Phe  Asn  Ile
          1760                     1765                      1770 ttt  taa  ataaattatt  gaaatatttg  ttggattttg  ttttttcttt  atatatattt           5557
Phe taaaagttgt  atagtacatt  tgaaatatat  attctggcat  aaattgtata  tttttttaata         5617 taaaaaaaaa  aatatatat  aattttttaat  aaatatttt  aaataaatgt  atatgtatat           5677
agtgttagga  aattttgtat  gactttaaaa  tatgatacta  tttttttttt  aaactacata          5737
tatatatata  tgtatatata  agtaatgagc  ttatgaa                                     5774
```

<210> SEQ ID NO 8
<211> LENGTH: 1772
<212> TYPE: PRT
<213> ORGANISM: Plasmodium yoelii

<400> SEQUENCE: 8

Met Lys Val Ile Gly Leu Leu Phe Ser Phe Val Phe Phe Ala Ile Lys
1               5                   10                  15

Cys Lys Ser Glu Thr Ile Glu Val Tyr Asn Asp Leu Ile Gln Lys Leu
            20                  25                  30

Glu Lys Leu Glu Ser Leu Ser Val Asp Gly Leu Glu Leu Phe Gln Lys
        35                  40                  45

Ser Gln Val Ile Ile Asn Ala Thr Gln Pro Thr Glu Thr Ile Asp Pro
    50                  55                  60

Phe Thr Asn His Asn Phe Ala Gln Gln Val Gln Asp Phe Val Thr Lys
65                  70                  75                  80

Phe Glu Gly Leu Gly Phe Thr Glu Gln Thr Glu Leu Val Asn Leu Ile
                85                  90                  95

Lys Ala Leu Thr Pro Asn Arg Tyr Gly Val Lys Tyr Leu Ile Glu Ser

```
                 100                 105                 110
Lys Glu Glu Phe Asn Gly Leu Met His Ala Ile Asn Phe Tyr Tyr Asp
            115                 120                 125

Val Leu Arg Asp Lys Leu Asn Asp Met Cys Ala Asn Asn Tyr Cys Glu
130                 135                 140

Ile Pro Glu His Leu Lys Ile Ser Glu Glu Thr Glu Met Leu Lys
145                 150                 155                 160

Lys Val Ile Leu Gly Tyr Arg Lys Pro Ile Glu Asn Ile Gln Asp Asp
                165                 170                 175

Ile Glu Lys Leu Glu Ile Tyr Ile Glu Arg Asn Lys Glu Thr Val Ala
            180                 185                 190

Ala Leu Asn Ala Leu Ile Ala Glu Glu Thr Lys Lys Ile Gln Pro Glu
            195                 200                 205

Gly Asn Glu Asp Cys Asn Asp Ala Ser Cys Asp Ser Asp Lys Tyr Asn
210                 215                 220

Lys Lys Lys Pro Ile Tyr Gln Ala Met Tyr Asn Val Ile Phe Tyr Lys
225                 230                 235                 240

Lys Gln Leu Ala Glu Ile Gln Lys Val Val Glu Val Leu Glu Lys Arg
            245                 250                 255

Val Ser Thr Leu Lys Lys Asn Asp Ala Ile Lys Pro Leu Trp Gln Gln
            260                 265                 270

Ile Glu Val Leu Asn Ala Ala Pro Val Val Thr Ala Glu Thr Gln Ile
            275                 280                 285

Val Thr Gly Gly Gln Ser Ser Thr Glu Pro Gly Ser Gly Gly Ser Ser
            290                 295                 300

Ala Ser Gly Thr Ser Ser Ser Gly Gln Ala Ser Ala Gly Thr Gly Val
305                 310                 315                 320

Glu Gln Ala Asn Thr Val Ala Ser Val Thr Val Thr Pro Ser Val Gly
                325                 330                 335

Gln Asn Gly Glu Ala Ser Thr Asn Pro Gln Thr Ala Gln Val Gln Pro
            340                 345                 350

Val Pro Thr Leu Thr Leu Glu Glu Lys Gln Lys Lys Ile Ala Gly Leu
            355                 360                 365

Tyr Ala Gln Ile Lys Glu Ile Ala Lys Thr Ile Lys Phe Asn Leu Glu
            370                 375                 380

Gly Ile Phe Val Asp Pro Ile Glu Leu Glu Tyr Phe Lys Lys Glu Lys
385                 390                 395                 400

Lys Lys Glu Ser Cys Asn Leu Ser Thr Ser Ser Cys Lys Lys Asn Lys
                405                 410                 415

Ala Ser Glu Thr Ile Ile Pro Leu Thr Ile Arg Tyr Pro Asn Gly Ile
            420                 425                 430

Ser Tyr Pro Leu Pro Glu Asn Asp Val Tyr Asn Lys Ile Ala Asn Asn
            435                 440                 445

Ala Ala Glu Thr Thr Tyr Gly Asp Leu Thr His Pro Asp Asn Thr Pro
            450                 455                 460

Leu Thr Gly Asp Leu Ala Thr Asn Glu Gln Ala Arg Lys Asp Leu Ile
465                 470                 475                 480

Lys Ala Ile Lys Lys Ile Lys Ala Glu Glu Lys Lys Leu Glu Thr
                485                 490                 495

Leu Lys Thr Asn Tyr Asp Asn Lys Leu Thr Glu Phe Asn Gln Gln Lys
            500                 505                 510

Thr Pro Phe Lys Glu Ala Lys Glu Phe Tyr Glu Ser Lys Phe Arg
            515                 520                 525
```

-continued

Asn Lys Leu Thr Ser Glu Ile Phe Glu Lys Phe Lys Thr Lys Arg Asp
         530                 535                 540

Glu Tyr Met Thr Lys Lys Thr Glu Leu Asn Thr Cys Glu Tyr Gly Asn
545                 550                 555                 560

Thr Lys Glu Leu Ile Asn Lys Leu Asn Lys Gln Leu Asn Tyr Leu Gln
                 565                 570                 575

Asp Tyr Ser Leu Arg Lys Asp Ile Ile Ser Asn Glu Ile Glu Tyr Phe
             580                 585                 590

Ser Asn Lys Lys Lys Glu Leu Gln Tyr Asn Ile Asn Arg Leu Ala Glu
         595                 600                 605

Ala Val Gln Ala Lys Gln Asn Val Leu Val Ala Ser Lys Asp Val Pro
     610                 615                 620

Leu Ser Thr Leu Val Glu Leu Gln Ile Gln Lys Ser Leu Leu Thr Lys
625                 630                 635                 640

Gln Ile Glu Gln Leu Asn Lys Thr Glu Val Ser Leu Asn Lys Ala Gln
                 645                 650                 655

Leu Lys Asp Lys Leu Tyr Val Pro Lys Thr Tyr Gly Asn Glu Gly Lys
             660                 665                 670

Pro Glu Pro Tyr Tyr Leu Ile Ala Val Lys Lys Glu Val Asp Arg Leu
         675                 680                 685

Ala Gln Phe Ile Pro Lys Ile Glu Ser Met Ile Ala Lys Glu Lys Glu
     690                 695                 700

Arg Met Glu Gln Gly Pro Ala Ile Thr Gly Glu Ser Glu Glu Val Pro
705                 710                 715                 720

Ser Gly Pro Ser Ala Glu Ser Ser Thr Asp Arg Ser Thr Gln Ser Ser
                 725                 730                 735

Thr Ser Ser Ser Ser Ser Ser Ser Thr Pro Ala Ala Ala Glu Ser
             740                 745                 750

Ser Ser Ala Thr Leu Pro Glu Ala Pro Ala Pro Ala Glu Ala Ala Ser
         755                 760                 765

Pro Ser Thr Glu Ala Ser Glu Glu Thr Thr Ile Pro Pro Thr Thr Gln
     770                 775                 780

Glu Thr Gln Pro Ser Gln Ala Ala Ser Ser Thr Thr Pro Ala Lys Pro
785                 790                 795                 800

Val Met Thr Lys Leu Tyr Tyr Leu Glu Lys Leu Gln Lys Phe Leu Val
                 805                 810                 815

Phe Ser Tyr Ser Cys His Lys Tyr Val Leu Leu Gln Asn Ser Thr Ile
             820                 825                 830

Asn Lys Asp Ala Leu Ser Lys Tyr Ala Leu Thr Ser Glu Glu Asp Lys
         835                 840                 845

Ile Arg Thr Leu Lys Arg Cys Ser Glu Leu Asp Val Leu Leu Ala Ile
     850                 855                 860

Gln Asn Asn Met Pro Thr Met Tyr Ser Leu Tyr Glu Ser Ile Val Asp
865                 870                 875                 880

Gly Leu Gln Asn Ile Tyr Thr Glu Leu Tyr Glu Lys Glu Met Met Tyr
                 885                 890                 895

His Ile Tyr Lys Leu Lys Asp Glu Asn Pro Ser Ile Lys Ser Leu Leu
             900                 905                 910

Val Lys Ala Gly Val Ile Glu Pro Glu Pro Val Ala Ala Pro Thr Pro
         915                 920                 925

Val Thr Pro Ala Ala Thr Glu Gln Gln Gln Gln Ala Thr Pro Asp
     930                 935                 940

Val Gln Ser Asp Ala Pro Ala Pro Ser Asp Val Ser Gln Gln Pro Glu
945                 950                 955                 960

```
Thr Pro Val Thr Ser Thr Thr Pro Glu Val Thr Ser Thr Glu Ala
            965                 970                 975

Ser Ser Ser Ala Pro Gly Glu Gly Thr Pro Ser Gly Glu Ala Gly Ala
            980                 985                 990

Ser Gly Thr Glu Gly Ala Thr Ala Ser Asn Ala Ala Thr Pro Ala Gly
            995                 1000                1005

Thr Ser Ala Ser Gly Ser Ala Ala Ser Asn Ala Ser Thr Thr Ser
    1010                1015                1020

Asp Val Thr Pro Pro Ala Ala Ala Ala Val Pro Ser Thr Ser
    1025                1030                1035

Thr Pro Ala Pro Ala Gln Pro Pro Ala Ala Asn Ser Gln Ser Gly
    1040                1045                1050

Asn Pro Asp Ser Gly Ile Arg Ser Arg Ala Glu Ser Glu Glu Asp
    1055                1060                1065

Met Pro Ala Asp Asp Phe Glu Leu Asp Asn Leu Tyr Lys Ser Tyr
    1070                1075                1080

Leu Gln Gln Ile Asp Gly Asn Asn Thr Glu Phe Ile Asn Phe Ile
    1085                1090                1095

Lys Ser Lys Lys Glu Leu Ile Lys Ala Leu Thr Pro Glu Lys Val
    1100                1105                1110

Asn Gln Leu Tyr Leu Glu Ile Ala His Leu Lys Glu Leu Ser Glu
    1115                1120                1125

His Tyr Tyr Asp Arg Tyr Ser Thr Tyr Lys Leu Lys Leu Glu Arg
    1130                1135                1140

Leu Tyr Asn Lys His Glu Gln Ile Gln Leu Thr Asn Arg Gln Ile
    1145                1150                1155

Arg Asp Leu Ser Ile Leu Lys Ala Arg Leu Leu Lys Arg Lys Gln
    1160                1165                1170

Thr Leu Asn Gly Val Phe Tyr Ile Leu Asn Gly Tyr Val Asn Phe
    1175                1180                1185

Phe Asn Lys Arg Arg Glu Ala Glu Lys Gln Tyr Val Asp Asn Ala
    1190                1195                1200

Leu Lys Asn Thr Asp Met Leu Leu Lys Tyr Tyr Lys Ala Arg Thr
    1205                1210                1215

Lys Tyr Phe Thr Ser Glu Ala Val Pro Leu Lys Thr Leu Ser Lys
    1220                1225                1230

Ala Ser Leu Asp Arg Glu Ser Asn Tyr Leu Lys Ile Glu Lys Phe
    1235                1240                1245

Arg Ala Tyr Ser Arg Leu Glu Leu Arg Leu Lys Lys Asn Ile Asn
    1250                1255                1260

Leu Gly Lys Glu Arg Ile Ser Tyr Val Ser Gly Gly Leu His His
    1265                1270                1275

Val Phe Glu Glu Phe Lys Glu Leu Ile Lys Asp Lys Asp Tyr Thr
    1280                1285                1290

Gly Lys Lys Asn Pro Asp Asn Ala Pro Glu Val Thr Asn Ala Phe
    1295                1300                1305

Glu Gln Tyr Lys Glu Leu Leu Pro Lys Gly Val Thr Val Ser Thr
    1310                1315                1320

Pro Ala Val Ala Val Thr Thr Leu Ala Ala Asp Ala Pro Ala
    1325                1330                1335

Thr Pro Glu Gly Ala Val Pro Gly Ala Val Pro Gly Ala Val Pro
    1340                1345                1350

Gly Ala Val Pro Gly Ala Val Pro Gly Ala Val Pro Gly Ser Gly
```

```
            1355                1360                1365

Thr Asp Thr Arg Val Ala Gly Ser Ser Val Asp Asp Asn Glu Asp
    1370                1375                1380

Asp Asp Ile Tyr Gln Ile Ala Ser Gly Gln Ser Glu Asp Ala Pro
    1385                1390                1395

Glu Lys Asp Ile Leu Ser Glu Phe Thr Asn Glu Ser Leu Tyr Val
    1400                1405                1410

Tyr Thr Lys Arg Leu Gly Ser Thr Tyr Lys Ser Leu Lys Lys His
    1415                1420                1425

Met Leu Arg Glu Phe Ser Thr Ile Lys Glu Asp Met Thr Asn Gly
    1430                1435                1440

Leu Asn Asn Lys Ser Gln Lys Arg Asn Asp Phe Leu Glu Val Leu
    1445                1450                1455

Ser His Glu Leu Asp Leu Phe Lys Asp Leu Ser Thr Asn Lys Tyr
    1460                1465                1470

Val Ile Arg Asn Pro Tyr Gln Leu Leu Asp Asn Asp Lys Lys Asp
    1475                1480                1485

Lys Gln Ile Val Asn Leu Lys Tyr Ala Thr Lys Gly Ile Asn Glu
    1490                1495                1500

Asp Ile Glu Thr Thr Thr Asp Gly Ile Lys Phe Phe Asn Lys Met
    1505                1510                1515

Val Glu Leu Tyr Asn Thr Gln Leu Ala Ala Val Lys Glu Gln Ile
    1520                1525                1530

Ala Thr Ile Glu Ala Glu Thr Asn Asp Thr Asn Lys Glu Glu Lys
    1535                1540                1545

Lys Lys Tyr Ile Pro Ile Leu Glu Asp Leu Lys Gly Leu Tyr Glu
    1550                1555                1560

Thr Val Ile Gly Gln Ala Glu Glu Tyr Ser Glu Glu Leu Gln Asn
    1565                1570                1575

Arg Leu Asp Asn Tyr Lys Asn Glu Lys Ala Glu Phe Glu Ile Leu
    1580                1585                1590

Thr Lys Asn Leu Glu Lys Tyr Ile Gln Ile Asp Glu Lys Leu Asp
    1595                1600                1605

Glu Phe Val Glu His Ala Glu Asn Asn Lys His Ile Ala Ser Ile
    1610                1615                1620

Ala Leu Asn Asn Leu Asn Lys Ser Gly Leu Val Gly Glu Gly Glu
    1625                1630                1635

Ser Lys Lys Ile Leu Ala Lys Met Leu Asn Met Asp Gly Met Asp
    1640                1645                1650

Leu Leu Gly Val Asp Pro Lys His Val Cys Val Asp Thr Arg Asp
    1655                1660                1665

Ile Pro Lys Asn Ala Gly Cys Phe Arg Asp Asp Asn Gly Thr Glu
    1670                1675                1680

Glu Trp Arg Cys Leu Leu Gly Tyr Lys Lys Gly Glu Gly Asn Thr
    1685                1690                1695

Cys Val Glu Asn Asn Asn Pro Thr Cys Asp Ile Asn Asn Gly Gly
    1700                1705                1710

Cys Asp Pro Thr Ala Ser Cys Gln Asn Ala Glu Ser Thr Glu Asn
    1715                1720                1725

Ser Lys Lys Ile Ile Cys Thr Cys Lys Glu Pro Thr Pro Asn Ala
    1730                1735                1740

Tyr Tyr Glu Gly Val Phe Cys Ser Ser Ser Phe Met Gly Leu
    1745                1750                1755
```

```
Ser Ile Leu Leu Ile Ile Thr  Leu Ile Val Phe Asn  Ile Phe
    1760              1765              1770

<210> SEQ ID NO 9
<211> LENGTH: 5282
<212> TYPE: DNA
<213> ORGANISM: Plasmodium falciparum
<220> FEATURE:
<221> NAME/KEY: CDS
<222> LOCATION: (72)..(4964)
<220> FEATURE:
<221> NAME/KEY: sig_peptide
<222> LOCATION: (72)..(128)
<220> FEATURE:
<221> NAME/KEY: misc_feature
<222> LOCATION: (4809)..(4964)
<223> OTHER INFORMATION: predicted membrane anchor sequence

<400> SEQUENCE: 9
tttaaattat taacttattt tattattatt atttttattt atatatatta tttattagct      60
ttaattcaat a atg aag atc ata ttc ttt tta tgt tca ttt ctt ttt ttt     110
           Met Lys Ile Ile Phe Phe Leu Cys Ser Phe Leu Phe Phe
             1               5                  10 att ata aat aca caa tgt gta aca cat gaa agt tat caa gaa ctt gtc      158
Ile Ile Asn Thr Gln Cys Val Thr His Glu Ser Tyr Gln Glu Leu Val
         15                  20                  25 aaa aaa cta gaa gct tta gaa gat gca gta ttg aca ggt tat agt tta      206
Lys Lys Leu Glu Ala Leu Glu Asp Ala Val Leu Thr Gly Tyr Ser Leu
 30                  35                  40                  45 ttt cat aag gaa aaa atg atc tta aat gaa gaa gaa att act aca aaa      254
Phe His Lys Glu Lys Met Ile Leu Asn Glu Glu Glu Ile Thr Thr Lys
                 50                  55                  60 ggt gca agt gct caa agt ggt aca agt ggt aca agt ggt aca agt ggt      302
Gly Ala Ser Ala Gln Ser Gly Thr Ser Gly Thr Ser Gly Thr Ser Gly
             65                  70                  75 cca agt ggt cca agt ggt aca agt cca tca tct cgt tca aac act tta      350
Pro Ser Gly Pro Ser Gly Thr Ser Pro Ser Ser Arg Ser Asn Thr Leu
         80                  85                  90 cct cgt tca aat act tca tct ggt gca agc cct cca gct gat gca agc      398
Pro Arg Ser Asn Thr Ser Ser Gly Ala Ser Pro Pro Ala Asp Ala Ser
     95                 100                 105 gat tca gat gct aaa tct tac gct gat tta aaa cac aga gta cga aat      446
Asp Ser Asp Ala Lys Ser Tyr Ala Asp Leu Lys His Arg Val Arg Asn
110                 115                 120                 125 tac ttg tta act atc aaa gaa ctc aaa tat cct caa ctc ttt gat tta      494
Tyr Leu Leu Thr Ile Lys Glu Leu Lys Tyr Pro Gln Leu Phe Asp Leu
                130                 135                 140 act aat cat atg tta act ttg tgt gat aat att cat ggt ttc aaa tat      542
Thr Asn His Met Leu Thr Leu Cys Asp Asn Ile His Gly Phe Lys Tyr
            145                 150                 155 tta att gat gga tat gaa gaa att aat gaa tta tta tat aaa tta aac      590
Leu Ile Asp Gly Tyr Glu Glu Ile Asn Glu Leu Leu Tyr Lys Leu Asn
        160                 165                 170 ttt tat ttt gat tta tta aga gca aaa tta aat gat gta tgt gct aat      638
Phe Tyr Phe Asp Leu Leu Arg Ala Lys Leu Asn Asp Val Cys Ala Asn
    175                 180                 185 gat tat tgt caa ata cct ttc aat ctt aaa att cgt gca aat gaa tta      686
Asp Tyr Cys Gln Ile Pro Phe Asn Leu Lys Ile Arg Ala Asn Glu Leu
190                 195                 200                 205 gac gta ctt aaa aaa ctt gtg ttc gga tat aga aaa cca tta gac aat      734
Asp Val Leu Lys Lys Leu Val Phe Gly Tyr Arg Lys Pro Leu Asp Asn
                210                 215                 220 att aaa gat aat gta gga aaa atg gaa gat tac att aaa aaa aat aaa      782
```

```
Ile Lys Asp Asn Val Gly Lys Met Glu Asp Tyr Ile Lys Lys Asn Lys
            225                 230                 235 aaa acc ata gaa aat ata aat gaa tta att gaa gaa agt aag aaa aca        830
Lys Thr Ile Glu Asn Ile Asn Glu Leu Ile Glu Glu Ser Lys Lys Thr
            240                 245                 250 att gat aaa aat aag aat gca act aaa gaa gaa gaa aaa aaa aaa tta        878
Ile Asp Lys Asn Lys Asn Ala Thr Lys Glu Glu Glu Lys Lys Lys Leu
            255                 260                 265 tac caa gct caa tat gat ctt tct att tac aat aaa caa tta gaa gaa        926
Tyr Gln Ala Gln Tyr Asp Leu Ser Ile Tyr Asn Lys Gln Leu Glu Glu
270                 275                 280                 285 gca cat aat tta ata agc gtt tta gaa aaa cgt att gac act tta aaa        974
Ala His Asn Leu Ile Ser Val Leu Glu Lys Arg Ile Asp Thr Leu Lys
                290                 295                 300 aaa aat gaa aac att aag gaa tta ctt gat aag ata aat gaa att aaa       1022
Lys Asn Glu Asn Ile Lys Glu Leu Leu Asp Lys Ile Asn Glu Ile Lys
                305                 310                 315 aat ccc cca ccg gcc aat tct gga aat aca cca aat act ctc ctt gat       1070
Asn Pro Pro Pro Ala Asn Ser Gly Asn Thr Pro Asn Thr Leu Leu Asp
            320                 325                 330 aag aac aaa aaa atc gag gaa cac gaa aaa gaa ata aaa gaa att gcc       1118
Lys Asn Lys Lys Ile Glu Glu His Glu Lys Glu Ile Lys Glu Ile Ala
335                 340                 345 aaa act att aaa ttt aat att gat agt tta ttt act gat cca ctt gaa       1166
Lys Thr Ile Lys Phe Asn Ile Asp Ser Leu Phe Thr Asp Pro Leu Glu
350                 355                 360                 365 tta gaa tac tat tta aga gaa aaa aat aaa aat att gat ata agt gca       1214
Leu Glu Tyr Tyr Leu Arg Glu Lys Asn Lys Asn Ile Asp Ile Ser Ala
                370                 375                 380 aag gtt gaa aca aag gaa tca act gaa ccc aat gaa tat cca aat gga       1262
Lys Val Glu Thr Lys Glu Ser Thr Glu Pro Asn Glu Tyr Pro Asn Gly
            385                 390                 395 gtt act tat cct ttg tca tat aac gat att aac aat gct tta aat gaa       1310
Val Thr Tyr Pro Leu Ser Tyr Asn Asp Ile Asn Asn Ala Leu Asn Glu
            400                 405                 410 ctt aat tct ttt ggt gat tta att aat cca ttt gat tat aca aaa gaa       1358
Leu Asn Ser Phe Gly Asp Leu Ile Asn Pro Phe Asp Tyr Thr Lys Glu
            415                 420                 425 cca agt aaa aac ata tat act gat aat gaa aga aaa aaa ttc ata aat       1406
Pro Ser Lys Asn Ile Tyr Thr Asp Asn Glu Arg Lys Lys Phe Ile Asn
430                 435                 440                 445 gaa att aag gaa aaa att aaa ata gaa aaa aaa aaa att gaa tct gat       1454
Glu Ile Lys Glu Lys Ile Lys Ile Glu Lys Lys Lys Ile Glu Ser Asp
                450                 455                 460 aaa aaa tct tac gaa gac aga tct aag tct tta aat gat ata aca aaa       1502
Lys Lys Ser Tyr Glu Asp Arg Ser Lys Ser Leu Asn Asp Ile Thr Lys
            465                 470                 475 gaa tat gaa aaa tta ctt aat gaa att tat gat agc aaa ttc aat aat       1550
Glu Tyr Glu Lys Leu Leu Asn Glu Ile Tyr Asp Ser Lys Phe Asn Asn
            480                 485                 490 aat ata gat tta act aat ttc gaa aaa atg atg ggt aaa aga tat tca       1598
Asn Ile Asp Leu Thr Asn Phe Glu Lys Met Met Gly Lys Arg Tyr Ser
495                 500                 505 tat aaa gtt gag aaa ctt aca cac cat aat act ttt gca tcc tat gaa       1646
Tyr Lys Val Glu Lys Leu Thr His His Asn Thr Phe Ala Ser Tyr Glu
510                 515                 520                 525 aat tct aaa cat aat ctt gaa aag tta aca aaa gct ctt aaa tat atg       1694
Asn Ser Lys His Asn Leu Glu Lys Leu Thr Lys Ala Leu Lys Tyr Met
                530                 535                 540 gaa gat tat tct tta agg aat ata gta gtt gaa aaa gaa tta aaa tat       1742
```

-continued

```
                        Glu Asp Tyr Ser Leu Arg Asn Ile Val Val Glu Lys Glu Leu Lys Tyr
                                        545                 550                 555 tat aaa aat tta ata agc aaa ata gaa aat gag att gaa aca tta gtt       1790
Tyr Lys Asn Leu Ile Ser Lys Ile Glu Asn Glu Ile Glu Thr Leu Val
                560                 565                 570 gaa aat att aaa aaa gat gaa gaa cag ctt ttt gaa aaa aaa att act       1838
Glu Asn Ile Lys Lys Asp Glu Glu Gln Leu Phe Glu Lys Lys Ile Thr
            575                 580                 585 aaa gac gaa aat aaa cca gat gaa aaa att tta gaa gta tct gac att       1886
Lys Asp Glu Asn Lys Pro Asp Glu Lys Ile Leu Glu Val Ser Asp Ile
590                 595                 600                 605 gta aaa gta caa gtt caa aaa gtt tta tta atg aac aaa att gac gaa       1934
Val Lys Val Gln Val Gln Lys Val Leu Leu Met Asn Lys Ile Asp Glu
                610                 615                 620 tta aaa aag act caa ttg att tta aaa aat gta gaa tta aaa cat aat       1982
Leu Lys Lys Thr Gln Leu Ile Leu Lys Asn Val Glu Leu Lys His Asn
            625                 630                 635 ata cat gtt ccc aat tct tac aaa caa gaa aat aag caa gaa cct tat       2030
Ile His Val Pro Asn Ser Tyr Lys Gln Glu Asn Lys Gln Glu Pro Tyr
        640                 645                 650 tat tta att gtg ttg aaa aaa gaa att gat aaa tta aaa gtg ttc atg       2078
Tyr Leu Ile Val Leu Lys Lys Glu Ile Asp Lys Leu Lys Val Phe Met
655                 660                 665 cct aag gta gaa tca ttg ata aat gaa gaa aaa aaa aac ata aaa aca       2126
Pro Lys Val Glu Ser Leu Ile Asn Glu Glu Lys Lys Asn Ile Lys Thr
670                 675                 680                 685 gaa ggt caa tcg gat aat tcg gaa cca tca acc gaa gga gaa ata aca       2174
Glu Gly Gln Ser Asp Asn Ser Glu Pro Ser Thr Glu Gly Glu Ile Thr
                690                 695                 700 gga caa gca act aca aaa cct gga caa caa gca gga tct gct tta gaa       2222
Gly Gln Ala Thr Thr Lys Pro Gly Gln Gln Ala Gly Ser Ala Leu Glu
            705                 710                 715 gga gat tca gta caa gca caa gca caa gaa caa aaa caa gca caa cca       2270
Gly Asp Ser Val Gln Ala Gln Ala Gln Glu Gln Lys Gln Ala Gln Pro
        720                 725                 730 cca gta cca gta cca gta cca gaa gca aaa gca caa gtc cca aca cca       2318
Pro Val Pro Val Pro Val Pro Glu Ala Lys Ala Gln Val Pro Thr Pro
    735                 740                 745 cca gca cca gta aat aat aaa act gaa aat gtt tcc aaa tta gat tat       2366
Pro Ala Pro Val Asn Asn Lys Thr Glu Asn Val Ser Lys Leu Asp Tyr
750                 755                 760                 765 ctt gaa aaa tta tat gaa ttt tta aat act tca tat ata tgt cac aaa       2414
Leu Glu Lys Leu Tyr Glu Phe Leu Asn Thr Ser Tyr Ile Cys His Lys
                770                 775                 780 tat att ttg gtt tca cac tca act atg aac gaa aag ata tta aaa caa       2462
Tyr Ile Leu Val Ser His Ser Thr Met Asn Glu Lys Ile Leu Lys Gln
            785                 790                 795 tat aaa att aca aag gag gaa gaa agc aaa tta agt tca tgt gat cca       2510
Tyr Lys Ile Thr Lys Glu Glu Glu Ser Lys Leu Ser Ser Cys Asp Pro
        800                 805                 810 tta gac tta ttg ttt aat ata caa aat aac ata cct gta atg tat tct       2558
Leu Asp Leu Leu Phe Asn Ile Gln Asn Asn Ile Pro Val Met Tyr Ser
815                 820                 825 atg ttt gat agc tta aac aat agt tta tca caa cta ttt atg gaa att       2606
Met Phe Asp Ser Leu Asn Asn Ser Leu Ser Gln Leu Phe Met Glu Ile
830                 835                 840                 845 tat gaa aaa gaa atg gtt tgt aat tta tat aaa ctt aag gat aat gac       2654
Tyr Glu Lys Glu Met Val Cys Asn Leu Tyr Lys Leu Lys Asp Asn Asp
                850                 855                 860 aaa att aaa aat tta tta gag gaa gcg aaa aaa gta tcc aca tct gta       2702
```

-continued

| | |
|---|---|
| Lys Ile Lys Asn Leu Leu Glu Glu Ala Lys Lys Val Ser Thr Ser Val<br>        865                       870                      875 | |
| aaa act ctt tca agt tca tca atg caa cca tta tca tta aca cct cag<br>Lys Thr Leu Ser Ser Ser Ser Met Gln Pro Leu Ser Leu Thr Pro Gln<br>        880                       885                      890 | 2750 |
| gat aaa ccc gaa gta agt gca aat gat gat aca tca cat tct aca aat<br>Asp Lys Pro Glu Val Ser Ala Asn Asp Asp Thr Ser His Ser Thr Asn<br> 895                     900                     905 | 2798 |
| ttg aat aat agt tta aaa tta ttt gaa aac ata ttg agt ctt gga aaa<br>Leu Asn Asn Ser Leu Lys Leu Phe Glu Asn Ile Leu Ser Leu Gly Lys<br>910                     915                     920                 925 | 2846 |
| aac aaa aat ata tac caa gaa tta ata ggt caa aaa agt agt gaa aac<br>Asn Lys Asn Ile Tyr Gln Glu Leu Ile Gly Gln Lys Ser Ser Glu Asn<br>               930                     935                     940 | 2894 |
| ttt tat gaa aag ata tta aaa gat agt gat aca ttt tat aat gaa tct<br>Phe Tyr Glu Lys Ile Leu Lys Asp Ser Asp Thr Phe Tyr Asn Glu Ser<br>        945                       950                     955 | 2942 |
| ttt aca aat ttt gta aaa tct aaa gct gat gat att aat tca ttg aat<br>Phe Thr Asn Phe Val Lys Ser Lys Ala Asp Asp Ile Asn Ser Leu Asn<br>               960                     965                     970 | 2990 |
| gat gaa tca aaa agg aag aaa tta gaa gaa gat att aat aaa tta aaa<br>Asp Glu Ser Lys Arg Lys Lys Leu Glu Glu Asp Ile Asn Lys Leu Lys<br> 975                     980                     985 | 3038 |
| aaa act tta cag tta tca ttt gat tta tat aat  aaa tat aaa tta aaa<br>Lys Thr Leu Gln Leu Ser Phe Asp Leu Tyr Asn  Lys Tyr Lys Leu Lys<br>990                     995                     1000                1005 | 3086 |
| tta gaa aga tta ttt  gat aaa aag aaa aca  gtt ggt aaa tat aaa<br>Leu Glu Arg Leu Phe  Asp Lys Lys Lys Thr  Val Gly Lys Tyr Lys<br>              1010                      1015                1020 | 3131 |
| atg caa att aaa aaa  ctt act tta tta aaa  gaa caa tta gaa tca<br>Met Gln Ile Lys Lys  Leu Thr Leu Leu Lys  Glu Gln Leu Glu Ser<br>              1025                      1030                1035 | 3176 |
| aaa ttg aat tca ctt  aat aac cca aag cat  gta tta caa aac ttt<br>Lys Leu Asn Ser Leu  Asn Asn Pro Lys His  Val Leu Gln Asn Phe<br>              1040                      1045                1050 | 3221 |
| tct gtt ttc ttt aac  aaa aaa aaa gaa gct  gaa ata gca gaa act<br>Ser Val Phe Phe Asn  Lys Lys Lys Glu Ala  Glu Ile Ala Glu Thr<br>              1055                      1060                1065 | 3266 |
| gaa aac aca tta gaa  aac aca aaa ata tta  ttg aaa cat tat aaa<br>Glu Asn Thr Leu Glu  Asn Thr Lys Ile Leu  Leu Lys His Tyr Lys<br>              1070                      1075                1080 | 3311 |
| gga ctt gtt aaa tat  tat aat ggt gaa tca  tct cca tta aaa act<br>Gly Leu Val Lys Tyr  Tyr Asn Gly Glu Ser  Ser Pro Leu Lys Thr<br>              1085                      1090                1095 | 3356 |
| tta agt gaa gaa tca  att caa aca gaa gat  aat tat gcc agt tta<br>Leu Ser Glu Glu Ser  Ile Gln Thr Glu Asp  Asn Tyr Ala Ser Leu<br>              1100                      1105                1110 | 3401 |
| gaa aac ttt aaa gta  tta agt aaa tta gaa  gga aaa tta aag gat<br>Glu Asn Phe Lys Val  Leu Ser Lys Leu Glu  Gly Lys Leu Lys Asp<br>              1115                      1120                1125 | 3446 |
| aat tta aat tta gaa  aag aaa aaa tta tca  tac tta tca agt gga<br>Asn Leu Asn Leu Glu  Lys Lys Lys Leu Ser  Tyr Leu Ser Ser Gly<br>              1130                      1135                1140 | 3491 |
| tta cat cat tta att  gct gaa tta aaa gaa  gta ata aaa aat aaa<br>Leu His His Leu Ile  Ala Glu Leu Lys Glu  Val Ile Lys Asn Lys<br>              1145                      1150                1155 | 3536 |
| aat tat aca ggt aat  tct cca agt gaa aat  aat acg gat gtt aac<br>Asn Tyr Thr Gly Asn  Ser Pro Ser Glu Asn  Asn Thr Asp Val Asn<br>              1160                      1165                1170 | 3581 |
| aat gca tta gaa tct  tac aaa aaa ttt ctc  cca gaa gga aca gat | 3626 |

-continued

| | | | | | | | | | | | |
|---|---|---|---|---|---|---|---|---|---|---|---|
| Asn | Ala | Leu | Glu | Ser<br>1175 | Tyr | Lys | Lys | Phe<br>1180 | Leu | Pro | Glu | Gly | Thr | Asp<br>1185 | | |

```
gtt gca aca gtt gta    agt gaa agt gga tcc    gac aca tta gaa caa         3671
Val Ala Thr Val Val    Ser Glu Ser Gly Ser    Asp Thr Leu Glu Gln
            1190                    1195                    1200 agt caa cca aag aaa    cca gca tca act cat    gta gga gca gag tct         3716
Ser Gln Pro Lys Lys    Pro Ala Ser Thr His    Val Gly Ala Glu Ser
            1205                    1210                    1215 aac aca ata aca aca    tca caa aat gtc gat    gat gaa gta gat gac         3761
Asn Thr Ile Thr Thr    Ser Gln Asn Val Asp    Asp Glu Val Asp Asp
            1220                    1225                    1230 gta atc ata gta cct    ata ttt gga gaa tcc    gaa gaa gat tat gat         3806
Val Ile Ile Val Pro    Ile Phe Gly Glu Ser    Glu Glu Asp Tyr Asp
            1235                    1240                    1245 gat tta gga caa gta    gta aca gga gaa gca    gta act cct tcc gta         3851
Asp Leu Gly Gln Val    Val Thr Gly Glu Ala    Val Thr Pro Ser Val
            1250                    1255                    1260 att gat aac ata ctt    tct aaa att gaa aat    gaa tat gag gtt tta         3896
Ile Asp Asn Ile Leu    Ser Lys Ile Glu Asn    Glu Tyr Glu Val Leu
            1265                    1270                    1275 tat tta aaa cct tta    gca ggt gtt tat aga    agt tta aaa aaa caa         3941
Tyr Leu Lys Pro Leu    Ala Gly Val Tyr Arg    Ser Leu Lys Lys Gln
            1280                    1285                    1290 tta gaa aat aac gtt    atg aca ttt aat gtt    aat gtt aag gat att         3986
Leu Glu Asn Asn Val    Met Thr Phe Asn Val    Asn Val Lys Asp Ile
            1295                    1300                    1305 tta aat tca cga ttt    aat aaa cgt gaa aat    ttc aaa aat gtt tta         4031
Leu Asn Ser Arg Phe    Asn Lys Arg Glu Asn    Phe Lys Asn Val Leu
            1310                    1315                    1320 gaa tca gat tta att    cca tat aaa gat tta    aca tca agt aat tat         4076
Glu Ser Asp Leu Ile    Pro Tyr Lys Asp Leu    Thr Ser Ser Asn Tyr
            1325                    1330                    1335 gtt gtc aaa gat cca    tat aaa ttt ctt aat    aaa gaa aaa aga gat         4121
Val Val Lys Asp Pro    Tyr Lys Phe Leu Asn    Lys Glu Lys Arg Asp
            1340                    1345                    1350 aaa ttc tta agc agt    tat aat tat att aag    gat tca ata gat acg         4166
Lys Phe Leu Ser Ser    Tyr Asn Tyr Ile Lys    Asp Ser Ile Asp Thr
            1355                    1360                    1365 gat ata aat ttt gca    aat gat gtt ctt gga    tat tat aaa ata tta         4211
Asp Ile Asn Phe Ala    Asn Asp Val Leu Gly    Tyr Tyr Lys Ile Leu
            1370                    1375                    1380 tcc gaa aaa tat aaa    tca gat tta gat tca    att aaa aaa tat atc         4256
Ser Glu Lys Tyr Lys    Ser Asp Leu Asp Ser    Ile Lys Lys Tyr Ile
            1385                    1390                    1395 aac gac aaa caa ggt    gaa aat gag aaa tac    ctt ccc ttt tta aac         4301
Asn Asp Lys Gln Gly    Glu Asn Glu Lys Tyr    Leu Pro Phe Leu Asn
            1400                    1405                    1410 aat att gag acc tta    tat aaa aca gtt aat    gat aaa att gat tta         4346
Asn Ile Glu Thr Leu    Tyr Lys Thr Val Asn    Asp Lys Ile Asp Leu
            1415                    1420                    1425 ttt gta att cat tta    gaa gca aaa gtt cta    aat tat aca tat gag         4391
Phe Val Ile His Leu    Glu Ala Lys Val Leu    Asn Tyr Thr Tyr Glu
            1430                    1435                    1440 aaa tca aac gta gaa    gtt aaa ata aaa gaa    ctt aat tac tta aaa         4436
Lys Ser Asn Val Glu    Val Lys Ile Lys Glu    Leu Asn Tyr Leu Lys
            1445                    1450                    1455 aca att caa gac aaa    ttg gca gat ttt aaa    aaa aat aac aat ttc         4481
Thr Ile Gln Asp Lys    Leu Ala Asp Phe Lys    Lys Asn Asn Asn Phe
            1460                    1465                    1470 gtt gga att gct gat    tta tca aca gat tat    aac cat aat aac tta         4526
```

|  |  |  |  |  |  |  |  |  |  |  |  |  |  |  |
|---|---|---|---|---|---|---|---|---|---|---|---|---|---|---|
| Val | Gly | Ile | Ala | Asp | Leu | Ser | Thr | Asp | Tyr | Asn | His | Asn | Asn | Leu |
|  |  |  | 1475 |  |  |  | 1480 |  |  |  | 1485 |  |  |  |

```
ttg aca aag ttc ctt agt aca ggt atg gtt ttt gaa aat ctt gct      4571
Leu Thr Lys Phe Leu Ser Thr Gly Met Val Phe Glu Asn Leu Ala
        1490                1495                1500 aaa acc gtt tta tct aat tta ctt gat gga aac ttg caa ggt atg      4616
Lys Thr Val Leu Ser Asn Leu Leu Asp Gly Asn Leu Gln Gly Met
        1505                1510                1515 tta aac att tca caa cac caa tgc gta aaa aaa caa tgt cca caa      4661
Leu Asn Ile Ser Gln His Gln Cys Val Lys Lys Gln Cys Pro Gln
        1520                1525                1530 aat tct gga tgt ttc aga cat tta gat gaa aga gaa gaa tgt aaa      4706
Asn Ser Gly Cys Phe Arg His Leu Asp Glu Arg Glu Glu Cys Lys
        1535                1540                1545 tgt tta tta aat tac aaa caa gaa ggt gat aaa tgt gtt gaa aat      4751
Cys Leu Leu Asn Tyr Lys Gln Glu Gly Asp Lys Cys Val Glu Asn
        1550                1555                1560 cca aat cct act tgt aac gaa aat aat ggt gga tgt gat gca gat      4796
Pro Asn Pro Thr Cys Asn Glu Asn Asn Gly Gly Cys Asp Ala Asp
        1565                1570                1575 gcc aaa tgt acc gaa gaa gat tca ggt agc aac gga aag aaa atc      4841
Ala Lys Cys Thr Glu Glu Asp Ser Gly Ser Asn Gly Lys Lys Ile
        1580                1585                1590 aca tgt gaa tgt act aaa cct gat tct tat cca ctt ttc gat ggt      4886
Thr Cys Glu Cys Thr Lys Pro Asp Ser Tyr Pro Leu Phe Asp Gly
        1595                1600                1605 att ttc tgc agt tcc tct aac ttc tta gga ata tca ttc tta tta      4931
Ile Phe Cys Ser Ser Ser Asn Phe Leu Gly Ile Ser Phe Leu Leu
        1610                1615                1620 ata ctc atg tta ata tta tac agt ttc att taa aaaatgtagg          4974
Ile Leu Met Leu Ile Leu Tyr Ser Phe Ile
        1625                1630 agttaaaata tgttaccta atttttttt tttttttt ttaaatatat atatatatta   5034
atatatatat ataaaatatt acataatata tatatatata tttagttatt acaggaatag 5094 tgatatttta gtcatgttca aaatatatta aaaattata aatattataa taaaaaaaaa 5154 aaaaaaaaaa aattatatac ttataaattt atacatttat acatatatat atatatattt 5214 ttttttcttc tttcttttca agttctattt tatattttat atagatttt aataaaaaac 5274 tttttaaa                                                         5282

<210> SEQ ID NO 10
<211> LENGTH: 1630
<212> TYPE: PRT
<213> ORGANISM: Plasmodium falciparum

<400> SEQUENCE: 10

Met Lys Ile Ile Phe Phe Leu Cys Ser Phe Leu Phe Phe Ile Ile Asn
1               5                   10                  15

Thr Gln Cys Val Thr His Glu Ser Tyr Gln Glu Leu Val Lys Lys Leu
            20                  25                  30

Glu Ala Leu Glu Asp Ala Val Leu Thr Gly Tyr Ser Leu Phe His Lys
        35                  40                  45

Glu Lys Met Ile Leu Asn Glu Glu Glu Ile Thr Thr Lys Gly Ala Ser
    50                  55                  60

Ala Gln Ser Gly Thr Ser Gly Thr Ser Gly Thr Ser Gly Pro Ser Gly
65                  70                  75                  80

Pro Ser Gly Thr Ser Pro Ser Ser Arg Ser Asn Thr Leu Pro Arg Ser
                85                  90                  95
```

```
Asn Thr Ser Ser Gly Ala Ser Pro Pro Ala Asp Ala Ser Asp Ser Asp
            100                 105                 110

Ala Lys Ser Tyr Ala Asp Leu Lys His Arg Val Arg Asn Tyr Leu Leu
            115                 120                 125

Thr Ile Lys Glu Leu Lys Tyr Pro Gln Leu Phe Asp Leu Thr Asn His
        130                 135                 140

Met Leu Thr Leu Cys Asp Asn Ile His Gly Phe Lys Tyr Leu Ile Asp
145                 150                 155                 160

Gly Tyr Glu Glu Ile Asn Glu Leu Leu Tyr Lys Leu Asn Phe Tyr Phe
                165                 170                 175

Asp Leu Leu Arg Ala Lys Leu Asn Asp Val Cys Ala Asn Asp Tyr Cys
            180                 185                 190

Gln Ile Pro Phe Asn Leu Lys Ile Arg Ala Asn Glu Leu Asp Val Leu
            195                 200                 205

Lys Lys Leu Val Phe Gly Tyr Arg Lys Pro Leu Asp Asn Ile Lys Asp
        210                 215                 220

Asn Val Gly Lys Met Glu Asp Tyr Ile Lys Lys Asn Lys Lys Thr Ile
225                 230                 235                 240

Glu Asn Ile Asn Glu Leu Ile Glu Glu Ser Lys Lys Thr Ile Asp Lys
                245                 250                 255

Asn Lys Asn Ala Thr Lys Glu Glu Lys Lys Lys Leu Tyr Gln Ala
            260                 265                 270

Gln Tyr Asp Leu Ser Ile Tyr Asn Lys Gln Leu Glu Glu Ala His Asn
            275                 280                 285

Leu Ile Ser Val Leu Glu Lys Arg Ile Asp Thr Leu Lys Lys Asn Glu
        290                 295                 300

Asn Ile Lys Glu Leu Leu Asp Lys Ile Asn Glu Ile Lys Asn Pro Pro
305                 310                 315                 320

Pro Ala Asn Ser Gly Asn Thr Pro Asn Thr Leu Leu Asp Lys Asn Lys
                325                 330                 335

Lys Ile Glu Glu His Glu Lys Glu Ile Lys Glu Ile Ala Lys Thr Ile
            340                 345                 350

Lys Phe Asn Ile Asp Ser Leu Phe Thr Asp Pro Leu Glu Leu Glu Tyr
            355                 360                 365

Tyr Leu Arg Glu Lys Asn Lys Asn Ile Asp Ile Ser Ala Lys Val Glu
        370                 375                 380

Thr Lys Glu Ser Thr Glu Pro Asn Glu Tyr Pro Asn Gly Val Thr Tyr
385                 390                 395                 400

Pro Leu Ser Tyr Asn Asp Ile Asn Asn Ala Leu Asn Glu Leu Asn Ser
                405                 410                 415

Phe Gly Asp Leu Ile Asn Pro Phe Asp Tyr Thr Lys Glu Pro Ser Lys
            420                 425                 430

Asn Ile Tyr Thr Asp Asn Glu Arg Lys Lys Phe Ile Asn Glu Ile Lys
            435                 440                 445

Glu Lys Ile Lys Ile Glu Lys Lys Ile Glu Ser Asp Lys Lys Ser
        450                 455                 460

Tyr Glu Asp Arg Ser Lys Ser Leu Asn Asp Ile Thr Lys Glu Tyr Glu
465                 470                 475                 480

Lys Leu Leu Asn Glu Ile Tyr Asp Ser Lys Phe Asn Asn Ile Asp
                485                 490                 495

Leu Thr Asn Phe Glu Lys Met Met Gly Lys Arg Tyr Ser Tyr Lys Val
            500                 505                 510

Glu Lys Leu Thr His His Asn Thr Phe Ala Ser Tyr Glu Asn Ser Lys
```

```
                515                 520                 525
His Asn Leu Glu Lys Leu Thr Lys Ala Leu Lys Tyr Met Glu Asp Tyr
    530                 535                 540

Ser Leu Arg Asn Ile Val Val Glu Lys Glu Leu Lys Tyr Tyr Lys Asn
545                 550                 555                 560

Leu Ile Ser Lys Ile Glu Asn Glu Ile Glu Thr Leu Val Glu Asn Ile
                565                 570                 575

Lys Lys Asp Glu Glu Gln Leu Phe Glu Lys Ile Thr Lys Asp Glu
            580                 585                 590

Asn Lys Pro Asp Glu Lys Ile Leu Glu Val Ser Asp Ile Val Lys Val
            595                 600                 605

Gln Val Gln Lys Val Leu Leu Met Asn Lys Ile Asp Glu Leu Lys Lys
    610                 615                 620

Thr Gln Leu Ile Leu Lys Asn Val Glu Leu Lys His Asn Ile His Val
625                 630                 635                 640

Pro Asn Ser Tyr Lys Gln Glu Asn Lys Gln Glu Pro Tyr Tyr Leu Ile
                645                 650                 655

Val Leu Lys Lys Glu Ile Asp Lys Leu Lys Val Phe Met Pro Lys Val
            660                 665                 670

Glu Ser Leu Ile Asn Glu Glu Lys Lys Asn Ile Lys Thr Glu Gly Gln
    675                 680                 685

Ser Asp Asn Ser Glu Pro Ser Thr Glu Gly Glu Ile Thr Gly Gln Ala
    690                 695                 700

Thr Thr Lys Pro Gly Gln Gln Ala Gly Ser Ala Leu Glu Gly Asp Ser
705                 710                 715                 720

Val Gln Ala Gln Ala Gln Glu Gln Lys Gln Ala Gln Pro Pro Val Pro
                725                 730                 735

Val Pro Val Pro Glu Ala Lys Ala Gln Val Pro Thr Pro Pro Ala Pro
            740                 745                 750

Val Asn Asn Lys Thr Glu Asn Val Ser Lys Leu Asp Tyr Leu Glu Lys
                755                 760                 765

Leu Tyr Glu Phe Leu Asn Thr Ser Tyr Ile Cys His Lys Tyr Ile Leu
770                 775                 780

Val Ser His Ser Thr Met Asn Glu Lys Ile Leu Lys Gln Tyr Lys Ile
785                 790                 795                 800

Thr Lys Glu Glu Glu Ser Lys Leu Ser Ser Cys Asp Pro Leu Asp Leu
                805                 810                 815

Leu Phe Asn Ile Gln Asn Asn Ile Pro Val Met Tyr Ser Met Phe Asp
            820                 825                 830

Ser Leu Asn Asn Ser Leu Ser Gln Leu Phe Met Glu Ile Tyr Glu Lys
            835                 840                 845

Glu Met Val Cys Asn Leu Tyr Lys Leu Lys Asp Asn Asp Lys Ile Lys
    850                 855                 860

Asn Leu Leu Glu Glu Ala Lys Lys Val Ser Thr Ser Val Lys Thr Leu
865                 870                 875                 880

Ser Ser Ser Ser Met Gln Pro Leu Ser Leu Thr Pro Gln Asp Lys Pro
                885                 890                 895

Glu Val Ser Ala Asn Asp Asp Thr Ser His Ser Thr Asn Leu Asn Asn
            900                 905                 910

Ser Leu Lys Leu Phe Glu Asn Ile Leu Ser Leu Gly Lys Asn Lys Asn
    915                 920                 925

Ile Tyr Gln Glu Leu Ile Gly Gln Lys Ser Ser Glu Asn Phe Tyr Glu
    930                 935                 940
```

-continued

Lys Ile Leu Lys Asp Ser Asp Thr Phe Tyr Asn Glu Ser Phe Thr Asn
945                 950                 955                 960

Phe Val Lys Ser Lys Ala Asp Ile Asn Ser Leu Asn Asp Glu Ser
            965                 970                 975

Lys Arg Lys Lys Leu Glu Glu Asp Ile Asn Lys Leu Lys Thr Leu
            980                 985                 990

Gln Leu Ser Phe Asp Leu Tyr Asn Lys Tyr Lys Leu Lys Leu Glu Arg
            995                 1000                1005

Leu Phe Asp Lys Lys Lys Thr Val Gly Lys Tyr Lys Met Gln Ile
    1010            1015                1020

Lys Lys Leu Thr Leu Leu Lys Glu Gln Leu Glu Ser Lys Leu Asn
    1025            1030                1035

Ser Leu Asn Asn Pro Lys His Val Leu Gln Asn Phe Ser Val Phe
    1040            1045                1050

Phe Asn Lys Lys Lys Glu Ala Glu Ile Ala Glu Thr Glu Asn Thr
    1055            1060                1065

Leu Glu Asn Thr Lys Ile Leu Leu Lys His Tyr Lys Gly Leu Val
    1070            1075                1080

Lys Tyr Tyr Asn Gly Glu Ser Ser Pro Leu Lys Thr Leu Ser Glu
    1085            1090                1095

Glu Ser Ile Gln Thr Glu Asp Asn Tyr Ala Ser Leu Glu Asn Phe
    1100            1105                1110

Lys Val Leu Ser Lys Leu Glu Gly Lys Leu Lys Asp Asn Leu Asn
    1115            1120                1125

Leu Glu Lys Lys Lys Leu Ser Tyr Leu Ser Ser Gly Leu His His
    1130            1135                1140

Leu Ile Ala Glu Leu Lys Glu Val Ile Lys Asn Lys Asn Tyr Thr
    1145            1150                1155

Gly Asn Ser Pro Ser Glu Asn Asn Thr Asp Val Asn Asn Ala Leu
    1160            1165                1170

Glu Ser Tyr Lys Lys Phe Leu Pro Glu Gly Thr Asp Val Ala Thr
    1175            1180                1185

Val Val Ser Glu Ser Gly Ser Asp Thr Leu Glu Gln Ser Gln Pro
    1190            1195                1200

Lys Lys Pro Ala Ser Thr His Val Gly Ala Glu Ser Asn Thr Ile
    1205            1210                1215

Thr Thr Ser Gln Asn Val Asp Asp Glu Val Asp Val Ile Ile
    1220            1225                1230

Val Pro Ile Phe Gly Glu Ser Glu Glu Asp Tyr Asp Asp Leu Gly
    1235            1240                1245

Gln Val Val Thr Gly Glu Ala Val Thr Pro Ser Val Ile Asp Asn
    1250            1255                1260

Ile Leu Ser Lys Ile Glu Asn Glu Tyr Glu Val Leu Tyr Leu Lys
    1265            1270                1275

Pro Leu Ala Gly Val Tyr Arg Ser Leu Lys Lys Gln Leu Glu Asn
    1280            1285                1290

Asn Val Met Thr Phe Asn Val Asn Val Lys Asp Ile Leu Asn Ser
    1295            1300                1305

Arg Phe Asn Lys Arg Glu Asn Phe Lys Asn Val Leu Glu Ser Asp
    1310            1315                1320

Leu Ile Pro Tyr Lys Asp Leu Thr Ser Ser Asn Tyr Val Val Lys
    1325            1330                1335

Asp Pro Tyr Lys Phe Leu Asn Lys Glu Lys Arg Asp Lys Phe Leu
    1340            1345                1350

```
Ser  Ser  Tyr  Asn  Tyr  Ile  Lys  Asp  Ser  Ile  Asp  Thr  Asp  Ile  Asn
     1355                1360                1365

Phe  Ala  Asn  Asp  Val  Leu  Gly  Tyr  Tyr  Lys  Ile  Leu  Ser  Glu  Lys
     1370                1375                1380

Tyr  Lys  Ser  Asp  Leu  Asp  Ser  Ile  Lys  Lys  Tyr  Ile  Asn  Asp  Lys
     1385                1390                1395

Gln  Gly  Glu  Asn  Glu  Lys  Tyr  Leu  Pro  Phe  Leu  Asn  Asn  Ile  Glu
     1400                1405                1410

Thr  Leu  Tyr  Lys  Thr  Val  Asn  Asp  Lys  Ile  Asp  Leu  Phe  Val  Ile
     1415                1420                1425

His  Leu  Glu  Ala  Lys  Val  Leu  Asn  Tyr  Thr  Tyr  Glu  Lys  Ser  Asn
     1430                1435                1440

Val  Glu  Val  Lys  Ile  Lys  Glu  Leu  Asn  Tyr  Leu  Lys  Thr  Ile  Gln
     1445                1450                1455

Asp  Lys  Leu  Ala  Asp  Phe  Lys  Lys  Asn  Asn  Phe  Val  Gly  Ile
     1460                1465                1470

Ala  Asp  Leu  Ser  Thr  Asp  Tyr  Asn  His  Asn  Asn  Leu  Leu  Thr  Lys
     1475                1480                1485

Phe  Leu  Ser  Thr  Gly  Met  Val  Phe  Glu  Asn  Leu  Ala  Lys  Thr  Val
     1490                1495                1500

Leu  Ser  Asn  Leu  Leu  Asp  Gly  Asn  Leu  Gln  Gly  Met  Leu  Asn  Ile
     1505                1510                1515

Ser  Gln  His  Gln  Cys  Val  Lys  Lys  Gln  Cys  Pro  Gln  Asn  Ser  Gly
     1520                1525                1530

Cys  Phe  Arg  His  Leu  Asp  Glu  Arg  Glu  Cys  Lys  Cys  Leu  Leu
     1535                1540                1545

Asn  Tyr  Lys  Gln  Glu  Gly  Asp  Lys  Cys  Val  Glu  Asn  Pro  Asn  Pro
     1550                1555                1560

Thr  Cys  Asn  Glu  Asn  Asn  Gly  Gly  Cys  Asp  Ala  Asp  Ala  Lys  Cys
     1565                1570                1575

Thr  Glu  Glu  Asp  Ser  Gly  Ser  Asn  Gly  Lys  Lys  Ile  Thr  Cys  Glu
     1580                1585                1590

Cys  Thr  Lys  Pro  Asp  Ser  Tyr  Pro  Leu  Phe  Asp  Gly  Ile  Phe  Cys
     1595                1600                1605

Ser  Ser  Ser  Asn  Phe  Leu  Gly  Ile  Ser  Phe  Leu  Leu  Ile  Leu  Met
     1610                1615                1620

Leu  Ile  Leu  Tyr  Ser  Phe  Ile
     1625                1630

<210> SEQ ID NO 11
<211> LENGTH: 5363
<212> TYPE: DNA
<213> ORGANISM: Plasmodium vivax
<220> FEATURE:
<221> NAME/KEY: CDS
<222> LOCATION: (53)..(5314)
<220> FEATURE:
<221> NAME/KEY: sig_peptide
<222> LOCATION: (72)..(128)
<220> FEATURE:
<221> NAME/KEY: misc_feature
<222> LOCATION: (5243)..(5245)
<223> OTHER INFORMATION: predicted GPI-attachment site in encoded
      protein

<400> SEQUENCE: 11
gtgttcgtac atctttaaac cccacacact ttgattatta aattagacga at tcg aaa      58
                                                          Ser Lys
                                                           1
```

```
atg aag gcg cta ctc ttt ttg ttc tct ttc att ttt ttc gtt acc aaa    106
Met Lys Ala Leu Leu Phe Leu Phe Ser Phe Ile Phe Phe Val Thr Lys
              5                  10                  15 tgt caa tgt gaa aca gaa agt tat aag cag ctt gta gcc aag ctg gac    154
Cys Gln Cys Glu Thr Glu Ser Tyr Lys Gln Leu Val Ala Lys Leu Asp
 20                  25                  30 aag tta gag gcg ctc gtg gtg gac ggc tac gag ctc ttc cac aaa aaa    202
Lys Leu Glu Ala Leu Val Val Asp Gly Tyr Glu Leu Phe His Lys Lys
 35                  40                  45                  50 aag tta gga gaa aat gat att aag gta gaa acc aat gct agt gca aat    250
Lys Leu Gly Glu Asn Asp Ile Lys Val Glu Thr Asn Ala Ser Ala Asn
                     55                  60                  65 aat aat aat aac aat cag gtt agc gtt tta act tcc aaa ata aga aat    298
Asn Asn Asn Asn Asn Gln Val Ser Val Leu Thr Ser Lys Ile Arg Asn
             70                  75                  80 ttc ctg agc aag ttt ttg gag cta caa att cct gga cat acc gac ttg    346
Phe Leu Ser Lys Phe Leu Glu Leu Gln Ile Pro Gly His Thr Asp Leu
             85                  90                  95 cta cac ctg ata aga gaa ttg gcc gtg gaa ccc aat ggg ata aaa tac    394
Leu His Leu Ile Arg Glu Leu Ala Val Glu Pro Asn Gly Ile Lys Tyr
        100                 105                 110 ctt gtg gag agc tac gaa gaa ttc aat caa ctg atg cac gtg atc aac    442
Leu Val Glu Ser Tyr Glu Glu Phe Asn Gln Leu Met His Val Ile Asn
115                 120                 125                 130 ttc cac tat gat ttg ttg agg gcg aag ctc cac gac atg tgt gcc cat    490
Phe His Tyr Asp Leu Leu Arg Ala Lys Leu His Asp Met Cys Ala His
                    135                 140                 145 gat tat tgc aaa ata ccg gag cat cta aaa atc tct gac aaa gag ctg    538
Asp Tyr Cys Lys Ile Pro Glu His Leu Lys Ile Ser Asp Lys Glu Leu
            150                 155                 160 gac atg ctg aag aaa gtt gtg ctg ggt tat agg aag ccc ttg gac aac    586
Asp Met Leu Lys Lys Val Val Leu Gly Tyr Arg Lys Pro Leu Asp Asn
            165                 170                 175 ata aag gac gat att gga aaa ttg gag acc ttc atc act aaa aac aag    634
Ile Lys Asp Asp Ile Gly Lys Leu Glu Thr Phe Ile Thr Lys Asn Lys
        180                 185                 190 ata aca ata aaa aat ata agt gat tta att att gcg gag aac aag aaa    682
Ile Thr Ile Lys Asn Ile Ser Asp Leu Ile Ile Ala Glu Asn Lys Lys
195                 200                 205                 210 agg agt ggc cat ccc acc acc acg act aat gga gcc ggc acg caa ccc    730
Arg Ser Gly His Pro Thr Thr Thr Thr Asn Gly Ala Gly Thr Gln Pro
                    215                 220                 225 gct aat ggt tca att gcg gca gcc agt tcg gaa act act caa att tct    778
Ala Asn Gly Ser Ile Ala Ala Ala Ser Ser Glu Thr Thr Gln Ile Ser
            230                 235                 240 ggt tcg tct aac tct ggt tcg agt agc act ggt tcg tct aac tct ggt    826
Gly Ser Ser Asn Ser Gly Ser Ser Ser Thr Gly Ser Ser Asn Ser Gly
            245                 250                 255 tcg agt agc act ggt tcg agt ggc act ggt tcg act ggc act gga caa    874
Ser Ser Ser Thr Gly Ser Ser Gly Thr Gly Ser Thr Gly Thr Gly Gln
        260                 265                 270 tct cct cca gca gct gct gat gca tct tca aca aat gca aac tac gaa    922
Ser Pro Pro Ala Ala Ala Asp Ala Ser Ser Thr Asn Ala Asn Tyr Glu
275                 280                 285                 290 gcg aag aaa atc atc tac caa gcc gtg tac aac acc ata ttt tac acg    970
Ala Lys Lys Ile Ile Tyr Gln Ala Val Tyr Asn Thr Ile Phe Tyr Thr
                    295                 300                 305 aac cag ctg cag gaa gct caa aag tta atc gca gtc ctg gaa aag cgc    1018
Asn Gln Leu Gln Glu Ala Gln Lys Leu Ile Ala Val Leu Glu Lys Arg
            310                 315                 320
```

```
gtg aaa gtg ctg aag gag cac aaa gac att aag gtg cta ctc gaa cag      1066
Val Lys Val Leu Lys Glu His Lys Asp Ile Lys Val Leu Leu Glu Gln
        325                 330                 335 gtc gca aaa gaa aag gaa aag ctt cct agt gat tat ccc aac act aca      1114
Val Ala Lys Glu Lys Glu Lys Leu Pro Ser Asp Tyr Pro Asn Thr Thr
    340                 345                 350 aat ctt aca aat gta cac aaa gaa gcc gaa agc aaa att gcc gag ctc      1162
Asn Leu Thr Asn Val His Lys Glu Ala Glu Ser Lys Ile Ala Glu Leu
355                 360                 365                 370 gag aag aaa atc gaa gcc atc gcc aag act gtg aac ttc gac ctg gac      1210
Glu Lys Lys Ile Glu Ala Ile Ala Lys Thr Val Asn Phe Asp Leu Asp
                375                 380                 385 ggt ctg ttt act gac gca gag gag ttg gag tac tat ttg agg gag aag      1258
Gly Leu Phe Thr Asp Ala Glu Glu Leu Glu Tyr Tyr Leu Arg Glu Lys
            390                 395                 400 gca aag atg gcc ggc acg cta atc atc cca gaa agc acc aaa tca gca      1306
Ala Lys Met Ala Gly Thr Leu Ile Ile Pro Glu Ser Thr Lys Ser Ala
        405                 410                 415 ggc acc cct gga aag aca gtt cca acc ctg aaa gag acc tac cca cac      1354
Gly Thr Pro Gly Lys Thr Val Pro Thr Leu Lys Glu Thr Tyr Pro His
    420                 425                 430 gga ata agc tac gct tta gca gaa aac agt att tat gaa ctg ata gaa      1402
Gly Ile Ser Tyr Ala Leu Ala Glu Asn Ser Ile Tyr Glu Leu Ile Glu
435                 440                 445                 450 aaa att gga tct gat gaa aca ttt ggt gat ttg caa aat cca gat gat      1450
Lys Ile Gly Ser Asp Glu Thr Phe Gly Asp Leu Gln Asn Pro Asp Asp
                455                 460                 465 gga aag caa ccg aag aag gga atc ctc att aat gaa aca aag agg aaa      1498
Gly Lys Gln Pro Lys Lys Gly Ile Leu Ile Asn Glu Thr Lys Arg Lys
            470                 475                 480 gaa ttg ctg gaa aaa att atg aat aaa att aag ata gaa gaa gac aaa      1546
Glu Leu Leu Glu Lys Ile Met Asn Lys Ile Lys Ile Glu Glu Asp Lys
        485                 490                 495 ttg ccc aac cta aaa aaa gaa tac gag gaa aaa tat aag gtg tac gag      1594
Leu Pro Asn Leu Lys Lys Glu Tyr Glu Glu Lys Tyr Lys Val Tyr Glu
    500                 505                 510 gca aag gtt aat gag ttc aaa cca gca ttt aat cac ttt tat gag gca      1642
Ala Lys Val Asn Glu Phe Lys Pro Ala Phe Asn His Phe Tyr Glu Ala
515                 520                 525                 530 aga ctg gac aac acc ctt gtt gaa aac aaa ttt gat gat ttt aag aaa      1690
Arg Leu Asp Asn Thr Leu Val Glu Asn Lys Phe Asp Asp Phe Lys Lys
                535                 540                 545 aaa aga gag gca tat atg gag gag aag aaa aaa cta gaa agc tgc tcc      1738
Lys Arg Glu Ala Tyr Met Glu Glu Lys Lys Lys Leu Glu Ser Cys Ser
            550                 555                 560 tac gaa cag aac agc aat ctg att aac aag ctg aaa aaa caa cta aca      1786
Tyr Glu Gln Asn Ser Asn Leu Ile Asn Lys Leu Lys Lys Gln Leu Thr
        565                 570                 575 tac ttg gag gac tac gtt tta aga aaa gac atc gcc gac gat gaa att      1834
Tyr Leu Glu Asp Tyr Val Leu Arg Lys Asp Ile Ala Asp Asp Glu Ile
    580                 585                 590 aaa cac ttc agt ttc atg gag tgg aaa tta aag agc gaa att tat gat      1882
Lys His Phe Ser Phe Met Glu Trp Lys Leu Lys Ser Glu Ile Tyr Asp
595                 600                 605                 610 cta gcc cag gaa atc cga aaa aac gaa aac aag ctc acc att gaa aac      1930
Leu Ala Gln Glu Ile Arg Lys Asn Glu Asn Lys Leu Thr Ile Glu Asn
                615                 620                 625 aaa ttc gac ttc tcc ggg gtt gtg gaa tta caa gta caa aag gta ttg      1978
Lys Phe Asp Phe Ser Gly Val Val Glu Leu Gln Val Gln Lys Val Leu
            630                 635                 640
```

```
ata atc aaa aaa att gag gct cta aag aat gtc cag aat ctt ctt aag      2026
Ile Ile Lys Lys Ile Glu Ala Leu Lys Asn Val Gln Asn Leu Leu Lys
        645                 650                 655 aat gcc aag gtg aag gac gac ctg tac att cca aag gtg tat aag aca      2074
Asn Ala Lys Val Lys Asp Asp Leu Tyr Ile Pro Lys Val Tyr Lys Thr
660                 665                 670 agc gag aaa cct gag ccc tac tac ttg atg gtc ctc aaa agg gaa att      2122
Ser Glu Lys Pro Glu Pro Tyr Tyr Leu Met Val Leu Lys Arg Glu Ile
675                 680                 685                 690 gac aag ttg aag gac ttc atc ccc aaa atc gag agc atg atc gcc act      2170
Asp Lys Leu Lys Asp Phe Ile Pro Lys Ile Glu Ser Met Ile Ala Thr
                695                 700                 705 gag aag aac aag ccg acc gtg gca gcg gca gat ata gtg gca aag gga      2218
Glu Lys Asn Lys Pro Thr Val Ala Ala Ala Asp Ile Val Ala Lys Gly
        710                 715                 720 caa tcg ctt aga gga gca agt gaa aca ggg aca act ggc aat aca gtc      2266
Gln Ser Leu Arg Gly Ala Ser Glu Thr Gly Thr Thr Gly Asn Thr Val
        725                 730                 735 aat gcg caa aca gct gta gta caa cca caa cat caa gta gta aat gca      2314
Asn Ala Gln Thr Ala Val Val Gln Pro Gln His Gln Val Val Asn Ala
740                 745                 750 gta acg gta cag cct gga aca aca gga cat caa gca caa ggt gga gaa      2362
Val Thr Val Gln Pro Gly Thr Thr Gly His Gln Ala Gln Gly Gly Glu
755                 760                 765                 770 gca gaa aca caa aca aat tca gta caa gca caa gtt caa caa aca          2410
Ala Glu Thr Gln Thr Asn Ser Val Gln Ala Gln Val Gln Gln Thr
                775                 780                 785 cct gca gga gcg ggc gga cag gta gcc tca aca caa acg att agc caa      2458
Pro Ala Gly Ala Gly Gly Gln Val Ala Ser Thr Gln Thr Ile Ser Gln
        790                 795                 800 gcc cca gca cca act caa gcc tcc cca gaa cca gca cca gcc gcc cca      2506
Ala Pro Ala Pro Thr Gln Ala Ser Pro Glu Pro Ala Pro Ala Ala Pro
        805                 810                 815 cca tcg aca cct gct gcc gca gtt gct cca gca cca acc atg tcc aaa      2554
Pro Ser Thr Pro Ala Ala Ala Val Ala Pro Ala Pro Thr Met Ser Lys
820                 825                 830 ctg gaa tac ctc gaa aag ctc ctt gat ttt tta aaa tcc gct tac gca      2602
Leu Glu Tyr Leu Glu Lys Leu Leu Asp Phe Leu Lys Ser Ala Tyr Ala
835                 840                 845                 850 tgt cac aag cac att ttt gta acc aac tcc acc atg aaa aag gag cta      2650
Cys His Lys His Ile Phe Val Thr Asn Ser Thr Met Lys Lys Glu Leu
                855                 860                 865 ctc gat cag tac aaa ctt aac gct gat gag caa aac aaa att aac gaa      2698
Leu Asp Gln Tyr Lys Leu Asn Ala Asp Glu Gln Asn Lys Ile Asn Glu
        870                 875                 880 act aaa tgc gat gaa ttg gac ctc cta ttc aat gtc cag aac aac ttg      2746
Thr Lys Cys Asp Glu Leu Asp Leu Leu Phe Asn Val Gln Asn Asn Leu
        885                 890                 895 cca gcc atg tac tcc ata tat gac tct atg agc aac gaa ctg cag aac      2794
Pro Ala Met Tyr Ser Ile Tyr Asp Ser Met Ser Asn Glu Leu Gln Asn
900                 905                 910 ctt tac att gag ctg tac cag aag gaa atg gtt tac aat ata tac aag      2842
Leu Tyr Ile Glu Leu Tyr Gln Lys Glu Met Val Tyr Asn Ile Tyr Lys
915                 920                 925                 930 aac aag gac acg gac aag aag att aag gct ttc ctg gaa aca ctc aag      2890
Asn Lys Asp Thr Asp Lys Lys Ile Lys Ala Phe Leu Glu Thr Leu Lys
                935                 940                 945 agc aaa gcg gct gct cct gct cag tca gcg gca aaa ccc agc ggt caa      2938
Ser Lys Ala Ala Ala Pro Ala Gln Ser Ala Ala Lys Pro Ser Gly Gln
        950                 955                 960
```

```
gcg ggt act act cca gta acg aca act gcg cca gta acc aca aca aca         2986
Ala Gly Thr Thr Pro Val Thr Thr Thr Ala Pro Val Thr Thr Thr Thr
            965                 970                 975 gtt act cca agt ccc caa aca tca gtt gta aca agc aca cct cct aca         3034
Val Thr Pro Ser Pro Gln Thr Ser Val Val Thr Ser Thr Pro Pro Thr
        980                 985                 990 ccc caa gca gaa gaa aac cga cgc gtg gga ggt aac agc gag gag             3079
Pro Gln Ala Glu Glu Asn Arg Arg Val Gly Gly Asn Ser Glu Glu
995                 1000                1005 aaa ccc gaa gcc gac act gcg caa gtg gaa aag ttt tac gag aag             3124
Lys Pro Glu Ala Asp Thr Ala Gln Val Glu Lys Phe Tyr Glu Lys
1010                1015                1020 cac cta tcc caa att gac aag tac aac gac tat ttc cag aag ttc             3169
His Leu Ser Gln Ile Asp Lys Tyr Asn Asp Tyr Phe Gln Lys Phe
1025                1030                1035 ctt gaa tcc caa aaa gat gaa atc acc aaa atg gat gaa aca aag             3214
Leu Glu Ser Gln Lys Asp Glu Ile Thr Lys Met Asp Glu Thr Lys
1040                1045                1050 tgg aaa gca cta ggt gca gaa att gag gaa ctg aag aag aag cta             3259
Trp Lys Ala Leu Gly Ala Glu Ile Glu Glu Leu Lys Lys Lys Leu
1055                1060                1065 caa gta tct ctg gac cac tat gga aag tac aag ctc aaa ttg gag             3304
Gln Val Ser Leu Asp His Tyr Gly Lys Tyr Lys Leu Lys Leu Glu
1070                1075                1080 agg ctc ctc aaa aag aag aat aaa atc tct aac agc aag gat caa             3349
Arg Leu Leu Lys Lys Lys Asn Lys Ile Ser Asn Ser Lys Asp Gln
1085                1090                1095 att aaa aag ctc acc agt ttg aaa aac aaa ttg gag aga aga caa             3394
Ile Lys Lys Leu Thr Ser Leu Lys Asn Lys Leu Glu Arg Arg Gln
1100                1105                1110 aat ctg ttg aat aac cca aca agt gtg ttg aaa aat tac acc gct             3439
Asn Leu Leu Asn Asn Pro Thr Ser Val Leu Lys Asn Tyr Thr Ala
1115                1120                1125 ttt ttc aac aaa aag aga gaa aca gaa aag aag gag gtg gaa aat             3484
Phe Phe Asn Lys Lys Arg Glu Thr Glu Lys Lys Glu Val Glu Asn
1130                1135                1140 acc ctt aag aat acc gag att ttg ctg aag tac tat aag gca cga             3529
Thr Leu Lys Asn Thr Glu Ile Leu Leu Lys Tyr Tyr Lys Ala Arg
1145                1150                1155 gcc aaa tat tat ata gga gag ccc ttc cct ctg aag acc tta agt             3574
Ala Lys Tyr Tyr Ile Gly Glu Pro Phe Pro Leu Lys Thr Leu Ser
1160                1165                1170 gaa gaa tca atg cag aag gag gac aac tac ctc aac tta gaa aag             3619
Glu Glu Ser Met Gln Lys Glu Asp Asn Tyr Leu Asn Leu Glu Lys
1175                1180                1185 ttt aga gtg ctc agc aga ttg gaa gga aga tta gga aag aac atc             3664
Phe Arg Val Leu Ser Arg Leu Glu Gly Arg Leu Gly Lys Asn Ile
1190                1195                1200 gag ttg gaa aag gag aac ata agc tac ctg tcc agt gga ctg cac             3709
Glu Leu Glu Lys Glu Asn Ile Ser Tyr Leu Ser Ser Gly Leu His
1205                1210                1215 cac gtc ttg aca gag ctg aag gaa att atc aaa aac aag aaa tac             3754
His Val Leu Thr Glu Leu Lys Glu Ile Ile Lys Asn Lys Lys Tyr
1220                1225                1230 tcc ggt aac gac cac acg aag aac att gca gct gtt aag gaa gct             3799
Ser Gly Asn Asp His Thr Lys Asn Ile Ala Ala Val Lys Glu Ala
1235                1240                1245 ttg caa gcc tac caa gaa ttg atc ccc aag gtg acc act cag gaa             3844
Leu Gln Ala Tyr Gln Glu Leu Ile Pro Lys Val Thr Thr Gln Glu
1250                1255                1260
```

-continued

| | | |
|---|---|---|
| ggc gca tcc aca aca gcg gca aca tta cca gta aca gta cca tca<br>Gly Ala Ser Thr Thr Ala Ala Thr Leu Pro Val Thr Val Pro Ser<br>1265                    1270                    1275 | 3889 |
| gca gta cca gga gga tta cct gga gca gga gta cca gga gca gca<br>Ala Val Pro Gly Gly Leu Pro Gly Ala Gly Val Pro Gly Ala Ala<br>1280                    1285                    1290 | 3934 |
| gca gga cta aca cca cca cca gca gga tca gta cca gca aca<br>Ala Gly Leu Thr Pro Pro Pro Ala Gly Ser Val Pro Ala Thr<br>1295                    1300                    1305 | 3979 |
| gga cca gga gca gca gca gga tca aca gaa gaa aac gta gca gca<br>Gly Pro Gly Ala Ala Ala Gly Ser Thr Glu Glu Asn Val Ala Ala<br>1310                    1315                    1320 | 4024 |
| aaa gcg cag gac tac gcc gag gac tac gac aaa gta atc gca ctc<br>Lys Ala Gln Asp Tyr Ala Glu Asp Tyr Asp Lys Val Ile Ala Leu<br>1325                    1330                    1335 | 4069 |
| cct ctg ttc ggc aac aac gat gac gac ggg gag gaa gac caa gta<br>Pro Leu Phe Gly Asn Asn Asp Asp Asp Gly Glu Glu Asp Gln Val<br>1340                    1345                    1350 | 4114 |
| aca acg gga gag gca gaa tct gag gcg cct gag atc ctc gtg cca<br>Thr Thr Gly Glu Ala Glu Ser Glu Ala Pro Glu Ile Leu Val Pro<br>1355                    1360                    1365 | 4159 |
| gca gga atc agc gat tac gat gtg gtc tac tta aag cca tta gcc<br>Ala Gly Ile Ser Asp Tyr Asp Val Val Tyr Leu Lys Pro Leu Ala<br>1370                    1375                    1380 | 4204 |
| gga atg tac aaa acg ata aag aag caa ttg gaa aat cac gta aac<br>Gly Met Tyr Lys Thr Ile Lys Lys Gln Leu Glu Asn His Val Asn<br>1385                    1390                    1395 | 4249 |
| gca ttt aac act aac ata acg gat atg tta gac tct aga ctg aag<br>Ala Phe Asn Thr Asn Ile Thr Asp Met Leu Asp Ser Arg Leu Lys<br>1400                    1405                    1410 | 4294 |
| aag aga aac tac ttc tta gaa gtt ctg aac tct gat ttg aac cca<br>Lys Arg Asn Tyr Phe Leu Glu Val Leu Asn Ser Asp Leu Asn Pro<br>1415                    1420                    1425 | 4339 |
| ttt aag tat tca tca tct ggt gag tac atc att aag gac cca tac<br>Phe Lys Tyr Ser Ser Ser Gly Glu Tyr Ile Ile Lys Asp Pro Tyr<br>1430                    1435                    1440 | 4384 |
| aag ctg ctc gac ttg gag aag aag aag aag ctt ata ggc agc tac<br>Lys Leu Leu Asp Leu Glu Lys Lys Lys Lys Leu Ile Gly Ser Tyr<br>1445                    1450                    1455 | 4429 |
| aag tac atc ggt gca tcg atc gac atg gat ctg gcc acc gcg aat<br>Lys Tyr Ile Gly Ala Ser Ile Asp Met Asp Leu Ala Thr Ala Asn<br>1460                    1465                    1470 | 4474 |
| gat ggc gtg acc tac tac aac aag atg ggg gag ctc tac aag acg<br>Asp Gly Val Thr Tyr Tyr Asn Lys Met Gly Glu Leu Tyr Lys Thr<br>1475                    1480                    1485 | 4519 |
| cac ttg gat gga gtg aaa aca gag att aag aaa gtc gaa gat gat<br>His Leu Asp Gly Val Lys Thr Glu Ile Lys Lys Val Glu Asp Asp<br>1490                    1495                    1500 | 4564 |
| att aaa aag caa gat gag gaa ctt aaa aag tta gga aat gtt aac<br>Ile Lys Lys Gln Asp Glu Glu Leu Lys Lys Leu Gly Asn Val Asn<br>1505                    1510                    1515 | 4609 |
| agt caa gat agt aaa aag aac gaa ttt att gcc aaa aag gcc gag<br>Ser Gln Asp Ser Lys Lys Asn Glu Phe Ile Ala Lys Lys Ala Glu<br>1520                    1525                    1530 | 4654 |
| ctg gag aag tac ctc ccg ttc ctg aat agc ctc caa aag gag tac<br>Leu Glu Lys Tyr Leu Pro Phe Leu Asn Ser Leu Gln Lys Glu Tyr<br>1535                    1540                    1545 | 4699 |
| gag tcc ctc gtg agc aag gtg aac acc tac aca gac aac cta aaa<br>Glu Ser Leu Val Ser Lys Val Asn Thr Tyr Thr Asp Asn Leu Lys<br>1550                    1555                    1560 | 4744 |

-continued

```
aaa gtc atc aac aac tgc cag ctg gag aaa aag gaa gcc gag atc       4789
Lys Val Ile Asn Asn Cys Gln Leu Glu Lys Lys Glu Ala Glu Ile
1565                1570                1575 act gta aag aaa ttg cag gac tac aac aag atg gat gag aag ttg       4834
Thr Val Lys Lys Leu Gln Asp Tyr Asn Lys Met Asp Glu Lys Leu
1580                1585                1590 gag gag tac aaa aaa tcg gag aaa aaa aat gaa gtg aag tct tct       4879
Glu Glu Tyr Lys Lys Ser Glu Lys Lys Asn Glu Val Lys Ser Ser
1595                1600                1605 ggt ctt ctg gaa aaa ttg atg aaa tca aaa ttg att aaa gaa aac       4924
Gly Leu Leu Glu Lys Leu Met Lys Ser Lys Leu Ile Lys Glu Asn
1610                1615                1620 gag tcc aag gaa ata tta tcc cag ctg cta aat gtg caa act cag       4969
Glu Ser Lys Glu Ile Leu Ser Gln Leu Leu Asn Val Gln Thr Gln
1625                1630                1635 tta tta act atg agc tcc gag cac aca tgt ata gac acc aat gtg       5014
Leu Leu Thr Met Ser Ser Glu His Thr Cys Ile Asp Thr Asn Val
1640                1645                1650 cct gat aat gca gcc tgc tat agg tac ttg gac gga acg gaa gaa       5059
Pro Asp Asn Ala Ala Cys Tyr Arg Tyr Leu Asp Gly Thr Glu Glu
1655                1660                1665 tgg aga tgc ttg tta acc ttt aaa gaa gaa ggc ggc aag tgt gtg       5104
Trp Arg Cys Leu Leu Thr Phe Lys Glu Glu Gly Gly Lys Cys Val
1670                1675                1680 cca gca tcg aat gtg act tgt aag gat aac aat ggt ggt tgt gcc       5149
Pro Ala Ser Asn Val Thr Cys Lys Asp Asn Asn Gly Gly Cys Ala
1685                1690                1695 cct gaa gct gaa tgt aaa atg acg gac agc aat aaa atc gtc tgt       5194
Pro Glu Ala Glu Cys Lys Met Thr Asp Ser Asn Lys Ile Val Cys
1700                1705                1710 aaa tgt act aaa gaa ggt tct gag cca ctc ttt gag gga gtt ttc       5239
Lys Cys Thr Lys Glu Gly Ser Glu Pro Leu Phe Glu Gly Val Phe
1715                1720                1725 tgt agc tcc tcc agc ttc cta agc ttg tcc ttc ttg ttg ctc atg       5284
Cys Ser Ser Ser Ser Phe Leu Ser Leu Ser Phe Leu Leu Leu Met
1730                1735                1740 ttg ctt ttc ctc ctg tgc atg gag ctt taa aaataacaca aataaaagtg     5334
Leu Leu Phe Leu Leu Cys Met Glu Leu
1745                1750 cagcaagtgc agcggcgcca cgtgcaatt                                   5363

<210> SEQ ID NO 12
<211> LENGTH: 1753
<212> TYPE: PRT
<213> ORGANISM: Plasmodium vivax

<400> SEQUENCE: 12

Ser Lys Met Lys Ala Leu Leu Phe Leu Phe Ser Phe Ile Phe Phe Val
1               5                   10                  15

Thr Lys Cys Gln Cys Glu Thr Glu Ser Tyr Lys Gln Leu Val Ala Lys
            20                  25                  30

Leu Asp Lys Leu Glu Ala Leu Val Val Asp Gly Tyr Glu Leu Phe His
        35                  40                  45

Lys Lys Lys Leu Gly Glu Asn Asp Ile Lys Val Glu Thr Asn Ala Ser
    50                  55                  60

Ala Asn Asn Asn Asn Asn Gln Val Ser Val Leu Thr Ser Lys Ile
65                  70                  75                  80

Arg Asn Phe Leu Ser Lys Phe Leu Glu Leu Gln Ile Pro Gly His Thr
                85                  90                  95
```

```
Asp Leu Leu His Leu Ile Arg Glu Leu Ala Val Glu Pro Asn Gly Ile
            100                 105                 110

Lys Tyr Leu Val Glu Ser Tyr Glu Glu Phe Asn Gln Leu Met His Val
        115                 120                 125

Ile Asn Phe His Tyr Asp Leu Leu Arg Ala Lys Leu His Asp Met Cys
    130                 135                 140

Ala His Asp Tyr Cys Lys Ile Pro Glu His Leu Lys Ile Ser Asp Lys
145                 150                 155                 160

Glu Leu Asp Met Leu Lys Lys Val Val Leu Gly Tyr Arg Lys Pro Leu
                165                 170                 175

Asp Asn Ile Lys Asp Asp Ile Gly Lys Leu Glu Thr Phe Ile Thr Lys
            180                 185                 190

Asn Lys Ile Thr Ile Lys Asn Ile Ser Asp Leu Ile Ile Ala Glu Asn
        195                 200                 205

Lys Lys Arg Ser Gly His Pro Thr Thr Thr Thr Asn Gly Ala Gly Thr
    210                 215                 220

Gln Pro Ala Asn Gly Ser Ile Ala Ala Ser Ser Glu Thr Thr Gln
225                 230                 235                 240

Ile Ser Gly Ser Ser Asn Ser Gly Ser Ser Ser Thr Gly Ser Ser Asn
                245                 250                 255

Ser Gly Ser Ser Ser Thr Gly Ser Ser Gly Thr Gly Ser Thr Gly Thr
            260                 265                 270

Gly Gln Ser Pro Pro Ala Ala Ala Asp Ala Ser Ser Thr Asn Ala Asn
        275                 280                 285

Tyr Glu Ala Lys Lys Ile Ile Tyr Gln Ala Val Tyr Asn Thr Ile Phe
    290                 295                 300

Tyr Thr Asn Gln Leu Gln Glu Ala Gln Lys Leu Ile Ala Val Leu Glu
305                 310                 315                 320

Lys Arg Val Lys Val Leu Lys Glu His Lys Asp Ile Lys Val Leu Leu
                325                 330                 335

Glu Gln Val Ala Lys Glu Lys Glu Lys Leu Pro Ser Asp Tyr Pro Asn
            340                 345                 350

Thr Thr Asn Leu Thr Asn Val His Lys Glu Ala Glu Ser Lys Ile Ala
        355                 360                 365

Glu Leu Glu Lys Lys Ile Glu Ala Ile Ala Lys Thr Val Asn Phe Asp
    370                 375                 380

Leu Asp Gly Leu Phe Thr Asp Ala Glu Glu Leu Glu Tyr Tyr Leu Arg
385                 390                 395                 400

Glu Lys Ala Lys Met Ala Gly Thr Leu Ile Ile Pro Glu Ser Thr Lys
                405                 410                 415

Ser Ala Gly Thr Pro Gly Lys Thr Val Pro Thr Leu Lys Glu Thr Tyr
            420                 425                 430

Pro His Gly Ile Ser Tyr Ala Leu Ala Glu Asn Ser Ile Tyr Glu Leu
        435                 440                 445

Ile Glu Lys Ile Gly Ser Asp Glu Thr Phe Gly Asp Leu Gln Asn Pro
    450                 455                 460

Asp Asp Gly Lys Gln Pro Lys Lys Gly Ile Leu Ile Asn Glu Thr Lys
465                 470                 475                 480

Arg Lys Glu Leu Leu Glu Lys Ile Met Asn Lys Ile Lys Ile Glu Glu
                485                 490                 495

Asp Lys Leu Pro Asn Leu Lys Lys Glu Tyr Glu Glu Lys Tyr Lys Val
            500                 505                 510

Tyr Glu Ala Lys Val Asn Glu Phe Lys Pro Ala Phe Asn His Phe Tyr
```

-continued

```
              515                 520                 525
Glu Ala Arg Leu Asp Asn Thr Leu Val Glu Asn Lys Phe Asp Asp Phe
            530                 535                 540
Lys Lys Lys Arg Glu Ala Tyr Met Glu Lys Lys Lys Leu Glu Ser
545                 550                 555                 560
Cys Ser Tyr Glu Gln Asn Ser Asn Leu Ile Asn Lys Leu Lys Lys Gln
                565                 570                 575
Leu Thr Tyr Leu Glu Asp Tyr Val Leu Arg Lys Asp Ile Ala Asp Asp
            580                 585                 590
Glu Ile Lys His Phe Ser Phe Met Glu Trp Lys Leu Lys Ser Glu Ile
        595                 600                 605
Tyr Asp Leu Ala Gln Glu Ile Arg Lys Asn Glu Asn Lys Leu Thr Ile
    610                 615                 620
Glu Asn Lys Phe Asp Phe Ser Gly Val Val Glu Leu Gln Val Gln Lys
625                 630                 635                 640
Val Leu Ile Ile Lys Lys Ile Glu Ala Leu Lys Asn Val Gln Asn Leu
                645                 650                 655
Leu Lys Asn Ala Lys Val Lys Asp Asp Leu Tyr Ile Pro Lys Val Tyr
            660                 665                 670
Lys Thr Ser Glu Lys Pro Glu Pro Tyr Tyr Leu Met Val Leu Lys Arg
        675                 680                 685
Glu Ile Asp Lys Leu Lys Asp Phe Ile Pro Lys Ile Glu Ser Met Ile
    690                 695                 700
Ala Thr Glu Lys Asn Lys Pro Thr Val Ala Ala Ala Asp Ile Val Ala
705                 710                 715                 720
Lys Gly Gln Ser Leu Arg Gly Ala Ser Glu Thr Gly Thr Thr Gly Asn
                725                 730                 735
Thr Val Asn Ala Gln Thr Ala Val Val Gln Pro Gln His Gln Val Val
            740                 745                 750
Asn Ala Val Thr Val Gln Pro Gly Thr Thr Gly His Gln Ala Gln Gly
        755                 760                 765
Gly Glu Ala Glu Thr Gln Thr Asn Ser Val Gln Ala Ala Gln Val Gln
770                 775                 780
Gln Thr Pro Ala Gly Ala Gly Gly Gln Val Ala Ser Thr Gln Thr Ile
785                 790                 795                 800
Ser Gln Ala Pro Ala Pro Thr Gln Ala Ser Pro Glu Pro Ala Pro Ala
                805                 810                 815
Ala Pro Pro Ser Thr Pro Ala Ala Val Ala Pro Ala Pro Thr Met
            820                 825                 830
Ser Lys Leu Glu Tyr Leu Glu Lys Leu Leu Asp Phe Leu Lys Ser Ala
        835                 840                 845
Tyr Ala Cys His Lys His Ile Phe Val Thr Asn Ser Thr Met Lys Lys
    850                 855                 860
Glu Leu Leu Asp Gln Tyr Lys Leu Asn Ala Asp Glu Gln Asn Lys Ile
865                 870                 875                 880
Asn Glu Thr Lys Cys Asp Glu Leu Asp Leu Leu Phe Asn Val Gln Asn
                885                 890                 895
Asn Leu Pro Ala Met Tyr Ser Ile Tyr Asp Ser Met Ser Asn Glu Leu
            900                 905                 910
Gln Asn Leu Tyr Ile Glu Leu Tyr Gln Lys Glu Met Val Tyr Asn Ile
        915                 920                 925
Tyr Lys Asn Lys Asp Thr Asp Lys Lys Ile Lys Ala Phe Leu Glu Thr
    930                 935                 940
```

-continued

```
Leu Lys Ser Lys Ala Ala Ala Pro Ala Gln Ser Ala Ala Lys Pro Ser
945                 950                 955                 960

Gly Gln Ala Gly Thr Thr Pro Val Thr Thr Thr Ala Pro Val Thr Thr
                965                 970                 975

Thr Thr Val Thr Pro Ser Pro Gln Thr Ser Val Val Thr Ser Thr Pro
            980                 985                 990

Pro Thr Pro Gln Ala Glu Glu Asn Arg Arg Val Gly Gly Asn Ser Glu
        995                 1000                1005

Glu Lys Pro Glu Ala Asp Thr Ala Gln Val Glu Lys Phe Tyr Glu
    1010                1015                1020

Lys His Leu Ser Gln Ile Asp Lys Tyr Asn Asp Tyr Phe Gln Lys
    1025                1030                1035

Phe Leu Glu Ser Gln Lys Asp Glu Ile Thr Lys Met Asp Glu Thr
    1040                1045                1050

Lys Trp Lys Ala Leu Gly Ala Glu Ile Glu Glu Leu Lys Lys Lys
    1055                1060                1065

Leu Gln Val Ser Leu Asp His Tyr Gly Lys Tyr Lys Leu Lys Leu
    1070                1075                1080

Glu Arg Leu Leu Lys Lys Asn Lys Ile Ser Asn Ser Lys Asp
    1085                1090                1095

Gln Ile Lys Lys Leu Thr Ser Leu Lys Asn Lys Leu Glu Arg Arg
    1100                1105                1110

Gln Asn Leu Leu Asn Pro Thr Ser Val Leu Lys Asn Tyr Thr
    1115                1120                1125

Ala Phe Phe Asn Lys Lys Arg Glu Thr Glu Lys Lys Glu Val Glu
    1130                1135                1140

Asn Thr Leu Lys Asn Thr Glu Ile Leu Leu Lys Tyr Tyr Lys Ala
    1145                1150                1155

Arg Ala Lys Tyr Tyr Ile Gly Glu Pro Phe Pro Leu Lys Thr Leu
    1160                1165                1170

Ser Glu Glu Ser Met Gln Lys Glu Asp Asn Tyr Leu Asn Leu Glu
    1175                1180                1185

Lys Phe Arg Val Leu Ser Arg Leu Glu Gly Arg Leu Gly Lys Asn
    1190                1195                1200

Ile Glu Leu Glu Lys Glu Asn Ile Ser Tyr Leu Ser Ser Gly Leu
    1205                1210                1215

His His Val Leu Thr Glu Leu Lys Glu Ile Ile Lys Asn Lys Lys
    1220                1225                1230

Tyr Ser Gly Asn Asp His Thr Lys Asn Ile Ala Ala Val Lys Glu
    1235                1240                1245

Ala Leu Gln Ala Tyr Gln Glu Leu Ile Pro Lys Val Thr Thr Gln
    1250                1255                1260

Glu Gly Ala Ser Thr Thr Ala Ala Thr Leu Pro Val Thr Val Pro
    1265                1270                1275

Ser Ala Val Pro Gly Gly Leu Pro Gly Ala Gly Val Pro Gly Ala
    1280                1285                1290

Ala Ala Gly Leu Thr Pro Pro Pro Ala Gly Ser Val Pro Ala
    1295                1300                1305

Thr Gly Pro Gly Ala Ala Ala Gly Ser Thr Glu Glu Asn Val Ala
    1310                1315                1320

Ala Lys Ala Gln Asp Tyr Ala Glu Asp Tyr Asp Lys Val Ile Ala
    1325                1330                1335

Leu Pro Leu Phe Gly Asn Asn Asp Asp Asp Gly Glu Glu Asp Gln
    1340                1345                1350
```

```
Val Thr Thr Gly Glu Ala Glu Ser Glu Ala Pro Glu Ile Leu Val
    1355                1360                1365

Pro Ala Gly Ile Ser Asp Tyr Asp Val Val Tyr Leu Lys Pro Leu
    1370                1375                1380

Ala Gly Met Tyr Lys Thr Ile Lys Lys Gln Leu Glu Asn His Val
    1385                1390                1395

Asn Ala Phe Asn Thr Asn Ile Thr Asp Met Leu Asp Ser Arg Leu
    1400                1405                1410

Lys Lys Arg Asn Tyr Phe Leu Glu Val Leu Asn Ser Asp Leu Asn
    1415                1420                1425

Pro Phe Lys Tyr Ser Ser Ser Gly Glu Tyr Ile Ile Lys Asp Pro
    1430                1435                1440

Tyr Lys Leu Leu Asp Leu Glu Lys Lys Lys Lys Leu Ile Gly Ser
    1445                1450                1455

Tyr Lys Tyr Ile Gly Ala Ser Ile Asp Met Asp Leu Ala Thr Ala
    1460                1465                1470

Asn Asp Gly Val Thr Tyr Tyr Asn Lys Met Gly Glu Leu Tyr Lys
    1475                1480                1485

Thr His Leu Asp Gly Val Lys Thr Glu Ile Lys Lys Val Glu Asp
    1490                1495                1500

Asp Ile Lys Lys Gln Asp Glu Glu Leu Lys Lys Leu Gly Asn Val
    1505                1510                1515

Asn Ser Gln Asp Ser Lys Lys Asn Glu Phe Ile Ala Lys Lys Ala
    1520                1525                1530

Glu Leu Glu Lys Tyr Leu Pro Phe Leu Asn Ser Leu Gln Lys Glu
    1535                1540                1545

Tyr Glu Ser Leu Val Ser Lys Val Asn Thr Tyr Thr Asp Asn Leu
    1550                1555                1560

Lys Lys Val Ile Asn Asn Cys Gln Leu Glu Lys Lys Glu Ala Glu
    1565                1570                1575

Ile Thr Val Lys Lys Leu Gln Asp Tyr Asn Lys Met Asp Glu Lys
    1580                1585                1590

Leu Glu Glu Tyr Lys Lys Ser Glu Lys Lys Asn Glu Val Lys Ser
    1595                1600                1605

Ser Gly Leu Leu Glu Lys Leu Met Lys Ser Lys Leu Ile Lys Glu
    1610                1615                1620

Asn Glu Ser Lys Glu Ile Leu Ser Gln Leu Leu Asn Val Gln Thr
    1625                1630                1635

Gln Leu Leu Thr Met Ser Ser Glu His Thr Cys Ile Asp Thr Asn
    1640                1645                1650

Val Pro Asp Asn Ala Ala Cys Tyr Arg Tyr Leu Asp Gly Thr Glu
    1655                1660                1665

Glu Trp Arg Cys Leu Leu Thr Phe Lys Glu Glu Gly Gly Lys Cys
    1670                1675                1680

Val Pro Ala Ser Asn Val Thr Cys Lys Asp Asn Asn Gly Gly Cys
    1685                1690                1695

Ala Pro Glu Ala Glu Cys Lys Met Thr Asp Ser Asn Lys Ile Val
    1700                1705                1710

Cys Lys Cys Thr Lys Glu Gly Ser Glu Pro Leu Phe Glu Gly Val
    1715                1720                1725

Phe Cys Ser Ser Ser Ser Leu Ser Leu Ser Phe Leu Leu Leu
    1730                1735                1740

Met Leu Leu Phe Leu Leu Cys Met Glu Leu
```

-continued

```
               1745               1750
```

<210> SEQ ID NO 13
<211> LENGTH: 20
<212> TYPE: PRT
<213> ORGANISM: Artificial
<220> FEATURE:
<223> OTHER INFORMATION: N-terminal sequence of pET-15b expression
      vector including 6-His tag

<400> SEQUENCE: 13

Met Gly Ser Ser His His His His His His Ser Ser Gly Val Pro Arg
1               5                   10                  15

Gly Ser His Met
            20

<210> SEQ ID NO 14
<211> LENGTH: 24
<212> TYPE: DNA
<213> ORGANISM: Artificial
<220> FEATURE:
<223> OTHER INFORMATION: chemically synthesized

<400> SEQUENCE: 14
gaacatatgc cagaaaaaga tatt                                          24

<210> SEQ ID NO 15
<211> LENGTH: 24
<212> TYPE: DNA
<213> ORGANISM: Artificial
<220> FEATURE:
<223> OTHER INFORMATION: chemically synthesized

<400> SEQUENCE: 15
tgaggatccc atttagctgg aaga                                          24

<210> SEQ ID NO 16
<211> LENGTH: 30
<212> TYPE: DNA
<213> ORGANISM: Artificial
<220> FEATURE:
<223> OTHER INFORMATION: chemically synthesized

<400> SEQUENCE: 16
cccgaattca catagcctca atagctttaa                                    30

<210> SEQ ID NO 17
<211> LENGTH: 24
<212> TYPE: DNA
<213> ORGANISM: Artificial
<220> FEATURE:
<223> OTHER INFORMATION: chemically synthesized

<400> SEQUENCE: 17
cccgaattct cccataaagc tgga                                          24

<210> SEQ ID NO 18
<211> LENGTH: 35
<212> TYPE: DNA
<213> ORGANISM: Artificial
<220> FEATURE:
<223> OTHER INFORMATION: chemically synthesized

<400> SEQUENCE: 18
atggatccat aactatactt aatttagcaa atggt                              35

```
<210> SEQ ID NO 19
<211> LENGTH: 33
<212> TYPE: DNA
<213> ORGANISM: Artificial
<220> FEATURE:
<223> OTHER INFORMATION: chemically synthesized

<400> SEQUENCE: 19
gggaattcaa cttgaacaat aaataccatc tcc                                33

<210> SEQ ID NO 20
<211> LENGTH: 33
<212> TYPE: DNA
<213> ORGANISM: Artificial
<220> FEATURE:
<223> OTHER INFORMATION: chemically synthesized

<400> SEQUENCE: 20
gcccatatgc acatagcctc aatagcttta aac                                33

<210> SEQ ID NO 21
<211> LENGTH: 41
<212> TYPE: DNA
<213> ORGANISM: Artificial
<220> FEATURE:
<223> OTHER INFORMATION: chemically synthesized

<400> SEQUENCE: 21
cccatatgac caccaccacc tcccataaag ctggaagaac t                       41

<210> SEQ ID NO 22
<211> LENGTH: 1596
<212> TYPE: DNA
<213> ORGANISM: Artificial
<220> FEATURE:
<223> OTHER INFORMATION: coding sequence for recombinant PyuMSP-1/8
      chimeric antigen

<400> SEQUENCE: 22
atgggcagca gccatcatca tcatcatcac agcagcggcc tggtgccgcg cggcagccat     60
atgcacatag cctcaatagc tttaaacaac ttaaataaat ctggtttagt aggagaaggt    120
gaatcaaaga aaatattagc aaaaatgctt aacatggatg gtatggattt attaggtgta    180
gaccctaaac atgtatgtgt tgatacaaga gatattccta aaaatgctgg atgttttaga    240
gatgataatg gtactgaaga atggagatgt ttattaggtt acaaaaaagg tgaaggtaat    300
acatgtgtag aaaataataa tcctacttgt gatatcaaca atggtggatg tgatccaact    360
gctagttgtc aaaatgcgga aagtacggaa aattccaaaa aaattatatg tacatgtaaa    420
gaaccaaccc ctaatgcata ttatgaaggt gtattctgta gttcttccag ctttatggga    480
ggtggtggtg gtcatatggg gaattgtaat gaaaatggaa acggtaatat aaataaagcc    540
aataataata gtaataataag aaaagaaaga aaaagaaaaa gtaaagtga ttttagtaaa    600 ggggaacctg aaaataagga acatgaaatt attaatttat atgatgatgt gcaagaatta    660
ttaggacccg acgaaatgaa tatgttagac aaatattcaa tattaggaat agatgattgt    720
tctaatgaaa atgaaaataa taaataatt agcgaatatg atcttaaagc aatgaagagt    780
gtattattat ataaaaaccg aatatcaaga gcatcaataa acaatttaga tgatgttaaa    840
actgtattta aagatgtttt taataaggat gatcctgaat taagtaaaag ttatgaacaa    900
atccaaaacc aagtagctaa cgaaggaaca actataatag attatttatc aaattatatt    960
tcaaatattt atattaaaat aaatgatgaa tttgtaaaaa atgaagaatt tcaactatca   1020
```

```
aaatatattc ctgaacttga aataattaat tatgtacttt ataatggacc taagaaata      1080 ggaaacaaaa taaaaatga attaatcgaa ataaataatt taataatatc tgaatctctt      1140
acctcaatat atagttctgt tgtttcaggg ttaaatataa attgtaaaat taagatgat      1200 ttaataacta tacttaattt agcaaatggt aaatatttta agtaaattt tagtagtcaa      1260 gctacaatga ttattcctga gcaatattct catgaatctg agcacatgaa aaaatatca      1320 gaatatttta ttgaaaaaaa tcgagtttgt aaaaatgaga actgtccaat caattcaaat      1380
tgttatgtta ttgatagtgt agaaacttgt agatgtattc caggattttc taaaaatgaa      1440
gaaagcgaaa atttagaatg tttaataaat gaatctactt cttgtgaaaa taataatggt      1500
ggatgtgatg taaatgcaaa ttgtatatta ttagaagata aaataatgtg tgaatgtaat      1560
aacaaattta atggagatgg tatttattgt tcatga                              1596
```

<210> SEQ ID NO 23
<211> LENGTH: 531
<212> TYPE: PRT
<213> ORGANISM: Artificial
<220> FEATURE:
<223> OTHER INFORMATION: recombinant PyMSP-1/8 chimeric antigen
<220> FEATURE:
<221> NAME/KEY: MISC_FEATURE
<222> LOCATION: (22)..(160)
<223> OTHER INFORMATION: residues 1619-1757 of P. yoelli MSP-1
<220> FEATURE:
<221> NAME/KEY: MISC_FEATURE
<222> LOCATION: (167)..(531)
<223> OTHER INFORMATION: residues 22-386 of P. yoelli MSP-8

<400> SEQUENCE: 23

```
Met Gly Ser Ser His His His His His His Ser Ser Gly Leu Val Pro
1               5                   10                  15

Arg Gly Ser His Met His Ile Ala Ser Ile Ala Leu Asn Asn Leu Asn
            20                  25                  30

Lys Ser Gly Leu Val Gly Glu Gly Glu Ser Lys Lys Ile Leu Ala Lys
        35                  40                  45

Met Leu Asn Met Asp Gly Met Asp Leu Leu Gly Val Asp Pro Lys His
    50                  55                  60

Val Cys Val Asp Thr Arg Asp Ile Pro Lys Asn Ala Gly Cys Phe Arg
65                  70                  75                  80

Asp Asp Asn Gly Thr Glu Glu Trp Arg Cys Leu Leu Gly Tyr Lys Lys
                85                  90                  95

Gly Glu Gly Asn Thr Cys Val Gly Asn Asn Pro Thr Cys Asp Ile
            100                 105                 110

Asn Asn Gly Gly Cys Asp Pro Thr Ala Ser Cys Gln Asn Ala Glu Ser
        115                 120                 125

Thr Glu Asn Ser Lys Lys Ile Ile Cys Thr Cys Lys Glu Pro Thr Pro
    130                 135                 140

Asn Ala Tyr Tyr Glu Gly Val Phe Cys Ser Ser Ser Phe Met Gly
145                 150                 155                 160

Gly Gly Gly Gly His Met Gly Asn Cys Asn Glu Asn Gly Asn Gly Asn
                165                 170                 175

Ile Asn Lys Ala Asn Asn Asn Ser Ile Ile Arg Lys Glu Arg Lys Arg
            180                 185                 190

Lys Ser Lys Ser Asp Phe Ser Lys Gly Glu Pro Glu Asn Lys Glu His
        195                 200                 205

Glu Ile Ile Asn Leu Tyr Asp Asp Val Gln Glu Leu Leu Gly Pro Asp
    210                 215                 220
```

```
Glu Met Asn Met Leu Asp Lys Tyr Ser Ile Leu Gly Ile Asp Asp Cys
225                 230                 235                 240

Ser Asn Glu Asn Glu Asn Asn Lys Ile Ile Ser Glu Tyr Asp Leu Lys
                245                 250                 255

Ala Met Lys Ser Val Leu Leu Tyr Lys Asn Arg Ile Ser Arg Ala Ser
                260                 265                 270

Ile Asn Asn Leu Asp Asp Val Lys Thr Val Phe Lys Arg Cys Phe Asn
                275                 280                 285

Lys Asp Asp Pro Glu Leu Ser Lys Ser Tyr Glu Gln Ile Gln Asn Gln
                290                 295                 300

Val Ala Asn Glu Gly Thr Thr Ile Ile Asp Tyr Leu Ser Asn Tyr Ile
305                 310                 315                 320

Ser Asn Ile Tyr Ile Lys Ile Asn Asp Glu Phe Val Lys Asn Glu Glu
                325                 330                 335

Phe Gln Leu Ser Lys Tyr Ile Pro Glu Leu Glu Ile Ile Asn Tyr Val
                340                 345                 350

Leu Tyr Asn Gly Pro Lys Glu Ile Gly Asn Lys Ile Lys Asn Glu Leu
                355                 360                 365

Ile Glu Ile Asn Asn Leu Ile Ile Ser Glu Ser Leu Thr Ser Ile Tyr
370                 375                 380

Ser Ser Val Val Ser Gly Leu Asn Ile Asn Cys Lys Ile Lys Asp Asp
385                 390                 395                 400

Leu Ile Thr Ile Leu Asn Leu Ala Asn Gly Lys Tyr Phe Lys Val Asn
                405                 410                 415

Phe Ser Ser Gln Ala Thr Met Ile Ile Pro Glu Gln Tyr Ser His Glu
                420                 425                 430

Ser Glu His Met Lys Lys Ile Ser Glu Tyr Phe Ile Glu Lys Asn Arg
                435                 440                 445

Val Cys Lys Asn Glu Asn Cys Pro Ile Asn Ser Asn Cys Tyr Val Ile
450                 455                 460

Asp Ser Val Glu Thr Cys Arg Cys Ile Pro Gly Phe Ser Lys Asn Glu
465                 470                 475                 480

Glu Ser Glu Asn Leu Glu Cys Leu Ile Asn Glu Ser Thr Ser Cys Glu
                485                 490                 495

Asn Asn Asn Gly Gly Cys Asp Val Asn Ala Asn Cys Ile Leu Leu Glu
                500                 505                 510

Asp Lys Ile Met Cys Glu Cys Asn Asn Lys Phe Asn Gly Asp Gly Ile
                515                 520                 525

Tyr Cys Ser
        530
```

CHIMERIC MSP-BASED MALARIA VACCINE

CROSS-REFERENCE TO RELATED APPLICATIONS

This Application is divisional of U.S. patent application Ser. No. 12/070,874, filed Feb. 21, 2008, which claims priority under 35 U.S.C. 119(e) to U.S. Provisional Patent Application No. 60/903,210, filed Feb. 23, 2007, all of which are herein incorporated by reference in their entirety.

STATEMENT REGARDING FEDERALLY SPONSORED RESEARCH OR DEVELOPMENT

This invention was made with government support under Grant Number ROIA135661 awarded by the NIH-National Institute of Allergy and Infectious Diseases. The government has certain rights in the invention.

BACKGROUND OF THE INVENTION

Malaria is a mosquito-borne disease caused by a parasite. *Plasmodium falciparum* and *Plasmodium vivax* are the two predominant human malaria parasites. Although malaria was eliminated as a major public health problem in the United States in the late 1940's, it remains a major health problem in developing countries. Each year, 350-500 million cases of malaria occur worldwide and over one million people die, most of them young children in sub-Saharan Africa. Malaria also takes a high toll on pregnant women.

In nature, malaria parasites spread by infecting successively two types of hosts: a vertebrate host (humans) and an invertebrate host (female Anopheles mosquitoes). Malarial parasites enter a human when an infected female mosquito feeds. The parasites, which are called sporozoites at this stage, migrate to the liver where they grow and multiply in hepatocytes, and are released as merozoites. Merozoites infect erythrocytes, where they develop and multiply. In the erythrocytic cycle, the parasite progresses through a series of blood stages (ring stage, trophozoite, and schizont). In the schizont stage, the infected erythrocyte lyses, releasing the multiplied population of merozoites, which then infect new erythrocytes. Some parasites in erythrocytes mature into reproductive gameotcytes that are ingested by a feeding mosquito. In the insect gut, the gametocytes develop into oocysts that grow, rupture and release sporozoites that migrate to the mosquito's salivary glands, thus completing the cycle.

Clinical disease occurs when parasites invade and replicate within host erythrocytes, a process which may lead to life-threatening complications, including severe anemia, splenic rupture, cerebral malaria, respiratory distress, and/or renal failure. Morbidity and mortality result during the asexual development and replication of *P. falciparum* or *P. vivax* parasites within erythrocytes (Miller et al., 2002, Nature 415: 673-679). While malaria is generally curable if diagnosed promptly and treated correctly, and there are medications available for prophylactic treatment, malaria remains a leading cause of death and disease in many developing countries. In addition, drug-resistant malaria strains are increasing. Thus, the need for a effective malaria vaccine is high.

The intraerythrocytic parasites are somewhat shielded from many cell-mediated and antibody-mediated immune effector mechanisms, and naturally acquired immunity is slow to develop. When the intracellular parasite matures and the host erythrocyte is lysed, the merozoites released are accessible to serum immunoglobulins before they invade new red blood cells (RBCs). While neutralization of free merozoites can occur, plasmodial parasites have also evolved mechanisms to avoid invasion-inhibiting antibodies. There are several alternate invasion pathways that depend on complex interactions between sets of several merozoite proteins and several host erythrocyte receptors (Barnwell et al., 1998, Invasion of vertebrate cells: erythrocytes, p. 93-120. In I. W. Sherman (ed.), Malaria: parasite biology, pathogenesis, and protection. ASM Press, Washington, D.C.; Berzins, 2002, Chem. Immunol. 80:125-143; Dolan et al., 1990, J. Clin. Invest. 86:618-624; Hadley et al., 1987, J. Clin. Invest, 80:1190-1193; Mitchell et al., 1986, Blood 67:1519-1521; Sim et al., 1994, Science 264:1941-1944). This redundancy of invasion pathways enables invasion to occur, even if one receptor-ligand interaction is blocked. In addition, merozoite-neutralizing antibodies are often strain specific due to a significant degree of polymorphism in many merozoite surface antigens (Barnwell et al., 1998, Invasion of vertebrate cells: erythrocytes, p. 93-120. In I. W. Sherman (ed.), Malaria: parasite biology, pathogenesis, and protection. ASM Press, Washington, D.C.; Berzins, 2002, Chem. Immunol. 80:125-143; Holder, 1996, Preventing merozoite invasion of erythrocytes, p. 77-104. In S. L. Hoffman (ed.), Malaria vaccine development: a multi-immune response approach. ASM Press, Washington, D.C.).

Several malaria vaccine strategies, which target pre-erythrocytic surface proteins, liver stage antigens and/or blood stage antigens, are currently being pursued (Heppner et al., 2005, Vaccine 23: 2243-2250; Mahanty et al., 2003, J. Exp. Biol. 206: 3781-3788; Richie et al., 2002, Nature 415: 694-701). The goal of blood-stage vaccines is to reduce parasite load and/or prevent life-threatening complications of malaria once parasites are replicating within red blood cells (RBCs). The single, most feasible strategy for blood-stage malaria is to immunize the host with subunit vaccines that induce high titers of antibodies that neutralize extracellular merozoites and prevent invasion of RBCs (Berzins, 2002, Chem. Immunol. 80: 125-143; Galinsky et al., 2005, pp. 113-168, In: I. W. Sherman (ed), Molecular Approaches to Malaria, ASM Press, Washington D.C.; Holder, 1996, pp. 77-104. In: S. L. Hoffman (ed), Malaria vaccine development: a multi-immune response approach, ASM Press, Washington D.C.; Mahanty et al., 2003 J. Exp. Biol. 206: 3781-3788). However, the multiple receptor-ligand interactions and alternate redundant pathways involved in merozoite invasion of RBCs, combined with the polymorphism of vaccine candidate antigens, present a challenge for vaccine design (Berzins, 2002, Chem. Immunol. 80: 125-143; Galinsky et al., 2005, pp. 113-168. In: I. W. Sherman (ed), Molecular Approaches to Malaria, ASM Press, Washington D.C.; Gaur et al, 2004, Int. J. Parasitol. 34: 1413-1429).

*P. falciparum* merozoite surface protein-1 (MSP-1; gp195) emerged during the 1980's as a viable blood-stage vaccine target. MSP-1 is an abundant component of the merozoite surface coat, is conserved across plasmodial species and is essential for parasite growth (Berzins, 2002, Chem. Immunol. 80: 125-143; Galinsky et al., 2005, pp. 113-168. In: I. W. Sherman (ed), Molecular Approaches to Malaria, ASM Press, Washington D.C.; Gaur et al, 2004, Int. J. Parasitol, 34: 1413-1429; Holder, 1996, pp. 77-104. In: S. L. Hoffman (ed), Malaria vaccine development: a multi-immune response approach, ASM Press, Washington D.C.; O'Donnell et al., 2000, Nat. Med. 6: 91-95). During schizont maturation and segmentation, MSP-1 is synthesized as a ~195 kDa precursor protein that is proteolytically processed to form a multi-subunit complex expressed on the surface of merozoites (Holder et al., 1984, J. Exp. Med. 160: 624-62; Lyon et al., 1986, Proc. Natl. Acad. Sci. USA 83: 2989-2993; McBride et al., 1987, Mol. Biochem. Parasitol. 23: 71-84). MSP-1$_{42}$ refers to the 42 kDa, GPI-anchored component in the C-terminal portion of the protein which results from proteolytic processing. Subsequent additional cleavage near the time of invasion yields a 19 kDa, C-terminal domain, called MSP-1$_{19}$, on the merozoite surface (Blackman et al., 1990, J. Exp. Med. 172: 379-382). MSP-1$_{19}$ contains two highly-conserved, epidermal growth factor (EGF)-like domains, which are targets of protective antibodies and which are the major focus of the MSP-1 vaccine development effort (see, for instance, Burns et al., 1989, J. Immunol. 143: 2670-2676; Darko et al., 2005, Infect. Immun. 73: 287-297; Egan et al., 1995, Infect. Immun. 63: 456-466; O'Donnell et al., 2001, J. Exp. Med. 193: 1403-1412). It has been demonstrated that it is the conserved spatial structure of the MSP-1 EGF-like domains, however, and not their primary amino acid sequence, that is essential for parasite growth (O'Donnell et al., 2000, Nat. Med. 6: 91-95).

Vaccines based on the two major alleles of *P. falciparum* MSP-1$_{42}$ (PfMSP-1$_{42}$) are currently in clinical trials (Angov et al. 2003, Mol. Biochem. Parasitol. 128: 195-204; Ockenhouse et al., 2006, Vaccine 24: 3009-3017; Stoute et al., Vaccine, Epub 2005 Dec. 7). MSP-1$_{42}$ consists of the N-terminal component, MSP-1$_{33}$ and the C-terminal component, MSP-1$_{19}$. The MSP-1$_{33}$ processed fragment does not appear to be a primary target of neutralizing antibodies but can provide a source of parasite-specific, T cell epitopes. One problem has been the relatively low immunogenicity of PfMSP-1$_{42}$-based vaccines in non-human primates and in human subjects. To increase immunogenicity, *P. falciparum* MSP-1 (PfMSP-1) subunit vaccines formulated with different adjuvants have been tested in non-human primates. However, no adjuvants tested have enhanced PfMSP-1 immunogenicity to the desired level (Burghaus et al., 1996, Infect. Immun. 64: 3614-3619; Chang et al., 1996, Infect. Immun. 64: 253-261; Darko et al., 2005, Infect. Immun. 73: 287-297; Kumar et al., 1995, Mol. Med. 1: 325-332; Kumar et al., 2000, Infect. Immun. 68: 2215-2223; Stowers et al., 2001, Infect. Immun. 69: 1536-1546). Phase I safety and immunogenicity trials of PfMSP-1$_{42}$ formulated with AS02A (GlaxoSmithKline Biologicals); an oil-in-water emulsion containing both QS21 and 3-deacylated monophosphoryl lipid A, have been completed in malaria-naïve US volunteers and semi-immune Kenyan adults (Ockenhouse et al., 2006, Vaccine 24: 3009-3017; Stoute et al., 2007, Vaccine, 25:176-184, Epub 2005 Dec. 7). The immunogenicity data and the relatively low activity of elicited antibodies in growth inhibition assays suggest that further improvements will be required.

Thus, there is a need in the art for a vaccine with improved immunogenicity and protective efficacy, and in particular, a malaria vaccine. The present invention addresses this need.

BRIEF SUMMARY OF THE INVENTION

The invention provides a composition comprising merozoite surface protein-8 (MSP-8) linked to an antigen. In one embodiment, the antigen is selected from the group consisting of: polypeptide, nucleic acid, polysaccharide, lipid, hapten, inorganic material, and inorganic chemical compound. In another embodiment, the antigen is a polypeptide. In one aspect of this embodiment, the polypeptide antigen is covalently linked to MSP-8. In one aspect of this embodiment, the polypeptide is MSP-1$_{19}$. In one embodiment, MSP-8 and MSP-1$_{19}$ are *P. falciparum* or *P. vivax* sequences or sequences substantially homologous thereto. In one embodiment, the polypeptide is linked to MSP-8 via a linker selected from the group consisting of: a glycine linker, a glycine-rich linker and a glycine-serine linker.

The invention also provides a nucleic acid comprising a sequence encoding a fusion protein comprising merozoite surface protein-8 (MSP-8) linked to a polypeptide antigen. In an embodiment, the nucleic acid consists essentially of a sequence encoding a fusion protein comprising MSP-8 linked to a polypeptide antigen. In another embodiment, a nucleic acid encoding the composition comprising MSP-1$_{19}$ linked to MSP-8 is provided. In an embodiment, MSP-1$_{19}$ is linked to MSP-8 via a spacer peptide. Preferably, the spacer peptide is a five glycine peptide.

Kits comprising a composition of the invention and an instructional material are also provided by the invention.

An isolated antibody that specifically binds to a composition comprising MSP-8 covalently linked to MSP-1$_{19}$ is provided by the invention. In one embodiment, the antibody is selected from the group consisting of a polyclonal antibody, a monoclonal antibody, a humanized antibody, a synthetic antibody, a heavy chain antibody, a biologically active fragment of an antibody, wherein the biologically active fragment comprises an Fv fragment, an Fab fragment or an F(ab)$_2$ fragment, and combinations thereof. In one aspect of this embodiment, the heavy chain antibody is selected from the group consisting of a camelid antibody, a heavy chain disease antibody, and a variable heavy chain immunoglobulin.

Kits comprising an antibody of the invention and an instructional material are provided by the invention.

The invention further provides a vaccine comprising a composition of the invention. In one embodiment, the vaccine is a nucleic acid encoding a composition of the invention.

Additionally, a method of immunizing a human against a *Plasmodium* infection, comprising the step of administering an effective amount of a composition comprising merozoite surface protein-8 (MSP-8) linked to MSP-1$_{19}$ is provided. In one embodiment, MSP-8 and MSP-1$_{19}$ are *P. falciparum* or *P. vivax* sequences or sequences substantially homologous thereto.

The invention further provides a method of inducing an immune response against an antigen in an animal, the method comprising the steps of a) linking the antigen to MSP-8 to form a composition and b) administering an effective amount of the composition to the animal. In one embodiment, the antigen is selected from the group consisting of: polypeptide, nucleic acid, polysaccharide, lipid, hapten, inorganic material, and inorganic chemical compound.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A and 1B are images of SDS-polyacrylamide gels (12%) run under reducing (1A) or non-reducing (1B) conditions and stained with Coomassie Blue. Lane 1: rPyMSP-1$_{42}$ (3 µg). Lane 2: rPyMSP-8 (3 µg). Lane 3: GST-PyMSP-1$_{19}$ (3 µg). Lane 4: GST-PyMSP-8C (3 µg). Lane 5: GST. Molecular mass markers (M) are as indicated on the left side.

In FIG. 2A, blots were probed with mAb302, which recognizes epitopes associated with the EGF-like domains of PyMSP-1, or with normal mouse sera (NMS). In FIG. 2B, blots were probed with polyclonal rabbit sera raised against refolded rPyMSP-8 or normal rabbit sera (NRS): Lane 1: rPyMSP-1$_{42}$ (0.1 µg): Lane 2: GST-PyMSP-1$_{19}$ (0.1 µg). Lane 3: GST (0.1 µg). Molecular weight markers are indicated.

FIG. 3A depicts the % parasitemia in BALB/cByJ mice (n=5) immunized with one of four formulations and challenged with 1×10$^5$ P. yoelii 17XL parasitized erythrocytes two weeks following the third immunization. rPyMSP-1$_{42}$ (●, 10 μg); rPyMSP-8 (■, 10 μg); rPyMSP-1$_{42}$ and rPyMSP-8 (★, 10 μg each); and Quil A alone (◇). The resulting parasitemia was monitored by enumerating parasitized RBCs in thin tail-blood smears stained with Giemsa. "#D" refers to the number of deceased animals at each time point. FIG. 3B depicts the Ag-specific IgG titer in prechallenge immunization sera. Antibody titers were determined by ELISA and are mean±SD. rPyMSP-1$_{42}$ (▨), GST-PyMSP-1$_{19}$ (▩), rPyMSP-8 (■) and GST-PyMSP-8C (□). Immunization groups are indicated along the x-axis. N.D.—none detected.

FIG. 4A depicts schematically the components of the chimeric PyMSP-1/8 vaccine molecule. The left side is the N-terminal and the right side is the C-terminal. The schematic depicts the double EGF-like domains of PyMSP-1$_{19}$ (stippled box) followed by a 5-glycine spacer (filled box) and the full-length PyMSP-8 (open box) with the C-terminal EGF-like domains in PyMSP-8 shown as a hatched box. Approximate positions of cysteine residues are indicated by vertical lines. FIG. 4B consists of images of Coomassie-blue stained SDS-polyacrylamide gel (12%) of purified rPyMSP1/8 (3 μg/lane) under reducing (R) or non-reducing (NR) conditions. FIG. 4C consists of images of the corresponding immunoblot analysis of non-reduced rPyMSP-1/8 probed with: 1) PyMSP-1$_{19}$ specific mAB302; 2) normal mouse sera; 3) rabbit anti-rPyMSP-8 sera; and 4) normal rabbit sera. Molecular weight markers are indicated.

FIG. 6A depicts the percent survival as a function of days post-infection. FIG. 6B depicts the mean % parasitemia as a function of days post-infection. "#D" refers to the number of deceased animals at each time point.

FIG. 7A depicts the percent survival as a function of days post-infection. FIG. 7B depicts the mean % parasitemia as a function of days post-infection.

FIG. 8A depicts data from BALB/cByJ mice immunized with rPyMSP1/8 (▼, 14 μg) formulated with Quil A as adjuvant or with Quil A alone (◇). Two weeks following the third immunization, mice were challenged with 1×10$^5$ P. yoelii 17XL parasitized erythrocytes and parasitemia monitored (primary challenge; left panel). Following parasite clearance, rPyMSP-1/8 immunized mice were rested and rechallenged (day 106) with 1×10$^5$ P. yoelii 17XL parasitized erythrocytes and parasitemia again monitored (secondary challenge; right panel). FIG. 8B depicts data from BALB/cByJ mice were immunized with rPyMSP1/8 (∇, 14 μg) formulated with Quil A as adjuvant or with Quil A alone (◇). Approximately 4 months (17 weeks) following the third immunization, mice were challenged with 1×10$^5$ P. yoelii 17XL parasitized erythrocytes and parasitemia monitored. The control group in FIG. 8A (secondary challenge) and in FIG. 8B are the same set of Quil A immunized mice.

FIGS. 9A and 9B are a series of graphs depicting data relating to conformational epitopes of rPyMSP vaccine antigens. Specific antibodies were removed from rPyMSP-1/8 specific immune sera by immuno-affinity chromatography. Serial dilutions of unabsorbed (solid lines and solid symbols) and absorbed (broken lines and hollow symbols) sera were analyzed by ELISA on wells coated with rPyMSP-1/8 (●, ○) rPyMSP-8 (▲, △), rPyMSP-1$_{42}$ (♦, ◇) or GST-PyMSP-1$_{19}$ (■, □). FIG. 9A depicts data obtained using rPyMSP-8 and GST-rPyMSP-1$_{19}$ specific antibodies. FIG. 9B depicts data obtained using rPyMSP-8 and rPyMSP-1$_{42}$ specific antibodies.

DETAILED DESCRIPTION OF THE INVENTION

Figure 2A:
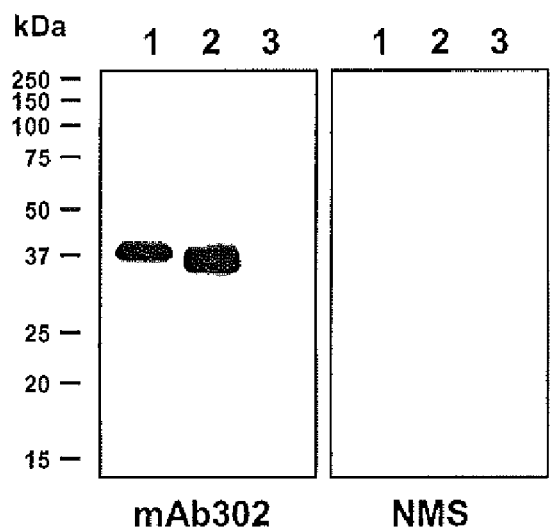
FIGS. 2A and 2B are images of immunoblots of 12% SDS-polyacrylamide gels.

The present invention relates to a composition of matter comprising merozoite surface protein-8 (MSP-8) linked to an antigen. Preferentially, the antigen is from a pathogen of an animal, including antigens from malaria parasites including, but not limited to, P. yoelli, P. falciparum and P. vivax. Advantageously, the composition of matter enhances the immune response of a host to the antigen. As shown herein, a composition comprising MSP-8 linked to an antigen enhances the immunogenicity of the antigen in a mammal immunized with the composition. MSP-8 fused to an antigen better enables antibody-mediated immunity as compared to the antigen alone. As shown herein, immunization using a molecule comprising P. yoelli MSP-8 (PyMSP-8) covalently linked via amide bonds to P. yoelli MSP-1$_{19}$ (PyMSP-1$_{19}$) induced an immune response sufficient to protect the immunized organism against lethal P. yoelli challenge, provide quick suppression after a challenge infection and minimize parasitemia, in contrast to immunization with PyMSP-1$_{19}$ alone. Without wishing to be bound by theory, it is believed that a composition comprising MSP-8 linked to an antigen facilitates the induction of an immune response against the antigen when delivered to the bloodstream of the animal because MSP-8 induces CD4$^+$ T cell responses that promote production of antibodies to the linked antigen, When the antigen comprises an immunogenic epitope of a pathogen, the immune response provoked by administration of the composition can thereafter inhibit or prevent pathology caused by the pathogen in the animal. In a preferred embodiment, the antigen is MSP-1$_{19}$, preferably P. falciparum or P. vivax MSP-1$_{19}$.

Thus, the invention provides a composition comprising MSP-8 linked to an antigen, which is useful, for instance, as a vaccine, and a method of using the composition to induce an immune response against the antigen in a vertebrate. In a preferred embodiment of the composition, MSP-8 is covalently linked to the antigen.

The invention also provides an isolated nucleic acid encoding a fusion protein comprising MSP-8 covalently linked to a polypeptide antigen. The invention further provides an antibody that specifically binds to a composition comprising MSP-8 covalently linked via amide bonds to MSP-$1_{19}$. Kits are also provided.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in immunology, cell culture, molecular genetics, organic chemistry, and nucleic acid chemistry and hybridization are those well known and commonly employed in the art.

The techniques and procedures for recombinant manipulations, including nucleic acid and peptide synthesis, are generally performed according to conventional methods in the art and various general references (e.g., Sambrook et al, 2001, Molecular Cloning, A Laboratory Approach, Cold Spring Harbor Laboratory Press, Cold Spring Harbor, N.Y.; Ausubel et al., eds, 2005, Current Protocols in Molecular Biology, John Wiley & Sons, New York, N.Y.; and Gerhardt et al., eds., 1994, Methods for General and Molecular Bacteriology, American Society for Microbiology, Washington, D.C.), which are provided throughout this document.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent on the context in which it is used.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426). As used herein, a "neutralizing antibody" is an immunoglobulin molecule that binds to and blocks the biological activity of the antigen.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

"Antigen" as used herein refers to any substance capable of eliciting an immune response, but specifically excludes peptide sequences consisting essentially of 6His, glutathione-S-transferase (GST) or MGSSHHHHHHSSGLVPRGSHM (SEQ ID NO: 13; the 21 amino acid sequence from the pET vector that includes 6His). Thus, a fusion protein consisting of SEQ ID NO: 13 fused to MSP-8 is excluded from the invention. Non-limiting examples of an antigen include polypeptides, bacteria, viruses, nucleic acid, polysaccharides, such as carbohydrates, lipids, small molecule haptens and the like.

"Effective amount" as used herein with regard to an antigen refers to a nontoxic amount of an antigen suitable to stimulate a cellular and/or humoral immune response to the antigen.

As used herein "endogenous" refers to any material produced within or originating inside an organism.

"Exogenous" refers to any material introduced into or produced outside an organism.

As used herein, "expression cassette" refers to a nucleic acid molecule comprising a coding sequence operably linked to promoter/regulatory sequences necessary for transcription and translation of the coding sequence. An expression cassette encoding a desired nucleic acid sequence does not include translation sequences.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC5' share 50% homology.

As used herein, "homology" is used synonymously with "identity."

"Linked" refers to noncovalent or covalent bonding between two or more molecules. Linking may be direct or indirect. Two molecules are indirectly linked when the two molecules are linked via an intervening molecule. For instance, molecules linked using a crosslinking reagent are indirectly linked to each other. Similarly, two biotinylated molecules bound to a common avidin moiety are indirectly linked. Two molecules are directly linked when there is no intervening molecule linking them.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is naturally occurring.

"Pharmaceutically acceptable carrier" refers herein to a composition suitable for delivering the inventive composition to a subject without excessive toxicity or other complications while maintaining the biological activity of the molecule. Protein-stabilizing excipients, such as mannitol, sucrose, polysorbate-80 and phosphate buffers, are typically found in such carriers, although the carriers should not be construed as being limited only to these compounds.

As used herein, the term "physiologically acceptable" ester or salt means an ester or salt form of an active ingredient in a pharmaceutical composition which is compatible with any other ingredients of the pharmaceutical composition and which is not deleterious to the subject to which the composition is to be administered.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

"Polypeptide" refers to a polymer composed of amino acid residues, related naturally-occurring, structural variants, and synthetic, non-naturally-occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Specifically bind" as used herein refers to the higher affinity of a binding molecule for a target molecule compared to the binding molecule's affinity for non-target molecules. A binding molecule that specifically binds a target molecule does not substantially recognize or bind non-target molecules.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive promoter" is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

A host cell that comprises a recombinant polynucleotide is referred to as a "recombinant host cell." A gene which is expressed in a recombinant host cell wherein the gene comprises a recombinant polynucleotide, produces a "recombinant polypeptide."

"Recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Treating" as used herein means ameliorating the effects of, or delaying, halting or reversing the progress of a condition. The word encompasses reducing the severity of a symptom of a condition and/or the frequency of a symptom of a medical condition.

By the term "applicator," as the term is used herein, is meant any device including, but not limited to, a hypodermic syringe, a pipette, and the like, for administering the compounds and compositions of the invention.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, an "oily" liquid is one which comprises a carbon-containing liquid molecule and which exhibits a less polar character than water.

By the term "vaccine," as used herein, is meant a composition comprising an antigen which, when inoculated into a mammal, has the effect of stimulating a cellular immune response comprising a T-cell response or a humoral immune response comprising a B-cell response generally resulting in antibody production. The T cell response may be a cytotoxic T-cell response directed against an organism that expresses the antigen. However, the induction of a T-cell response comprising other types of T cells by the vaccine of the invention is also contemplated. A B-cell response results in the production of antibody that binds to the antigen. The vaccine may serve to elicit an immune response in the mammal which serves to protect the mammal against a disease.

By the term "immunizing a human against an antigen" is meant administering to the human a composition, a protein complex, a DNA encoding a protein complex, an antibody or a DNA encoding an antibody, which elicits an immune response in the human, which immune response provides protection to the human against a disease caused by the antigen or an organism which expresses the antigen.

It is understood that any and all whole or partial integers between any ranges set forth therein are included herein.

Description

The present invention relates to a composition comprising merozoite surface protein-8 (MSP-8) linked to an antigen and methods of using the composition to induce an immune response against the antigen. In preferred embodiments, the presence of MSP-8 in the composition enhances the immunogenicity of the linked antigen.

MSP-8

MSP-8 is a surface protein found in *Plasmodium* merozoites and trophozoites, including *P. yoelli*, *P. falciparum* and *P. vivax*. Naturally-occurring MSP-8 protein is expressed with an N-terminal signal sequence and a C-terminal hydrophobic membrane-anchor sequence. MSP-8 contains two, cysteine-rich EGF-like domains in its C-terminal. Any naturally-occurring MSP-8 sequence may be used in the composition of the invention. Preferably, the sequence is the mature, full-length MSP-8 sequence and therefore does not include the N-terminal signal sequence (N-terminal-most sequence of about 22 amino acids) or the C-terminal hydrophobic membrane-anchor sequence (C-terminal-most sequence of about 21 amino acids). Preferably, the MSP-8 component of the composition of the invention comprises its naturally-occurring disulfide bonds.

Numerous MSP-8 genes are known in the art. The nucleotide sequence and amino acid sequence of an exemplary *P. yoelli* isolate 17XL MSP-8 are available as GenBank® Accession Nos. AY005132 (SEQ ID NO. 1) and AAG02279 (SEQ ID No. 2), respectively, each of which are incorporated herein by reference in their entirety. The nucleotide sequence and amino acid sequence of exemplary *P. falciparum* isolate NF7 MSP-8 are available as GenBank® Accession Nos. AF325156 (SEQ ID NO. 3) and AAK63225 (SEQ ID No. 4), respectively, each of which are incorporated herein by reference in their entirety. MSP-8 genes have been cloned from other isolates of *P. falciparum* (D10, K1, AA01, ItG2 and FVO) and include nucleotide sequences having GenBank® Accession Nos. AF325157, AF325158, AF325159, AF325160 and AF325161, respectively, and the corresponding amino acid sequences AAK63226, AAK63227, AAK63228, AAK63229 and AAK63230, all of which are incorporated herein in their entirety. The nucleotide sequence and amino acid sequence of an exemplary *P. vivax* MSP-8 are available as GenBank® Accession NO. AY743238 (SEQ ID NO. 5) and AAW59434 (SEQ ID NO. 6), each of which are incorporated herein by reference in their entirety. MSP-8 homologs are also present in the genome sequences of *P. knowlesi*, *P. berghei* and *P. chabaudi* (see http://www.(dot)PlasmoDB(dot)org; Bahl et al., 2003, Nucleic Acids Res. 31(1): 212-215). MSP-8 is highly conserved throughout its protein sequence (Black et al., 2001, Mol. Biochem. Parasitol. 114:217-226; Perez-Leal et al., 2004, Biochem. Biophys. Res. Commun. 324:1393-1399).

MSP-8 from *P. falciparum* comprises an about 170 amino acid N-terminal domain, characterized by tracts of asparagine and aspartic acid (see, for instance, amino acids about 51 to about 225 of SEQ ID NO. 4), which is not present in MSP-8 of *P. yoelli*, *P. vivax*, *P. knowlesi* and *P. berghei*. In one embodiment of the invention, the molecule of the invention comprises about residue 24 to about residue 583 of SEQ ID NO. 4, thereby including the Asn/Asp domain. In another embodiment, the molecule of the invention comprises about residue 225 to about residue 583 of SEQ ID NO. 4.

Substantially homologous sequences to MSP-8 may also be used in the composition of the invention. Substantially homologous sequences to MSP-8 sequences are those which exhibit at least about 85% homology, usually at least about 90%, and preferably at least about 95% homology with a reference MSP-8 sequence. In one embodiment, the reference MSP-8 sequence is SEQ ID NO.2. In another embodiment, the reference MSP-8 sequence is SEQ ID NO.4. In another embodiment, the reference MSP-8 sequence is SEQ ID NO.6.

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sol. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example, at the National Center for Biotechnology Information (NCBI) world wide web site having the universal resource locator "http://www(dot)ncbi(dot)nlm(dot)nlm(dot)nih(dot)gov/BLAST/." BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See http://www.(dot)ncbi(dot)nlm(dot)nih(dot)gov.

The percent identity between two sequences can be determined using techniques similar to those described above, with or without allowing gaps. In calculating percent identity, typically exact matches are counted.

Naturally-occurring homologs of these sequences are also useful in the invention. Similarly, neutral sequence variants of these sequences, based on the degeneracy of the genetic code, are also useful. Variants comprising conservative amino acid changes may be made, which although they alter the primary sequence of the protein or peptide, do not normally alter its tertiary structure or function. Conservative amino acid substitutions typically include substitutions within the following groups: glycine and alanine; valine, isoleucine, and leucine; aspartic acid and glutamic acid; asparagines and glutamine; serine and threonine; lysine and arginine; phenylalanine and tyrosine.

Antigens

Suitable antigens that can be linked to MSP-8 to prepare a composition of the invention include polypeptides, nucleic acids, polysaccharides, such as carbohydrates, lipids (such as membrane lipids, e.g., phospholipids), particles of organic or inorganic materials (for example, ceramic particles), small organic or inorganic chemical compounds (tetrafluroethylene polymers, chitosans). In preferred embodiments, the antigen is a polypeptide.

The antigen may be from a pathogen. Non-limiting examples of pathogens include, but are not limited to, *Plasmodium, Leishmania, Toxoplasma, Mycobacterium* and *Clostridium*. In a preferred embodiment, the pathogen is *Plasmodium*. In one embodiment, the antigen is a polypeptide that comprises an immunogenic epitope selected from MSP-1, MSP-3, AMA-1 or CSP. The nucleotide sequence and amino acid sequence of an exemplary *P. yoelli* MSP-1 are available as GenBank® Accession Nos. J04668 (SEQ ID NO. 7) and AAA29702 (SEQ ID NO. 8), respectively, incorporated herein by reference in their entirety. The nucleotide sequence and amino acid sequence of an exemplary *P. falciparum* MSP-1 are available as GenBank® Accession Nos. X03371 (SEQ ID NO. 9) and CAA27070 (SEQ ID NO. 10), respectively, incorporated herein by reference in their entirety. The nucleotide sequence and amino acid sequence of an exemplary *P. vivax* MSP-1 are available as GenBank® Accession Nos. AF435593 (SEQ ID NO. 11) and AAN86207 (SEQ ID NO. 12), respectively, incorporated herein by reference in their entirety. Sequences for other *Plasmodium* antigens in the art, or readily determined by the skilled artisan using conventional methods in the art.

In a preferred embodiment, the antigen is MSP-$1_{19}$. Any naturally-occurring MSP-$1_{19}$ domain may be used as an antigen in the molecule of the invention. In one embodiment, the MSP-$1_{19}$ domain comprises about amino acids 1517 to 1612 of SEQ ID NO. 10. In one embodiment, the composition comprises about amino acids 1517 to 1612 of SEQ ID NO: 10, or a substantially homologous sequence, linked to about amino acids 24-583 of SEQ ID NO: 4, or a substantially homologous sequence. In another embodiment, the composition comprises about amino acids 1517 to 1612 of SEQ ID NO: 10, or a substantially homologous sequence, linked to about amino acids 225-583 of SEQ ID NO: 4, or a substantially homologous sequence. In these embodiments, the composition is preferably a fusion protein. The fusion protein optionally includes spacer intervening between the antigen and MSP-8 sequences.

Substantially homologous sequences to MSP-$1_{19}$ may also be used in the composition of the invention. Substantially homologous sequences to MSP-$1_{19}$ sequences are those which exhibit at least about 85% homology, usually at least about 90%, and preferably at least about 95% homology with a reference MSP-$1_{19}$ protein. In one embodiment, the reference MSP-$1_{19}$ sequence is amino acids 1619 to 1756 of SEQ ID NO. 8. In another embodiment, the reference MSP-$1_{19}$ sequence is amino acids 1517 to 1612 of SEQ ID NO. 10. Naturally-occurring homologs of these sequences are also useful in the invention. Similarly, neutral sequence variants of these sequences, based on the degeneracy of the genetic code, are also useful, as are variants with conservative amino acid substitutions.

In another embodiment, the antigen in a molecule of the invention is a tumor-associated antigen. Various tumor-associated antigens have been identified. Further, much research effort is being expended to identify additional tumor associated antigens. Some groups of tumor-associated antigens, also referred to in the art as tumor-specific antigens, are tissue specific. Examples include, but are not limited to, tyrosinase for melanoma, PSA and PSMA for prostate cancer and chromosomal cross-overs such as bcr/abl in lymphoma. However, many tumor-associated antigens identified occur in multiple tumor types, and some, such as oncogenic proteins which actually cause the transformation event, occur in nearly all tumor types. For example, normal cellular proteins that control cell growth and differentiation, such as p53 and HER-2/neu, can accumulate mutations resulting in upregulation of expression of these gene products, thereby making them oncogenic (McCartey et al., 1998, Cancer Research 15:58 2601-5; Disis et al., 1994, Ciba Found. Symp. 187:198-211). These mutant proteins can be the target of a tumor-specific immune response in multiple types of cancer. Transforming proteins from oncogenic viruses such as E6 and E7 from HPV or EBNA1 from Epstein Barr virus (EBV) also occur in many tumor types and can be the target of a tumor specific immune response in multiple types of cancer (McKaig et al., 1998, Head Neck 20(3):250-65; Punwaney et al., 1999, Head Neck 21(1):21-9; Serth et al., 1999, Cancer Res. 15:59(4):823-5; Pagano, 1999, Proc. Assoc. Am. Physicians 111(6):573-80). Non-oncogenic host proteins such as MAGE and MUC family are also ubiquitous. Specifically, the MAGE family of antigens have been found in many different cancers including breast cancer, lung cancer, esophageal cancer, hepatic cancer, thyroid cancer, neuroblastoma, gastric cancer, multiple myeloma and melanoma (Gillespie et al., 1999, Cancer Treat. Rev. 25(4):219-27). The MUC family of antigens has been associated with ovarian and endometrial cancer, breast cancer, multiple myeloma, pancreatic cancer, and colon and rectal cancer (Segal-Eiras et al., 1997, Allergol. Immunopathol. 25(4):176-81). As will be obvious to those of skill in the art upon this disclosure, the invention is also applicable to other tumor associated antigens not specifically listed herein.

Polypeptides and nucleic acids useful in the composition of the invention may be obtained by standard methods known to the skilled artisan. Methods include in vitro peptide synthesis, in vitro oligonucleotide synthesis and biological means. Biological means includes purification from a biological source, in vitro transcription and/or translation synthesis and recombinant synthesis using a recombinant host cell. DNA and amino acid sequences are available for many nucleic acid and polypeptide antigens useful in the molecule of the invention and are readily obtained by the skilled artisan from publicly-available databases, such as GenBank® (United States Department of Health and Human Services, Bethesda Md.).

Merrifield-type solid phase peptide synthesis may be routinely performed to yield peptides up to about 60-70 residues in length, and may, in some cases, be utilized to make peptides up to about 100 amino acids long. Larger peptides may also be generated synthetically via fragment condensation or native chemical ligation (Dawson et al., 2000, Ann. Rev. Biochem. 69:923-60). A great advantage to the utilization of a synthetic peptide route is the ability to produce large amounts of peptides, even those that rarely occur naturally, with relatively high purities, i.e., purities sufficient for research, diagnostic or therapeutic purposes.

Examples of solid phase peptide synthesis methods include the BOC method, which utilizes tert-butyloxcarbonyl as the α-amino protecting group, and the FMOC method, which utilizes 9-fluorenylmethyloxcarbonyl to protect the α-amino of the amino acid residues, both which methods are well-known by those of skill in the art.

Incorporation of N- and/or C-blocking groups may also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin, so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function, e.g. with DCC, can then proceed by addition of the desired alcohol, followed by de-protection and isolation of the esterified peptide product.

Incorporation of N-terminal blocking groups may be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product may then be cleaved from the resin, de-protected and subsequently isolated.

Biological preparation of MSP-8 or an antigen may include purification from a cell, tissue or organism that comprises the desired component. For instance, a naturally-occurring source of MSP-8 is merozoites obtained from erythrocytes infected with, for instance, *P. falciparum*. The preferred stage for isolating MSP-8 is the trophozoite stage. Preferably the MSP-8 is the full-length, mature polypeptide. Biological preparation also includes expression of a gene or coding sequence for the nucleic acid and/or protein components in a recombinant host cell, an in vitro transcription, or an in vitro translation system. DNA sequences for MSP-8 and MSP-1 from numerous isolates of several *Plasmodium* species are known in the art, and exemplary sequences for both are provided elsewhere herein.

Vectors for expression cassettes and methods for the introduction of exogenous DNA into cells with concomitant expression of the exogenous DNA in the cells are described, for example, in Sambrook et al., supra, 2001; Ausubel et al., supra, 2005. Techniques for introducing vectors into target cells include, but are not limited to, electroporation, photoporation, calcium precipitation, fusion, transfection, lipofection, viral targeting and the like.

Any expression vector compatible with the expression of a polypeptide in a host cell is suitable for use in the instant invention, and can be selected from the group consisting of a plasmid DNA, a viral vector, and a mammalian vector. Vectors may be episomal, or may be provided for integration into the target cell genome via homologous recombination or random integration. Viral vectors useful in the methods of the invention include, but are not limited to, cytomegalovirus vectors, adenovirus vectors and retrovirus vectors, such as MigRI, MMLC, HIV-2 and ALV.

The vector comprising the expression cassette, or a vector that is co-introduced with the expression vector, can comprise a marker gene. Marker genes are useful, for instance, to monitor transfection efficiencies. Marker genes include genes for selectable markers, including, but not limited to, G418, hygromycin, and methotrexate, and genes for detectable markers, including, but not limited to, luciferase and GFP.

The coding sequence contained in an expression cassette may, optionally, be fused in-frame to other coding sequences. For instance, the coding sequence of an detectable tag or purification tag may be included. Such tags are useful, for instance, to assist in the rapid purification of the encoded polypeptide or variant thereof. An example of such a tag is a 6-His sequence. The fusion may be at either the N-terminal or the C-terminal of a polypeptide, provided the immunogenicity of the molecule is maintained. Such tags may be removed from the purified fusion polypeptide by engineering an intervening cleavage site between the tag and the other coding sequence. Thrombin is a useful cleavage agent for this purpose. Commercial products, such as TAGZyme (Qiagen® Inc., Valencia, Calif.), are available as well.

In the context of an expression vector, the vector may be readily introduced into a suitable host cell, e.g., mammalian, bacterial, yeast or insect cell, by any method in the art. For example, the expression vector can be transferred into a host cell by physical, chemical or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., supra, 2001 and Ausubel et al., supra, 2005.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, e.g., U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems are well known in the art.

To ensure that the polypeptide obtained from either chemical or biological synthetic techniques is the desired polypeptide, analysis of the polypeptide composition may be conducted. Such amino acid composition analysis may be conducted using high resolution mass spectrometry to determine the molecular weight of the peptide. Alternatively, or additionally, the amino acid content of the peptide may be confirmed by hydrolyzing the peptide in aqueous acid, and separating, identifying and quantifying the components of the mixture using HPLC or an amino acid analyzer. Protein sequenators, which sequentially degrade the peptide and identify the amino acids in order, may also be used to definitively determine the sequence of the peptide. One of skill in the art is familiar with conventional methods for analyzing a nucleic acid antigen and other types of antigens.

Prior to use in the compositions and methods of the invention, polypeptides or other molecules are optionally purified to remove contaminants. Any one of a number of a conventional purification procedures may be used to attain the required level of purity including, for example, reversed-phase high-pressure liquid chromatography (HPLC) using an alkylated silica column, such as $C_4$-, $C_8$- or $C_{18}$-silica, or variations thereof. A gradient mobile phase of increasing organic content is generally used to achieve purification, for example, acetonitrile in an aqueous buffer, usually containing a small amount of trifluoroacetic acid. Ion-exchange chromatography may be also used to separate polypeptides based on their charge. Gel filtration chromatography may be used to separate polypeptides, nucleic acids and other types of antigens based on their size.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutseher et al. (ed., 1990, *Guide to Protein Purification*, Harcourt Brace Jovanovich, San Diego).

Polypeptides and nucleic acids used in the composition of the invention may be modified using ordinary molecular biological techniques to improve their resistance to proteolytic degradation or to optimize solubility properties or to render them more suitable as a vaccine or immunogen. Analogs of such polypeptides include those containing residues other than naturally occurring L-amino acids, e.g., D-amino acids or non-naturally occurring synthetic amino acids. The polypeptides useful in the invention may further be conjugated to non-amino acid moieties that are useful in their applications. In particular, moieties that improve the stability, biological half-life, water solubility, and immunologic characteristics of the peptide are useful.

Antigens which are not nucleic acids or polypeptides may also be obtained by conventional methods known in the art. Such antigens may be purified from a naturally-occurring source or synthesized biologically (e.g, enzymatic production in vitro or using recombinantly-engineered organisms) or chemically (e.g., organic synthesis). Purification methods include, but are not limited to, ultrafiltration, nanofiltration, reverse osmosis, high pressure liquid chromatography, and the like. For instance, carbohydrates may be prepared by enzymatic synthesis. Alternatively, they may be prepared by degradation of naturally-occurring oligosaccharides. Methods used in analytical chemistry and organic syntheses are well known and commonly employed in the art. Standard techniques or modifications thereof, may be used for chemical syntheses and chemical analyses.

Preparing a Composition of the Invention

To prepare a composition of the invention, an antigen is linked to MSP-8. The precise chemistry or method used to link the antigen and MSP-8 is not critical, provided the resulting composition retains immunogenicity. The linkage must merely be sufficiently strong or resilient such that MSP-8 does not dissociate from the antigen upon administration to the bloodsytem of an animal to be immunized. The antigen and MSP-8 may be linked by a covalent bond, such as, for example, a peptide bond. However, strong non-covalent linkage can also be used. The MSP-8 and the antigen can be made separately and thereafter linked, or they can be made essentially simultaneously, for instance, by expression of a recombinant polynucleotide encoding a fusion protein comprising an antigen and MSP-8.

The MSP-8 and antigen moieties of the composition may be linked directly together, may be linked indirectly together, or combinations thereof. Linkage may be covalent bonding or non-covalent bonding. For example, in an embodiment, MSP-8 and an antigen are linked directly together by covalent bonds. In one aspect, the antigen is a polypeptide and the covalent bonds are amide bonds. In another embodiment, the components are indirectly linked together by linking the individual components to a common molecule, such as a spacer or linker.

The nature of the spacer or linker may vary. In some embodiments, the spacer is a peptide spacer. Peptide linkers useful in the molecule of the invention include, but are not limited to, glycine linkers, glycine-rich linkers, serine-glycine linkers, and the like. A glycine-rich linker comprises at least about 50% glycine and preferably at least about 60% glycine. Linkers may be naturally-occurring sequences or designed sequences. See U.S. Pat. No. 6,541,219 for examples of peptide linkers. The skilled artisan is familiar with the design and selection of peptide linkers. See, for instance, Robinson et al., 1998, Proc. Natl. Acad. Sci. USA 95:5929-5934. Automated programs are also available for peptide linker design (e.g., Crasto et al., 2000, Protein Engineering 13:309-312).

An antigen can be linked to either the N-terminal or the C-terminal of MSP-8. In one embodiment, an antigen is linked to the N-terminal of MSP-8. In one embodiment, the linkage is covalent. In another embodiment, linkage is via an intervening molecule. Examples of intervening molecules that can be used as linkers include biotin, avidin, and the like. Linkers of this type may be interposed between the antigen and MSP-8 moieties. For instance, one moiety may be biotinylated and the other moiety may be covalently attached to a streptavidin moiety. In one embodiment, each moiety is biotinylated to enable binding to a common avidin molecule.

In some embodiments, a single antigen is linked to MSP-8. In other embodiments, two or more antigens are linked to single MSP-8 moiety to prepare a composition of the invention.

Covalent attachments useful in the composition include, but are not limited to, standard protein cross-linking chemistries, such as glutaraldehyde activation of amine-functionalized surfaces, trialkoxy aldehyde silanes, DMP (dimethyl pimelimidate), and N-hydroxysuccinimide active ester. Non-limiting examples of non-covalent attachments useful in preparing the composition of the invention include hydrophobic interactions and avidin/biotin systems. Avidin/biotin systems are preferred.

Biotinylation is the process of attaching biotin, or a biotin derivative, to another molecule, for instance an antibody, yielding a biotinylated molecule. Biotinylation as used herein encompasses both chemical conjugation of biotin to a molecule, directly or via a linker molecule, recombinant biotinylation, as well as indirect biotinylation. A moiety may be indirectly labeled by binding it with a biotinylated reagent, provided the biotinylated reagent does not adversely affect the immunogenicity of the molecule of the invention.

Biotinylated linkers are well known in the art and are commercially available. The biotin can be separated by any length linker from the moiety attachment site. Linkers are advantageous in reducing potential interactions between the biotin and the molecule to which it is conjugated, and also enhances biotin binding to the biotin binding sites of avidin, which are relatively deep.

Compounds useful in conjugating a molecule with biotin include, but are not limited to, aliphatic amines, carboxylic acid, DNP-X-biocytin-X, FMOC, hydrazide, iodoacetamide, maleimide, nitriloacetic acid and succinimidyl ester. Biotin, including various spacers, linking groups and the like, and methods of biotinylation are well known to the skilled artisan. See, for example, Savage et al., 1992, Avidin-Biotin Chemistry: A Handbook, Pierce Chemical Company, Rockford, Ill.; Diamandis et al., 1991, Clin. Chem. 37:625-636; DE 3629194; U.S. Pat. Nos. 4,709,037, 4,794,082, 4,798,795, 5,180,828, and 5,252,743; and WO 85/05638, each of which is incorporated herein by reference in its entirety.

In vivo biotinylation can be accomplished by recombinant methods known in the art. In brief, a nucleic acid encoding a polypeptide to be biotinylated is operably linked to a sequence encoding a biotinylation signal, such as Avitag (Beckett et al., 1999, Prot. Sci. 8:921-929) or Biotab (de Boer et al., 2003, PNAS 100:7480-7485). The recombinant nucleic acid is then expressed in a host cell which expresses a biotin ligase (e.g., *E. coli* Bir A), either endogenously or recombinantly and is cultured in a biotin-containing medium. U.S. Pat. Publication No. 20040033603, hereby incorporated by reference in its entirety, discloses bicistronic vectors useful in such in vivo biotinylation applications. Alternatively, the recombinant nucleic acid encoding a polypeptide sequence fused to a biotinylation signal is expressed in a host cell in the absence of biotin. The fusion protein is purified and is biotinylated in vitro using isolated biotin ligase. Products for in vivo biotinylation systems are commercially available, for instance, from GeneCopeia and Avidity.

When the antigen of the composition of the invention is a polypeptide, peptide coupling chemistry may be employed to link the antigen to MSP-8 together directly or indirectly by means of a linking agent. The standard peptide coupling chemistry methods and procedures useful in this invention are readily available. Examples of books using these methods include, but are not limited to, the following citations incorporated herein by reference: P. D. Bailey, An Introduction to Peptide Chemistry, Ed.: John Wiley & Sons, 1990; Miklos Bodansky, Peptide Chemistry, A Practical Textbook, Ed.: Springer-Verlag, 1988; Miklos Bodansky, Principles of Peptide Synthesis, "Reactivity and Structure Concepts in Organic Chemistry," Volume 16, Ed.: Springer-Verlag, 1984; and Miklos Bodansky, Principles of Peptide Synthesis, "Reactivity and Structure Concepts in Organic Chemistry," Volume 21, Ed.: Springer-Verlag, 1984. See also U.S. Pat. Nos. 4,340,535 and 5,776,427 and EP 44167, each of which is incorporated herein by reference in its entirety.

Cross-linking reagents are used to form molecular bridges that tie together functional groups of two different proteins (e.g., MSP-8 and MSP-$1_{19}$) or a non-protein moiety and protein moiety. To link two different proteins in a step-wise manner, heterobifunctional cross-linkers can be used, which eliminate the unwanted homopolymer formation. An exemplary heterobifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker can react with the lysine residue(s) of one protein (e.g., MSP-8) and through the thiol reactive group, the cross-linker, already tied up to the first protein, reacts with the cysteine residue (free sulfhydryl group) of the other protein (e.g., MSP-$1_{19}$). Useful heterobifunctional crosslinking agents include 4-succinimidyloxycarbonyl-methyl-(2-pyridyldithio)-toluene (SMPT) or N-succinimidyl-3-(2-pyridyidithio)propionate (SPDP), both of which can be obtained from Pierce, Rockland, Ill.

SMPT is a bifunctional cross-linker containing a disulfide bond that is "sterically hindered" by an adjacent benzene ring and methyl groups. It is believed that steric hindrance of the disulfide bond serves a function of protecting the bond from attack by thiolate anions, such as glutathione, which can be present in tissues and blood, and thereby help in preventing decoupling of linked moieties. The SMPT cross-linking reagent, as with many other known cross-linking reagents, lends the ability to cross-link functional groups such as the SH of cysteine or primary amines (e.g., the epsilon amino group of lysine). Another possible type of cross-linker includes the heterobifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

While numerous types of disulfide-bond containing linkers are known that can successfully be employed to conjugate a moiety to a substrate, certain linkers may generally be preferred over other linkers, based on differing pharmacologic characteristics and capabilities. For example, linkers that contain a disulfide bond that is sterically "hindered" may be preferred, due to their greater stability in vivo. However, non-hindered linkages, such as SATA and 2-iminothiolane, may also be used. Other crosslinkers, including trifunctional crosslinkers, such as tris-succinimidyl aminotriacetate (TSAT), may be used in preparing a composition of the invention.

The spacer arm between the reactive groups of any cross-linkers can have various length and chemical composition. A longer spacer arm allows a better flexibility of the molecule's components, while some particular features in the bridge (e.g., benzene group) can lend extra stability to the reactive group or an increased resistance of the chemical link to the action of various aspects (e.g., disulfide bond resistant to reducing agents).

In addition to chemical conjugation of two components, polypeptide moieties may also be directly linked together as a fusion protein, provided the MSP-8 and the antigen moieties retain their structural integrity in the context of the fusion protein. The invention thus encompasses a nucleic acid encoding a composition of the invention wherein the composition is a fusion protein comprising MSP-8 and an antigen. The MSP-8 and antigen moieties may be separated within the fusion protein by a spacer or linker peptide to enable proper folding of the moieties and to reduce potential steric problems. In one embodiment, the spacer peptide is a five (5) glycine peptide. Other linker sequences are described elsewhere herein. Using standard molecular biology techniques, a nucleic acid encoding a polypeptide comprising, for instance, MSP-$1_{19}$ and MSP-8, may be used to produce a fusion protein. The nucleic acid molecules are inserted into a vector that is able to express the encoded fusion protein when introduced into an appropriate host cell. The nucleic acid molecules are operably linked to promoter/regulatory sequences. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the invention under control of transcriptional/translational control signals. These methods may include in vitro recombinant DNA and synthetic techniques and in vivo recombinations. Promoters which may be used to control expression of the fusion polypeptide molecules include, but are not limited to, the long terminal repeat, the SV40 early promoter region, the CMV promoter, the M-MuLV 5' terminal repeat the promoter contained in the 3' long terminal repeat of Rous sarcoma virus, the herpes thymidine kinase promoter, the regulatory sequences of the metallothionine gene; prokaryotic expression sequences, such as the β-lactamase promoter or the tac promoter; promoter elements from yeast or fungi, such as the Gal 4 promoter, the ADH (alcohol dehydrogenase) promoter, PGK (phosphoglycerol kinase) promoter, alkaline phosphatase promoter, and tissue-specific transcriptional control regions obtained from, for example, an elastase I gene, insulin gene, immunoglobulin gene, mouse mammary tumor virus, albumin gene, α-fetoprotein gene, α1-antitrypsin gene, β-globin gene, myelin basic protein gene, myosin light chain-2 gene, and gonadotropic releasing hormone gene.

A nucleic acid encoding a molecule of the invention may also be expressed in vitro using in vitro transcription/translation systems. In vitro translation systems are known in the art and include extracts from rabbit reticulocytes, wheat germ and *Escherichia coli*. Commercial products are available for in vitro transcription/translation systems from, for instance, Ambio (Austin, Tex.) and Promega (Madison, Wis.).

Pharmaceutical Compositions and Methods of Use

The compositions of the invention are useful in applications for inducing immune responses. Accordingly, the invention provides a method of administering a composition of the invention to an animal in order to provoke an immune system in the animal. The compositions and methods described herein can be used for vaccination against substantially any human or other vertebrate pathogen (viral, bacterial, prion), or any other antigen of interest. In another method, a human patient is immunized against a *Plasmodium* infection by administering a composition comprising MSP-8 linked to MSP-$1_{19}$. In a preferred embodiment, the MSP-8 and MSP-$1_{19}$ components in the composition are *P. falciparum* sequences. In another preferred embodiment, MSP-$1_{19}$ is linked via a 5-glycine linker peptide to the N-terminal of MSP-8.

In embodiments of the methods, a combination comprising two or more different compositions of the invention are administered. For instance, multiple antigens from the same pathogen may be used to prepare a multivalent vaccine. Antigens may also be from different strains of a pathogen to prepare a multivalent vaccine. Combination immunization encompasses administering a single vaccine comprising two or more different molecules. Combination immunization also encompasses administering different molecules at separate sites in an animal.

The invention also encompasses a method of producing a neutralizing antibody. The method comprises administering an immunogenic amount of a composition of the invention to a mammal. That is, a detectable immune response can be elicited in the mammal such that a neutralizing antibody is produced that can detectably inhibit a pathogen function that is associated with, or mediates, pathogen infection. In a preferred embodiment, the composition of the invention comprises MSP-8 linked to MSP-$1_{19}$. This novel composition provides a useful immunogenic molecule that can elicit a neutralizing antibody recognizing at least one functional core domain of a *Plasmodium* polypeptide, thereby producing a neutralizing antibody that specifically binds with a polypeptide domain required for *Plasmodium* function and/or infection.

One skilled in the art would appreciate, based upon the disclosure provided herein, that the immunogenic dose of a composition of the invention comprising MSP-8 linked to MSP-$1_{19}$ may be a useful therapeutic to treat and/or alleviate a malarial infection in a human both before and after exposure to the *Plasmodium* parasite. That is, the immunogenic dose may be administered prior to, during, or after infection of a human by a *Plasmodium* spp. Thus, the invention embraces both prophylactic and therapeutic uses for a composition of the invention.

The skilled artisan would understand, based upon the disclosure provided herein, that a neutralizing antibody of the invention can be produced in a mammal in order to treat, alleviate, or prevent pathogen infection in that mammal, where the mammal is in need thereof. Further, the neutralizing antibody can be produced in one mammal and can be administered to another mammal in need thereof (i.e., passive immunization) to inhibit or prevent pathogen infection in the mammal that receives the antibody. Methods for preventing and/or inhibiting pathogen infection in a mammal using a neutralizing antibody are known in the art and are not further described herein.

In the methods of the invention, a molecule of the invention can be administered to any animal having an adaptive immune system in order to induce an immune response. Animals useful in practicing the methods of the invention include, but are not limited to, mammals, fish and reptiles. Preferably the mammal is a primate, more preferably a human. Non-human primates may also be used in the invention. Mammals including mice, rats, rabbits, goats, horses, sheep, cattle and the like are also included.

The invention further provides pharmaceutical compositions comprising a composition of the invention that are useful, for example, in practicing the methods of the invention. Thus, the preparation and use of pharmaceutical or veterinary compositions comprising MSP-8 linked to an antigen as an active ingredient are encompassed by the invention. Such a pharmaceutical composition may consist of the linked active ingredient alone, in a form suitable for administration to a subject, or the pharmaceutical composition may comprise the linked active ingredient and one or more pharmaceutically acceptable carriers, one or more additional ingredients, or some combination of these. Administration of one of these pharmaceutical compositions to a subject is useful for treating, ameliorating, relieving, inducing an immune response against, preventing, inhibiting, or reducing any of a variety of disorders in the subject, as described elsewhere in the present disclosure. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a vehicle or one or more other accessory ingredients, and then, if necessary or desirable, shaping or packaging the product into a desired single- or multi-dose unit.

It will be appreciated that the precise formulation and dosage amounts will vary depending upon any number of factors, including, but not limited to, the type and severity of the disease to be treated, the route of administration, the age and overall health of the individual, etc. However, the preparation of a pharmaceutically acceptable composition having an appropriate pH, isotonicity, stability and other characteristics is within the skill of the art. Pharmaceutical compositions are described in the art, for example, in Remington's Pharmaceutical Sciences (1985, Genaro, ed., Mack Publishing Co., Easton, Pa.).

Although the descriptions of pharmaceutical compositions provided are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be prepared, packaged, or sold in formulations suitable for gastrointestinal, oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

Preferably, the composition of the invention is administered by a parenteral route.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intravenous, intra-arterial, intramuscular, or intrasternal injection and intravenous, intra-arterial, or kidney dialytic infusion techniques.

Formulations of a pharmaceutical composition suitable for parenteral administration comprise a composition of the invention combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules, in multi-dose containers containing a preservative, or in single-use devices for auto-injection or injection by a medical practitioner. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable carrier (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Pharmaceutical compositions of the invention for use as vaccines may further comprise adjuvants. Examples of adjuvants useful in these vaccines include, but are not limited to, aluminum salts, ISCOMs, Montanide™ ISA720 and ISA51 (Seppic, Paris, France), MF59, unmethylated CpG, quill glycosides, Quil A, QS21, monophosphoryl lipid A (MPL), AS02A, liposomes, bacterial mitogens and toxins and other TLR agonists. In one embodiment, the adjuvant is Quil A.

When the vaccine comprises an isolated nucleic acid encoding a molecule of the invention, the DNA-based vaccine may be prepared following the disclosure described in Wang et al. (1993, Proc. Natl. Acad. Sci. USA 90:4156-4160) for mice immunization. The nucleic acid vaccine comprises DNA encoding a fusion protein comprising MSP-8 linked to a polypeptide antigen expressed under the control of any of the promoters disclosed herein or known in the art. Antibodies are raised against the expressed protein by intramuscular injection of DNA. To adapt this DNA-based vaccine to human subjects, the amounts of DNA, the route of injection and the adjuvants to be used can vary from that described in Wang. However, these variations will be readily apparent to the skilled artisan working in the field of nucleic acid-based vaccines.

The skilled artisan would understand that the nucleic acids of the invention encompass an RNA or a DNA sequence encoding a protein, e.g., MSP-8 or an antigen, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Antibodies Against a Composition of the Invention

The invention also provides antibodies against a composition of the invention. Such antibodies are useful for diagnostic, research and therapeutic applications, such as passive immunization. In a preferred embodiment, the antibodies specifically bind a molecule of the invention. In one embodiment, the antibody specifically binds to a molecule comprising MSP-8 covalently linked to MSP-$1_{19}$. In one embodiment, the antibody specifically binds to SEQ ID NO. 23. In a preferred embodiment, the antibody specifically binds to a molecule in which both MSP-8 and MSP-$1_{19}$ are $P.$ $falciparum$ or $P.$ $vivax$ sequences, or substantial homologs thereof. In one embodiment, the antibody is polyclonal. In another, the antibody is monoclonal. The antibody may also be one of a humanized antibody, a synthetic antibody, a heavy chain antibody, and a biologically active fragment of an antibody, wherein the biologically active fragment comprises an Fv fragment, an Fab fragment or an F(ab)$_2$ fragment. A heavy chain antibody may be one of a camelid antibody, a heavy chain disease antibody, and a variable heavy chain immunoglobulin.

Camelid antibodies differ from those of most other mammals in that they lack a light chain, and thus comprise only heavy chains with complete and diverse antigen binding capabilities (Hamers-Casterman et al., 1993, Nature, 363: 446 448). Such heavy-chain antibodies are useful in that they are smaller than conventional mammalian antibodies, they are more soluble than conventional antibodies, and further demonstrate an increased stability compared to some other antibodies.

The generation of polyclonal antibodies is accomplished by inoculating the desired animal with a composition of the invention comprising MSP-8 linked to an antigen and isolating antibodies which specifically bind the antigen therefrom. The production of polyclonal sera from camelid species is substantively similar to the production of polyclonal sera from other animals such as sheep, donkeys, goats, horses, mice, chickens, rats, and the like. The skilled artisan, when equipped with the present disclosure and the methods detailed herein, can prepare high-titers of antibodies from a camelid species with no undue experimentation. Camelid species for the production of antibodies and sundry other uses are available from various sources, including but not limited to, Camello Fataga S. L. (Gran Canaria, Canary Islands) for Old World camelids, and High Acres Llamas (Fredricksburg, Tex.) for New World camelids.

Monoclonal antibodies directed against a composition of the invention may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Human monoclonal antibodies may be prepared by the method described in U.S. patent publication 2003/0224490. Quantities of the desired peptide may also be synthesized using chemical synthesis technology. Monoclonal antibodies directed against a molecule of the invention may be generated from mice, or other mammal, immunized with the molecule using standard procedures as referenced herein.

Nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., supra, 2001.

Bacteriophage that encode the desired antibody may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (seFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al., 1995, J. Mol. Biol. 248:97-105).

Kits

The invention also includes a kit comprising a composition of the invention and an instructional material which describes administering the molecule to an animal to induce an immune response. In an embodiment, this kit further comprises a (preferably sterile) pharmaceutically acceptable carrier suitable for dissolving or suspending the molecule of the invention prior to administering the molecule to the animal. Optionally, the kit comprises an applicator for administering the molecule. In one embodiment, the molecule in the kit comprises MSP-8 linked to MSP-$1_{19}$. Preferably, both MSP-8 and MSP-$1_{19}$ are P. falciparum or P. vivax sequences, or sequences substantially homologous thereto.

A kit comprising an antibody that specifically binds a composition comprising MSP-8 linked to an antigen and an instructional material is also provided. In one embodiment, the composition comprises MSP-8 linked to MSP-$1_{19}$. Preferably, the antibody specifically binds to a molecule comprising MSP-8 linked to MSP-$1_{19}$, wherein both are P. falciparum or P. vivax sequences, or sequences substantially homologous thereto. In one embodiment, the composition comprises SEQ ID NO. 23.

A kit providing a nucleic acid encoding a composition of the invention comprising a fusion of a polypeptide antigen to MSP-8 and an instructional material is also provided. In one embodiment, the nucleic acid is SEQ ID NO. 22.

The composition in a kit of the invention may be present in the kit as a sterile solution in a pharmaceutically acceptable carrier or in solid form that can be solubilized or suspended with a pharmaceutically acceptable carrier. A container of a pharmaceutically acceptable carrier is optionally provided in a kit with a composition of the invention in solid form.

The instructional material in each kit simply embody the disclosure provided herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods used in the following Experimental Examples are now described.

Mice and parasites: Male BALB/cByJ mice, five to six weeks of age, were purchased from The Jackson Laboratory (Bar Harbor, Me.). All animals were housed in the Animal Care Facility of Drexel University College of Medicine under specific pathogen free conditions. The lethal 17XL and non-lethal 17X strains of P. yoelii were originally obtained from Dr. William P. Weidanz (University of Wisconsin, Madison, Wis.).

Expression and purification of PyMSP-1 and PyMSP-8 recombinant proteins: rPyMSP-$1_{42}$ and PyMSP-8. For the pymsp-$1_{42}$ construct, a 1080 bp fragment derived from the 3' end of the P. yoelii 17XL MSP-1 gene (nucleotide 4380-5451, accession #J04668 (Lewis, 1989, Mol. Biochem. Parasitol. 36: 271-82)) was PCR amplified from P. yoelii 17XL genomic DNA using oligonucleotide primers 5'-GAA-CATATGCCAGAAAAAGATATT-3' (5' primer; SEQ ID NO: 14) and 5'-TGAGGATCCCATTTAGCTGGAAGA-3' (3' primer; SEQ ID NO: 15). To facilitate subcloning, NdeI and BamHI restriction sites were incorporated into the 5' and 3' primers, respectively. The amplified fragment was gel purified, digested with NdeI and BamHI, and ligated into NdeI/BamHI-digested pET-15b (Novagen, Madison, Wis.). Using the pET/T7 RNA polymerase expression system with E. coli BL21(DE3)(pLysS) host strain, a 42 kDa recombinant antigen (rPyMSP-$1_{42}$) was produced that represents the C-terminus of PyMSP-1; minus the hydrophobic anchor sequence. This recombinant PyMSP-$1_{42}$ contains 20 plasmid-encoded amino acids (SEQ ID NO. 13) fused to its N-terminus, which includes six histidine residues. rPyMSP-$1_{42}$ was purified from an insoluble fraction of bacterial lysate by Ni—NTA affinity chromatography under denaturing conditions (Burns et al., 2003, Vaccine 21: 1843-1852). To promote formation of disulfide bonds, the denaturant was gradually removed by dialysis in the presence of reduced and oxidized glutathione (10:1 ratio), as previously reported for rPyMSP-8 (Burns et al., 2000, Infect. Immun. 68: 6189-6195; Shi et al., 2005, Infect. Immun. 73: 6363-6371), as well as MSP-$1_{42}$ and AMA-1 of P. chabaudi. The expression and purification of full-length recombinant PyMSP-8 (rPyMSP-8) from P. yoelii 17XL followed a similar protocol and has been previously described in detail (Burns et al., 2000, Infect. Immun. 68: 6189-6195; Shi et al., 2006, Mol. Biochem. Parasitol. 149: 231-41; Shi et al., 2005, Infect. Immun. 73: 6363-6371).

GST-PyMSP-$1_{19}$ and GST-PyMSP-8C. Previously published protocols for the expression and purification of the C-terminal portion of PyMSP-1 fused to Schistosoma japonicum glutathione S-transferase (GST-PyMSP-$1_{19}$) were followed (Daly et al., 1993, Infect. Immun. 61:2462-2467). Briefly, a 417 bp fragment encoding the 3' end of pymsp-1 gene (nucleotide 5044-5459 accession #J04668) was PCR amplified from P. yoelii 17XL genomic DNA, using oligonucleotides 5'-CCCGAATTCACATAGCCTCAATAGCTT-TAA-3' (5' primer; SEQ ID NO: 16) and 5'-CCCGAATTC TCCCATAAAGCTGGA-3' (3' primer; SEQ ID NO 17) as primers.

A similar approach was taken for the generation of a comparable construct, based on PyMSP-8, which encodes GST-PyMSP-8C. A 393 bp fragment encoding the C-terminus of PyMSP-8 gene (nucleotides 1021-1413, accession #AY005132 (Burns et al., 2000, Infect. Immun. 68: 6189-6195)) was PCR amplified using oligonucleotide primers 5'-ATGGATCCATAACTATACTTAATTTAGCAAATGGT-3' (5' primer; SEQ ID NO: 18) and 5'-GGGAATTCAACT-TGAACAATAAATACCATCTCC-3' (3' primer; SEQ ID NO: 19).

The amplified fragment encoding PyMSP-$1_{19}$ was inserted into the EcoRI site of the pGEX/2T expression vector (Amersham Biosciences, Piscataway, N.J.). The amplified fragment encoding PyMSP-8 was cloned into BamHI and EcoRI digested pGEX/2T plasmid. The correct orientation of each insert was determined by restriction enzyme digestion. Fusion proteins GST-PyMSP-$1_{19}$ and GST-PyMSP-8C were expressed from their respective constructs using E. coli XL-1 Blue as the host strain (Stratagene, La Jolla, Calif.). Recombinant GST-PyMSP-$1_{19}$ and GST-PyMSP-8C were purified from the soluble lysate of isopropyl-β-D-thiogalactopyranoside (IPTG)-induced bacterial cells by affinity chromatography using a glutathione agarose column (Amersham Biosciences) as previously described (Daly et al., 1993, Infect.

Immun. 61:2462-2467; Daly et al., 1995, J. Immunol, 155: 236-243). For control immunizations, non-fused GST was purified as above from *E. coli* transformed with the pGEX/2T vector containing no inserted DNA.

The concentrations of recombinant proteins were determined using the bicinchoninic acid protein assay (Pierce Biotechnology Inc., Rockford Ill.). Protein purity and conformation were assessed by Coomassie blue staining following SDS-PAGE, run under both reduced and non-reduced conditions. Corresponding immunoblots were probed with the monoclonal antibody mAb302 (Majarian ET AL., 1984, J. Immunol. 132: 3131-3137) for recombinant PyMSP-1 antigens and with rabbit anti-PyMSP-8 sera (Burns ET AL., 2000, Infect. Immun. 68: 6189-6195) for GST-PyMSP-8C. The yields of purified rPyMSP-$1_{42}$ and GST-PyMSP-$1_{19}$ were approximately 12 and 4 mg per liter of induced bacterial culture, respectively. The yields of purified rPyMSP-8 and GST-PyMSP-8C were both about 1.5 mg per liter of induced bacterial culture.

Construction and expression of recombinant PyMSP-1/8 chimeric antigen: A 414 bp fragment encoding pymsp-$1_{19}$ was PCR amplified from the pGEX/PyMSP-$1_{19}$ plasmid described above, using oligonucleotides 5'-GCCCATATG-CACATAGCCTCAATAGCTTTAA-AC-3' (5' primer; SEQ ID NO: 20) and 5'-CCCATATGACCACCACCACCTC-CCATAAAG-CTGGAAGAACT-3' (3' primer; SEQ ID NO: 21) as primers. A spacer comprising four glycine residues was incorporated into the 3' primer. The four primer-encoded glycines are immediately adjacent to the C-terminal glycine residue of PyMSP-$1_{19}$, resulting in five consecutive glycines as part of the spacer. To facilitate subcloning, NdeI restriction sites were added to both the 5' and 3' primers. The amplified fragment was gel purified, digested with NdeI, and ligated into NdeI-digested pET-15/PyMSP-8 plasmid. Plasmids with inserts were digested by EcoRV to assess the orientation of the inserted fragment. For expression, a clone with the correct orientation was transformed into Origami(DE3)pLysS *E. coli* cells, a K-12 derivative with mutations in both the thioredoxin reductase (trxB) and glutathione reductase (gor) genes to facilitate disulfide bond formation (Novagen, Madison, Wis.). The nucleic acid sequence of the chimeric rPyMSP-1/8 protein is shown in SEQ ID NO. 22. The deduced amino acid sequence (SEQ ID NO. 23) contains 21 vector-encoded residues at the N-terminus (SEQ ID NO: 13), which includes a six His-tag, joined to PyMSP-$1_{19}$, followed by spacer residues and then the full-length, mature PyMSP-8. The predicted molecular weight of rPyMSP1/8 is about 59-60 kDa.

Purification of recombinant PyMSP-1/8: At the mid-log phase of growth, rPyMSP-1/8 expression was induced by the addition of IPTG to a final concentration of 1 mM, and incubation continued for 3 hour at 37° C. Bacteria were harvested, washed, resuspended in lysis buffer (50 mM Tris-HCl, pH 8.0, 500 mM NaCl, 10 mM EDTA) and treated for 2 hours with lysozyme (0.5 mg/ml). Following lysis, viscosity was reduced by brief sonication. The rPyMSP-1/8 antigen was purified from a soluble fraction of lysed bacteria obtained following centrifugation for 30 min at 40,000×g. A 30% ammonium sulfate fraction of the initial lysate was dialyzed into 20 mM Tris-HCl, pH 8.0, 500 mM NaCl at 4° C., overnight. The fraction was recovered from dialysis and cycled over a nickel-chelate affinity chromatography column at 4° C. (Ni—NTA Superflow matrix, Qiagen, Inc., Valencia, Calif.) under non-denaturing conditions. The column was washed, eluted and fractions were examined by SDS-PAGE. Fractions containing rPyMSP-1/8 were combined and dialyzed into renaturation buffer (50 mM Tris-HCl, pH 8.3, 500 mM NaCl, 3 mM reduced glutathione, 0.3 mM oxidized glutathione) containing 4 M guanidine-HCl. The concentration of guanidine-HCl was gradually removed by dialysis, in the presence of reduced and oxidized glutathione (Scheele et al., 1982, J. Biol. Chem. 257: 12277-12282). Following dialysis into 20 mM Tris-HCl (pH 8.0) and 500 mM NaCl, rPyMSP-1/8 was further purified on a second Ni—NTA affinity column, under non-denaturing conditions. The final protein concentration and purity were determined as above. The yield of purified rPyMSP-1/8 was approximately 0.5-1 mg per liter of induced bacterial culture.

Immunizations and experimental infections: Groups of 4 to 10 BALB/cByJ mice were immunized subcutaneously (2 sites) with various recombinant MSP proteins formulated with Quil A (25 µg; Accurate Chemical and Scientific Corporation, Westbury, N.Y.) as adjuvant. For immunization, doses of recombinant antigen per mouse were varied from 1 to 50 µg (see Table 1 and Figure legends). For the combined formulation, rPyMSP-$1_{42}$ and rPyMSP-8 were mixed in saline with adjuvant just prior to injection. Control groups were immunized with non-fused GST formulated with Quil A or with Quil A alone.

In all experiments, mice received three immunizations, at three week intervals with the same dose of antigen and adjuvant used for the priming immunization. Two weeks following the last immunization, all mice were challenged by intraperitoneal injection of $1 \times 10^5$ *P. yoelii* 17XL- or *P. yoelii* 17X-parasitized RBCs obtained from a donor mouse.

Blood parasitemia was monitored by enumeration of parasitized erythrocytes in thin tail-blood smears stained with Giemsa. In accord with Institutional Animal Care and Use policy, *P. yoelii* 17XL infections were considered lethal when parasitemia exceeded 50%, at which time animals were euthanized.

ELISA: Approximately 2-3 days prior to *P. yoelii* challenge infection, a small volume of serum was collected from each immunized mouse, and the titers of antigen-specific antibodies were measured by ELISA. For mice immunized with rPyMSP-$1_{42}$, titers were determined using wells coated with rPyMSP-$1_{42}$ or GST-PyMSP-$1_{19}$. For mice immunized with rPyMSP-8, titers were determined using wells coated with rPyMSP-8 or GST-PyMSP-8C. For mice immunized with the combination of rPyMSP-$1_{42}$ and rPyMSP-8 or with the chimeric rPyMSP-1/8, titers were determined using wells coated with each of the four recombinant MSP antigens.

Antigen coated wells (0.25 µg/well) were washed and blocked for 1 hour with TBS (25 mM Tris-HCl, pH 8.0, 150 mM NaCl) containing 5% non-fat dry milk. Serial two-fold dilutions of each sera in TBS-0.1% Tween 20 containing 1% BSA were added to antigen coated wells and incubated for 1 hour at room temperature. Bound antibodies were detected using horseradish peroxidase-conjugated rabbit antibody specific for mouse IgG (Zymed Laboratories, South San Francisco, Calif.). The mean absorbance of sera from adjuvant control mice (n=5) was subtracted as background. Titer was defined as the dilution of sera that yielded an $OD_{405}$ of 0.5. *P. yoelli* hyperimmune serum was included on each assay as an internal reference to normalize the data between assays. To generate this pool of hyperimmune sera, mice were infected with $1 \times 10^5$ *P. yoelii* 17X parasitized RBCs (day 0). Following parasite clearance, mice were rechallenged on day 60 and again on day 90 with $1 \times 10^7$ *P. yoelii* 17X parasitized RBCs. Serum was collected 2 weeks following the last parasite challenge.

Statistical Analysis: The statistical significance of differences in antibody responses and in mean peak parasitemia between groups was calculated by analysis of variance. The significance of differences in the number of surviving animals between groups was determined by the Mantel-Haenszel logrank test (GraphPad Prism 4.0, GraphPad Software Inc., San Diego, Calif.).

Experimental Example 1

Comparison of PyMSP-1 and PyMSP-8 Vaccine Efficacy Against P. yoelii 17XL Challenge Infection An initial series of immunization and challenge studies was conducted to compare the relative efficacy of immunization with various PyMSP-1 and PyMSP-8 recombinant antigens at several antigen doses. Quil A was selected as adjuvant based on a large set of PyMSP-8 immunogenicity and efficacy data (Shi et al., 2005, Infect. Immun. 73: 6363-6371) and minimal adjuvant toxicity at the site of injection.

Figure 2B:
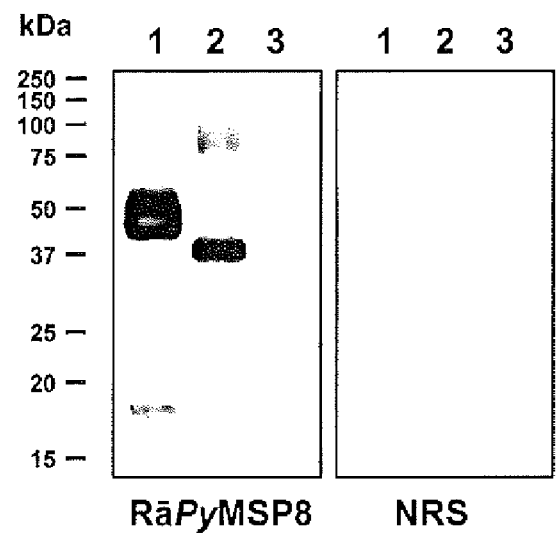

Recombinant MSP antigens prepared included rPyMSP-$1_{42}$, full-length rPyMSP-8 and two glutathione S-transferase (GST) fusion proteins, GST-PyMSP-$1_{19}$ and GST-PyMSP-8C, that contained only the C-terminal EGF-like domains of PyMSP-1 and PyMSP-8, respectively. Protein purity and conformation were assessed by SDS-PAGE and immunoblot analysis. Coomassie-blue stained gels of these recombinant MSP antigens run under reducing (FIG. 1A) and non-reducing conditions (FIG. 1B) are shown in FIG. 1. The corresponding immunoblots of non-reduced antigens to further evaluate conformation are shown using mAb302 specific for PyMSP-1 (FIG. 2A) and polyclonal rabbit antiserum raised against refolded PyMSP-8 (FIG. 2B). Based on relative migration on SDS-polyacrylamide gels and presence of a single, dominant reactive band on immunoblots, the recombinant PyMSP-1 and PyMSP-8 antigens appeared to be properly folded.

BALB/cByJ mice were immunized and boosted twice with each MSP vaccine formulation, prior to P. yoelii 17XL challenge infection. The data were compiled from 6 immunizations and challenge experiments (4-5 mice/group/experiment). The results of six efficacy trials are summarized in Table 1.

TABLE 1

Protection Induced by Immunization with PyMSP-1 and PyMSP-8 recombinant antigens[a]

| Antigen | Dose (μg/immunization)[b] | % Parasitemia Day 8 | Survival[c] |
|---|---|---|---|
| rPyMSP-8 | 1 | 16.9 ± 16.0[d] | 3/5[e] |
|  | 5 | 5.6 ± 3.3[d] | 5/5[e] |
|  | 10 | 2.1 ± 2.2[d] | 9/10[e] |
|  | 25 | 4.6 ± 3.1[d] | 5/5[e] |
| GST-PyMSP-8C | 10 | 52.4 ± 17.9 | 0/14 |
|  | 25 | 47.9 ± 17.4 | 0/5 |
|  | 50 | 39.6 ± 4.0 | 0/5 |
| rPyMSP-$1_{42}$ | 1 | 25.0 ± 23.4[d] | 0/5 |
|  | 5 | 26.9 ± 22.3[d] | 1/5 |
|  | 10 | 40.6 ± 18.5 | 1/9 |
|  | 25 | 29.0 ± 20.8[d] | 3/10[e] |
| GST-PyMSP-$1_{19}$ | 10 | 24.0 ± 23.1[d] | 6/15[e] |
|  | 25 | 8.5 ± 10.9[d] | 2/4[e] |
| GST control | 10 | 64.5 ± 17.8 | 0/5 |
|  | 25 | 52.2 ± 15.1 | 0/5 |
|  | 50 | 46.0 ± 22.5 | 0/4 |
| Quil A control | — | 47.7 ± 16.8 | 0/28 |

[a]Data compiled from 6 immunization and challenge experiments (4-5 mice/group/experiment).
[b]All animals were immunized 3 times at 21 day intervals with the indicated amount of each recombinant antigen formulated with Quil A as adjuvant (25 μg/dose).
[c]Clearance of P. yoelii 17XL blood-stage parasites, with maximum parasitemia not exceeding 50% in any animal.
[d]Significantly reduced compared to Quil A controls, ANOVA, p < 0.05
[e]Significantly different compared to Quil A controls, considering survival period and % mortality, Mantel-Haenszel logrank test, p < 0.05

As expected, immunization with mature, full-length rPyMSP-8, reproducibly protected 90-100% of mice against lethal P. yoelii 17XL malaria. In all groups of rPyMSP-8 immunized mice, mean parasitemia on day 8 of infection was significantly reduced (p<0.05) relative to adjuvant controls, indicative of the delay in ascending parasitemia (Table 1). Furthermore, 90-100% of rPyMSP-8 immunized mice (5, 10 and 25 μg doses) survived a lethal P. yoelii 17XL challenge infection. Significant protection was even noted following immunization with as little as 1 μg of antigen/mouse/immunization. In contrast to full-length rPyMSP-8, immunization with GST-PyMSP-8C provided no protection against P. yoelii 17XL malaria, even with high antigen doses (50 μg/immunization). rPyMSP-$1_{42}$ immunized mice exhibited a significant, but modest reduction in day 8 parasitemia and 20-30% survival rate (p<0.05), but protection was variable with respect to antigen dose. In contrast to MSP-8, immunization with GST-PyMSP-$1_{19}$ (10-25 μg/dose) partially protected (p<0.05) mice to a level similar to that achieved with rPyMSP-$1_{42}$ (25 μg/dose). In mice immunized with recombinant PyMSP-1 or PyMSP-8 antigens, protection could not be readily correlated with the prechallenge titer of antibodies against the immunizing antigen. No protection was ever observed in mice immunized with the GST carrier protein alone formulated with Quil A or with Quil A alone.

These data indicate that for any combined MSP-1 and MSP-8 vaccine formulation, immunization with substantially full-length rPyMSP-8 will likely be required for effective immunization. In addition, rPyMSP-8-induced protection against lethal P. yoelii malaria was consistently better than that achieved by immunization with comparable doses of rPyMSP-$1_{42}$ or GST-PyMSP-$1_{19}$ when utilizing Quil A as adjuvant.

Experimental Example 2

Figure 3:
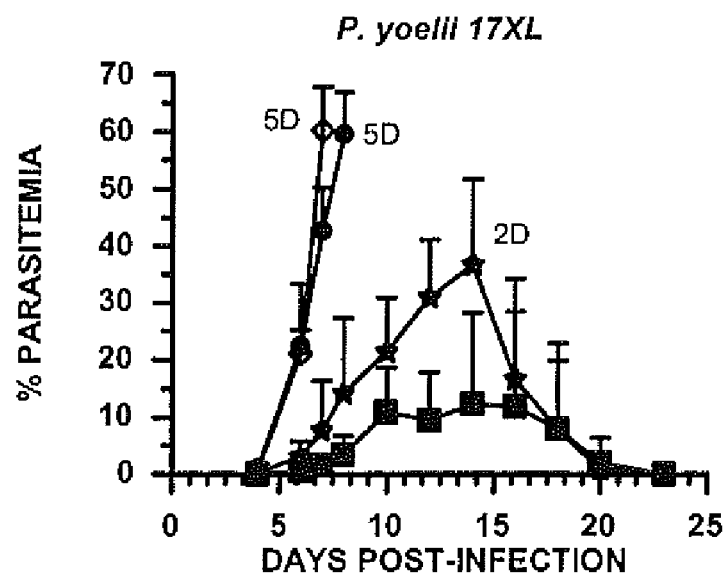
FIGS. 3A and 3B depict graphs regarding vaccine efficacy of co-immunization with rPyMSP-1$_{42}$ and rPyMSP-8.
Figure 3:
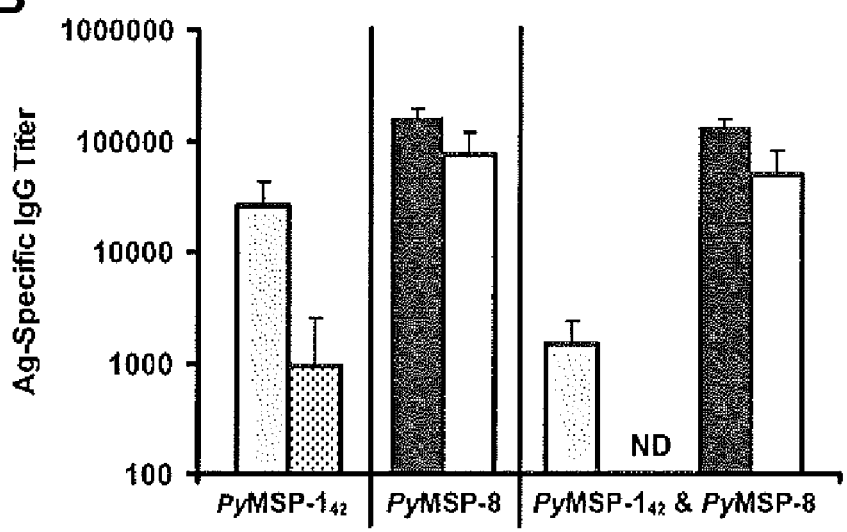

Combined Immunization with rPyMSP-$1_{42}$ and rPyMSP-8 Does Not Improve Protection Against P. yoelii 17XL Infection To test if a combined antigen formulation could improve overall vaccine efficacy, BALB/cByJ mice were immunized with rPyMSP-$1_{42}$ (10 μg), rPyMSP-8 (10 μg) or a combination of rPyMSP-$1_{42}$ and rPyMSP-8 (10 μg+10 μg), formulated with Quil A as adjuvant. As shown in FIG. 3A, rPyMSP-8-immunized mice were protected against an otherwise lethal P. yoelii 17XL challenge infection, with peak parasitemia occurring 12-16 days post-challenge with a mean of 16.3%±14.6%. All mice immunized with Quil A alone developed fulminant, unremitting parasitemia by day 8 of infection. Immunization with rPyMSP-$1_{42}$ at 10 μg/dose did not afford any significant level of protection.

Unexpectedly, no increase in protection was observed in mice immunized with the combination of rPyMSP-$1_{42}$ and rPyMSP-8, In fact, only three animals immunized with the combination controlled a lethal P. yoelii 17XL infection. Through day 14 of infection, the mean peak parasitemia in mice immunized with both rPyMSP-$1_{42}$ and rPyMSP-8 was 39.5%±13.0%, significantly higher than that in mice immunized with only rPyMSP-8 (p<0.05). Two animals from the same group showed a delay in the onset of patent parasitemia but were sacrificed on day 14 when parasitemia exceeded 50%. Thus, protection against P. yoelii 17XL malaria induced by immunization with rPyMSP-8 alone was actually better than that achieved by immunization with the combination of rPyMSP-$1_{42}$ and rPyMSP-8.

To determine if there were differences in the immunogenicity of rPyMSP-$1_{42}$ and rPyMSP-8 formulated alone or in combination, antibodies present in prechallenge immunization sera specific for rPyMSP-$1_{42}$ and rPyMSP-8 were measured by ELISA. To assess the response to conformational epitopes associated with the double EGF-like domains of each antigen, immunization-induced antibodies reactive with GST-PyMSP-1$_{19}$ and GST-PyMSP-8C were also measured. As shown in FIG. 3B, immunization with rPyMSP-8 induced a high level of antibodies against rPyMSP-8, a significant portion of which also bound to its C-terminal EGF-like domains. The overall antibody response induced by immunization with rPyMSP-1$_{42}$ was also strong, but was significantly less than that observed for rPyMSP-8 (p<0.01). Distinct from that observed with PyMSP-8, a smaller proportion of the total anti-PyMSP-1$_{42}$ antibody induced recognized the EGF-like domains of PyMSP-1$_{19}$. Most importantly, the response to PyMSP-1$_{42}$ was markedly inhibited in mice immunized with the combination of rPyMSP-1$_{42}$ and rPyMSP-8, with little or no antibodies to protective PyMSP-1$_{19}$ epitopes detected (p<0.05). These data are indicative of a significant level of competition between the two MSP vaccine antigens when formulated in combination and of the immunodominance of rPyMSP-8 over rPyMSP-1$_{42}$.

Experimental Example 3

Production and Analysis of a Chimeric PyMSP-1$_{19}$ and PyMSP-8 Vaccine

Figure 4A:
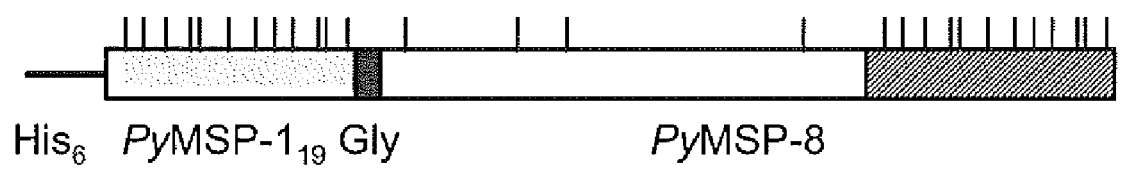
FIGS. 4A, 4B and 4C depict a schematic of a fusion protein and a series of images of protein gels and immunoblots.

Immunization with rPyMSP-8 provided the necessary T cell epitopes to promote a strong antibody response to B cell determinants associated with its C-terminal EGF-like domains. This was not the case with rPyMSP-1$_{42}$, creating an obstacle for the combined antigen immunization. To focus the antibody response on the protective EGF-like domains of PyMSP-1 while continuing to provide malaria-specific T cell help, a chimeric antigen gene was constructed (FIG. 4A).

The expressed recombinant protein contained the protective EGF-like domains of MSP-1 (PyMSP-1$_{19}$) linked via a glycine spacer to the N-terminus of full-length PyMSP-8. The conformation of the purified chimeric antigen was assessed based on its migration on SDS-PAGE (reduced vs. non-reduced) and its corresponding immunoblot reactivity with mAb302, which recognizes a conformational epitope on the first EGF-like domain of PyMSP-1$_{19}$, and with polyclonal rabbit antibodies raised against refolded rPyMSP-8.

Figure 4B:
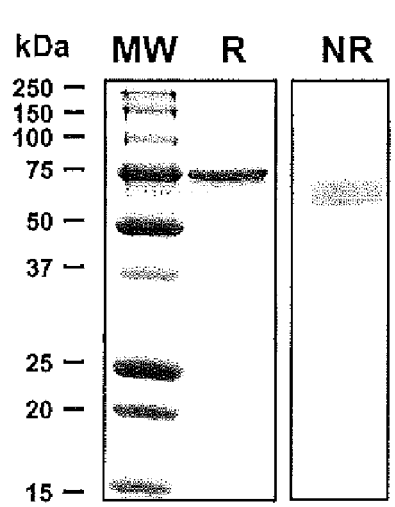
Figure 4C:
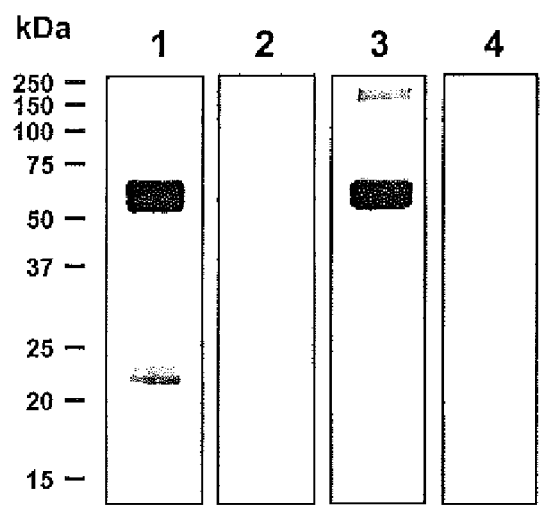

As shown in FIG. 4B, chimeric rPyMSP-1/8 migrated as a predominant band of about 60 kDa in the presence of 2-mercaptoethanol (R) and as a faster migrating doublet in the absence of 2-mercaptoethanol (NR). As shown by immunoblot analysis, the 60 kDa rPyMSP-1/8 was strongly reactive with the PyMSP-1$_{19}$ specific monoclonal antibody mAb302 and with polyclonal rabbit anti-refolded rPyMSP-8 sera (FIG. 4C). Higher molecular weight aggregates of refolded rPyMSP-1/8 run under non-reducing conditions were minimal. A smaller band of about 22 kDa was detected by immunoblot using mAb302 under non-reducing conditions. This band was not detected by the rabbit anti-PyMSP-8 sera, suggesting that the fragment is an N-terminal cleavage product containing PyMSP-1$_{19}$. Overall, the data indicate that in a high proportion of chimeric rPyMSP-1/8 proteins, the conformational epitopes of PyMSP-1$_{19}$ and PyMSP-8 appear intact.

Experimental Example 4

Immunization with the Chimeric rPyMSP-1/8 Vaccine Markedly Enhances Protection Against *P. yoelii* 17XL Malaria To compare immunogenicity and protective efficacy, groups of BALB/cByJ mice were immunized with rPyMSP-8 (10 µg) or with an equimolar dose of the chimeric rPyMSP-1/8 antigen (14 µg), formulated with Quil A as adjuvant, or with adjuvant alone. Two weeks after the third immunization, prechallenge serum samples were collected, and immunization-induced antibodies were quantitated by ELISA. Groups of mice were subsequently challenged with *P. yoelii* 17XL, the lethal strain that invades both normocytes and reticulocytes or with nonlethal *P. yoelli* 17X parasites that preferentially invade reticulocytes.

Figure 5:
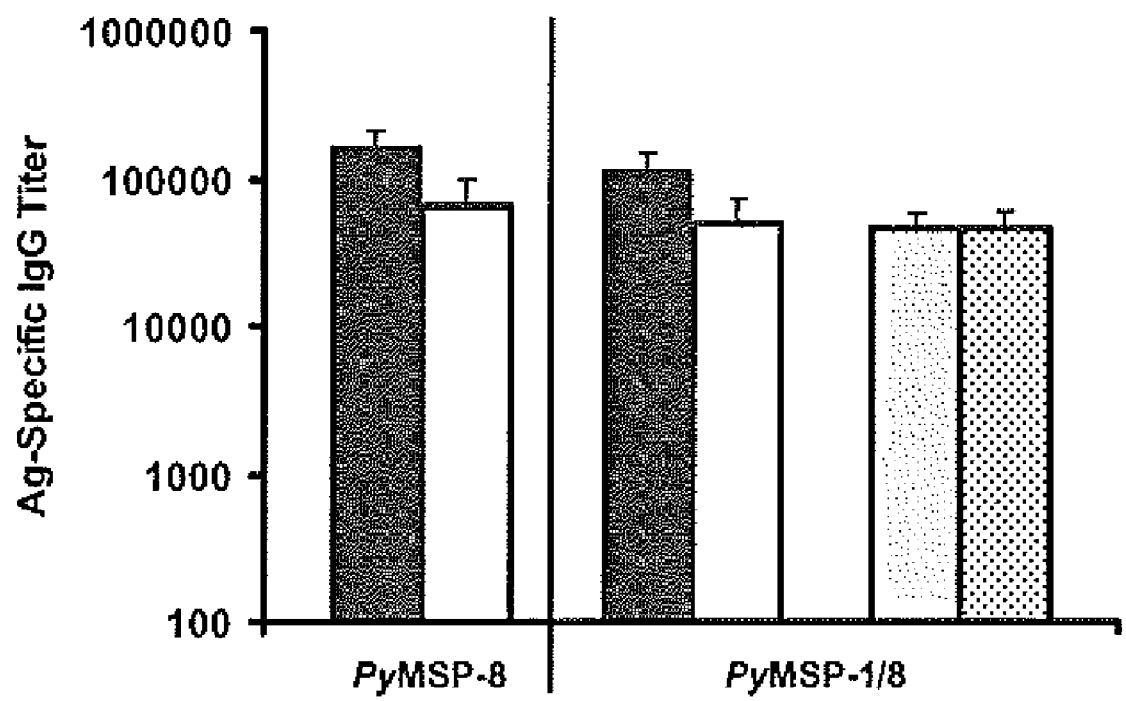
FIG. 5 is a graph of MSP-specific antibody response induced by immunization with the chimeric rPyMSP-1/8. BALB/cByJ mice (n=5) were immunized and boosted twice with rPyMSP-8 or the chimeric rPyMSP-1/8 formulated with Quil A as adjuvant. Serum samples were collected two weeks following the third immunization. Prechallenge antibody titers (mean±SD) against rPyMSP-1$_{42}$ (▨), GST-PyMSP-1$_{19}$ (▩), rPyMSP-8 (■) and GST-PyMSP-8C (□) determined by ELISA are shown. Immunization groups are indicated along the x-axis.

As shown in FIG. 5, immunization with rPyMSP-8 or rPyMSP-1/8 induced a high and comparable level of IgG that recognized full-length PyMSP-8. In both groups of immunized animals, a high proportion of the total anti-PyMSP-8 antibody also recognized epitopes on the C-terminal EGF-like domains, as measured by reactivity with GST-PyMSP-8C.

More importantly, an equally high titer of antibodies was induced by rPyMSP-1/8 immunization which recognized the protective EGF-like domains of PyMSP-1, as measured by ELISA using rPyMSP-1$_{42}$ or GST-PyMSP-1$_{19}$ coated plates. The quantity of antibodies recognizing PyMSP-1$_{19}$ epitopes that was induced by immunization with the chimeric rPyMSP-1/8 was about 50-fold greater than that induced by immunization with rPyMSP-1$_{42}$ alone (FIG. 3B, p<0.01). Due to this marked and unexpected improvement in PyMSP-1$_{19}$ immunogenicity, the previous problem observed in Experimental Example 2 of competition between MSP-1 and MSP-8 in mice immunized with an admixture of rPyMSP-1$_{42}$ and rPyMSP-8 was overcome.

Figure 6:
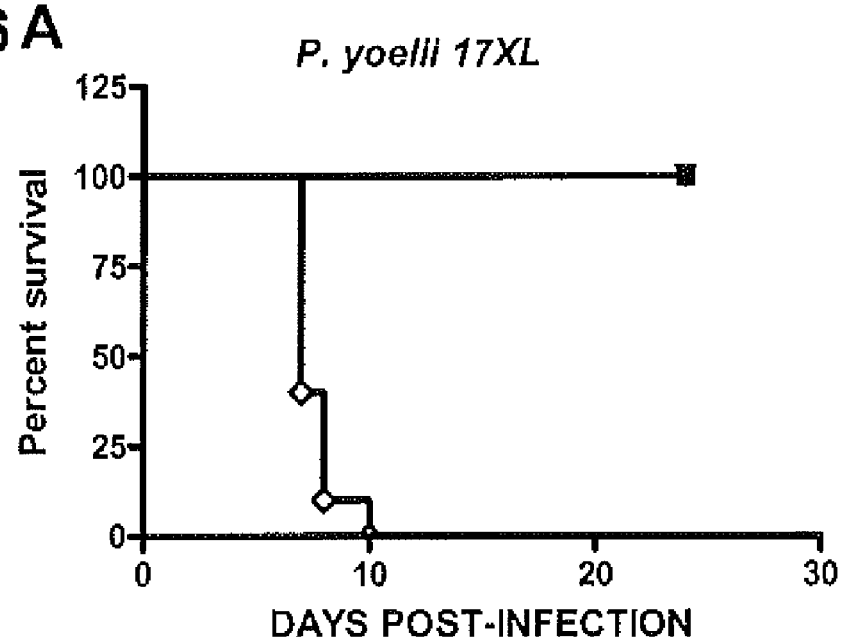
FIGS. 6A and 6B are a series of graphs depicting data from mice immunized with rPyMSP-8 or rPyMSP1/8 and challenged with lethal P. yoelli 17XL. BALB/cByJ mice (n=10) were immunized with rPyMSP-8 (■, 10 μg) or rPyMSP1/8 (▼, 14 μg) formulated with Quil A as adjuvant or with Quil A alone (◇). Two weeks following the third immunization, mice were challenged with 1×10$^5$ P. yoelii 17XL-parasitized erythrocytes.
Figure 6:
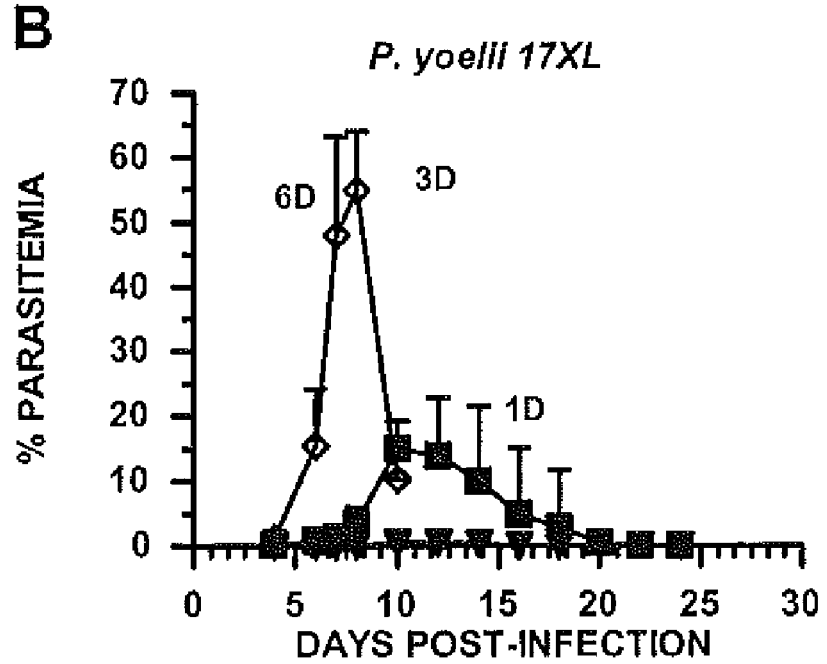

As shown in FIG. 6A, all mice immunized with either rPyMSP-8 or rPyMSP-1/8 survived lethal *P. yoelii* 17XL challenge, with all adjuvant control animals succumbing to infection by day 10. As measured by reduction in peak parasitemia in immunized and protected mice, the efficacy of immunization with the chimeric rPyMSP-1/8 was markedly improved relative to rPyMSP-8. As shown in FIG. 6B, all mice immunized with rPyMSP-1/8 cleared *P. yoelii* 17XL parasites from circulation, with a remarkably low mean peak parasitemia of only 0.9%±0.8%. Mice immunized with rPyMSP-8, on the other hand, developed a significantly higher parasitemia reaching a mean peak of 18.8%±7.7% between days 10 and 14 of infection before final parasite clearance (p<0.01).

Combined, the data clearly indicate that immunization with the chimeric rPyMSP-1/8 vaccine provided high, nearly-complete protection against *P. yoelii* 17XL malaria. This level of protection could not be achieved by immunization with rPyMSP-1$_{42}$ alone, rPyMSP-8 alone, or a mixture of rPyMSP-1$_{42}$ and rPyMSP-8.

Figure 7A:
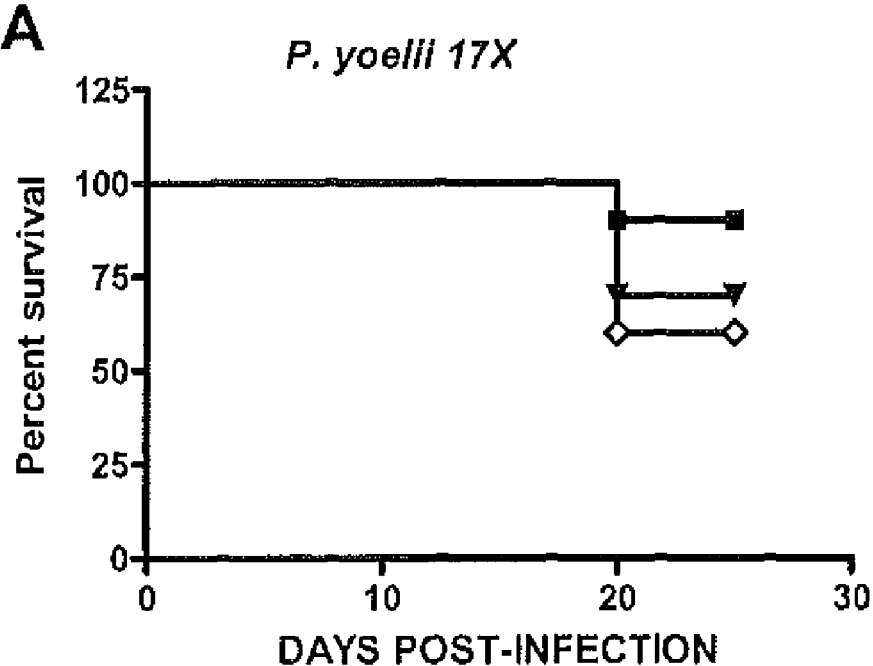
FIGS. 7A and 7B are a series of graphs depicting data from mice immunized with rPyMSP-8 or rPyMSP-1/8 and challenged with a nonlethal, reticulocyte-restricted P. yoelii 17X strain. BALB/cByJ mice (n=10) were immunized with rPyMSP-8 (■, 10 μg) or rPyMSP1/8 (▼, 14 mg) formulated with Quil A as adjuvant or with Quil A alone (◇). Two weeks following the third immunization, mice were challenged with non-lethal, reticulocyte-restricted 17X strain of P. yoelii.
Figure 7B:
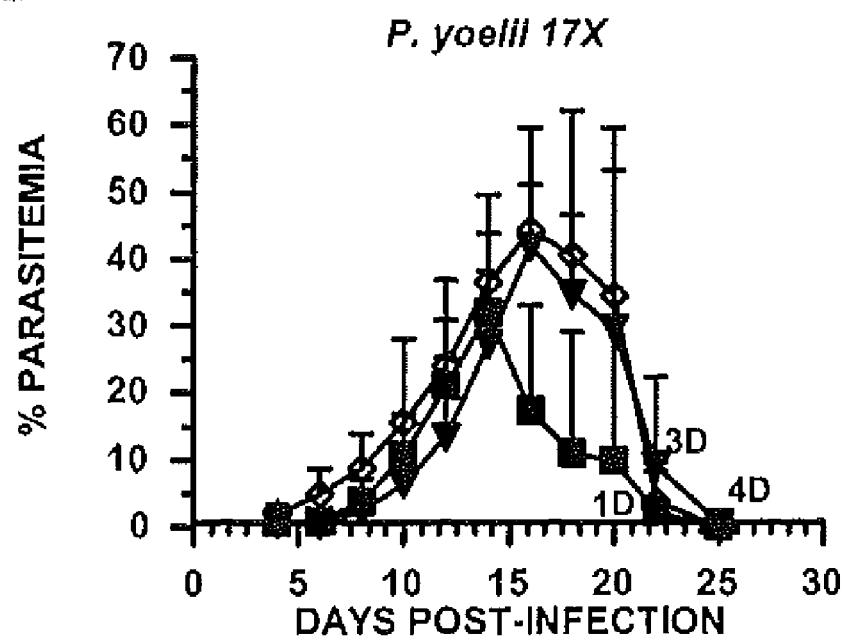

In contrast, mice immunized with rPyMSP-8 or the chimeric rPyMSP-1/8 showed little or no reduction in parasitemia following challenge with the nonlethal, reticulocyte-restricted *P. yoelii* 17X strain of parasites (FIG. 7). Peak parasitemia in rPyMSP-8 reached a mean of 34.7%±10.9%, somewhat lower than that of 47.9%±14.8% in Quil A control mice (p<0.05). However, the mean peak parasitemia in rPyMSP-1/8 immunized mice of 44.4%±11.6% was not different than adjuvant controls (p>0.05). Late during infection, animals in each experimental group that had not cleared parasites and were anemic were sacrificed. The difference in mortality between groups was not significant (p>0.05). The inability to protect mice against reticulocyte-restricted blood-stage parasites using a highly efficacious vaccine that suppresses growth of blood-stage parasites in mature RBCs must be further investigated.

Experimental Example 5

Prolonged Protection Against *P. yoelii* 17XL Malaria Induced by Immunization with the Chimeric rPyMSP-1/8 Vaccine The ability of the rPyMSP-1/8 vaccine to induce sustained protection against *P. yoelii* 17XL malaria was tested in two additional protocols. In the first protocol, the ability of the rPyMSP-1/8 vaccine to protect against repeated parasite exposure was evaluated. BALB/cByJ mice were immunized as above with rPyMSP-1/8 (3×, 14 µg/dose) formulated with Quil A as adjuvant (n=10) or with Quil A alone (n=7). Two weeks after the final immunization, mice were challenged with *P. yoelii* 17XL.

Figures 8A, 8B:
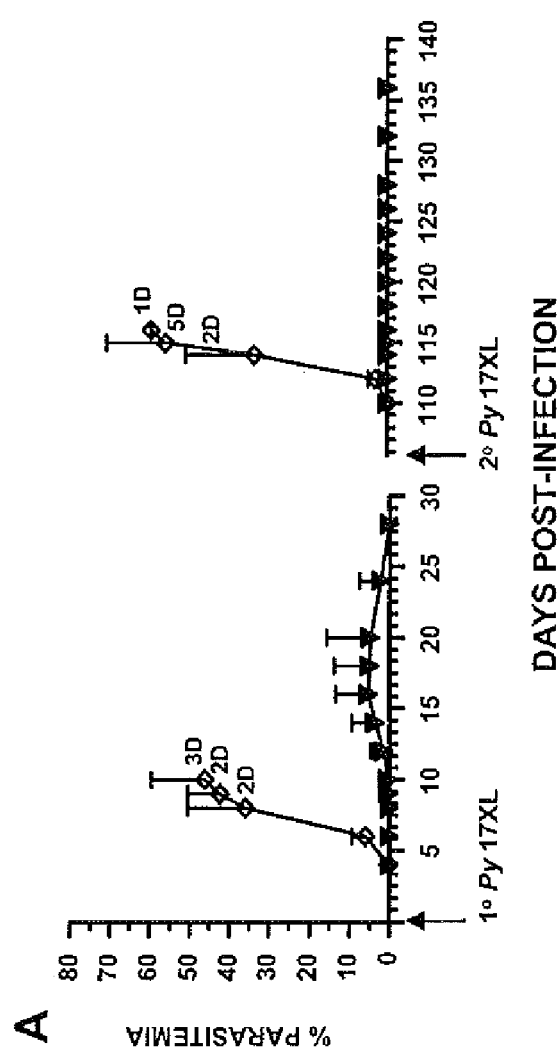
FIGS. 8A and 8B are a series of graphs depicting data from mice immunized with rPyMSP1/8 and challenged with P. yoelli 17XL parasitized erythrocytes.

As before, mice immunized with rPyMSP-1/8 were solidly protected, with 100% survival and mean daily parasitemia of <6% Parasitemia in animals immunized with adjuvant alone was fulminate and resulted in 100% mortality by day 12 post-infection (FIG. 8A, 1° Py 17XL). Mice immunized with rPyMSP-1/8 and protected against *P. yoelii* malaria were then rested for approximately 3.5 months. No blood-stage parasites were detected during this time period. On day 106 following the first challenge infection, rPyMSP-1/8 immunized mice were then rechallenged with *P. yoelii* 17XL. As expected, all control mice succumbed to *P. yoelii* 17XL malaria by day 11 post-infection. However, rPyMSP-1/8 immunized mice were still solidly protected against a second exposure to lethal *P. yoelii* malaria (FIG. 8A, 2° Py 17XL).

The second protocol was designed to determine if protection induced by immunization with the chimeric rPyMSP-1/8 vaccine waned in the absence of exposure to blood-stage malaria parasites. BALB/cByJ mice were immunized as above with rPyMSP-1/8 (3×, 14 ug/dose) formulated with Quil A as adjuvant (n=9) or with Quil A alone (n=8). Following the final immunization, mice were rested. Primary challenge infection with *P. yoelii* 17XL was delayed for 17 weeks (~4 months) following the last immunization with the rPyMSP-1/8 vaccine.

Despite the long period of time between immunization and challenge, protective efficacy of the rPyMSP-1/8 vaccine remained very high with 8/9 mice surviving an otherwise lethal challenge infection and clearing blood-stage parasites from circulation (FIG. 8B). Combined, these data indicate that immunization with the rPyMSP-1/8 vaccine induces sustained protection against repeated infection with blood-stage malaria parasites.

Experimental Example 6

Conformational Epitopes of rPyMSP-1, rPyMSP-8 and Chimeric rPyMSP1/8 Antigens In considering the enhanced efficacy of the chimeric vaccine, it is possible that the conformation of PyMSP-$1_{19}$ and/or PyMSP-8 portions of rPyMSP-1/8 more accurately mimicked the native antigens in comparison to individual rPyMSP-1 or rPyMSP-8 antigens. Alternatively, it could be that an interaction between PyMSP-$1_{19}$ and PyMSP-8 within the chimeric rPyMSP-1/8 resulted in the formation of novel protective epitopes. To test these possibilities, sera from mice immunized with the rPyMSP-1/8 were collected and passed over columns of immobilized 1) rPyMSP-8 and 2) GST-PyMSP-$1_{19}$. Reactivity of unabsorbed and absorbed sera was then compared by ELISA on wells coated with GST-PyMSP-$1_{19}$, rPyMSP-8 or rPyMSP-1/8.

Figure 9A:
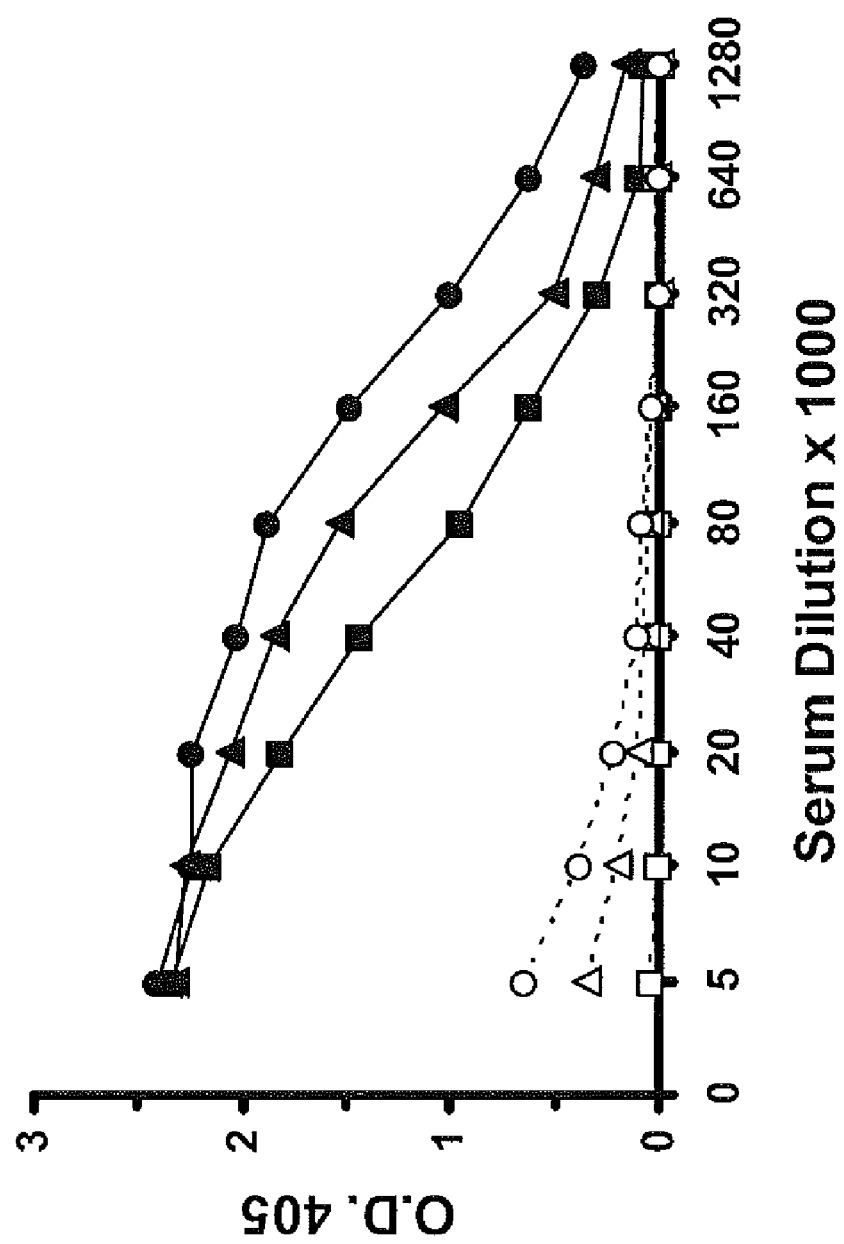

As shown in FIG. 9A, removal of antibodies from the anti-rPyMSP-1/8 sera that reacted with GST-PyMSP-$1_{19}$ and rPyMSP-8 reduced reactivity with the chimeric rPyMSP-1/8 by >95%. In a second absorption assay, anti-rPyMSP-1/8 sera were passed over columns of immobilized 1) rPyMSP-8 and 2) rPyMSP-$1_{42}$ and reactivity of unabsorbed and absorbed sera again evaluated by ELISA. As shown in FIG. 9B, removal of antibodies from the anti-rPyMSP-1/8 sera that reacted with PyMSP-$1_{42}$ and PyMSP-8 reduced reactivity with rPyMSP-1/8 by >95%. Removal of PyMSP-$1_{42}$ reactive antibodies also eliminated reactivity with GST-PyMSP-$1_{19}$.

These data suggest that the PyMSP-1 EGF-like domains of GST-PyMSP-$1_{19}$, rPyMSP-$1_{42}$ and rPyMSP-1/8 bear a similar, if not identical, conformation. Likewise, the overall conformation of PyMSP-8 is similar when expressed alone or as part of the chimeric PyMSP-1/8 antigen. Based on an overall assessment of the immunogenicity and efficacy data obtained, and without wishing to be bound by theory, the dramatic increase in the efficacy of the chimeric *P. yoelii* MSP-1/8 vaccine against *P. yoelii* 17XL malaria is most likely due to the increase in the immunogenicity of MSP-$1_{19}$ and the concurrent targeting of both MSP-1 and MSP-8 antigens.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inducing an immune response in an animal, the method comprising
administering to the animal an effective amount of a composition comprising a chimeric protein, wherein said chimeric protein comprises *Plasmodium* merozoite surface protein-8 (MSP-8) linked to MSP-1$_{19}$.

2. The composition of claim 1, wherein said MSP-1$_{19}$ is covalently linked to said MSP-8.

3. The composition of claim 1, wherein said MSP-8 and said MSP-1$_{19}$ are *P. falciparum* or *P. vivax* sequences.

4. The composition of claim 1, further comprising a pharmaceutically acceptable carrier.

5. The composition of claim 1, further comprising an adjuvant.

6. The composition of claim 2, wherein MSP-1$_{19}$ is covalently linked to MSP-8 to form a fusion protein comprising the sequence of SEQ ID No. 23.

* * * * *